(12) United States Patent
Chisena et al.

(10) Patent No.: US 12,279,782 B2
(45) Date of Patent: *Apr. 22, 2025

(54) PULSATILE BALLOON CATHETER SYSTEMS AND METHODS OF USING THE SAME

(71) Applicant: Amplitude Vascular Systems, Inc., Boston, MA (US)

(72) Inventors: Robert Chisena, Boston, MA (US); Hitinder Gurm, Boston, MA (US)

(73) Assignee: Amplitude Vascular Systems, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/593,803

(22) Filed: Mar. 1, 2024

(65) Prior Publication Data

US 2024/0285294 A1  Aug. 29, 2024

Related U.S. Application Data

(63) Continuation of application No. 17/827,169, filed on May 27, 2022, which is a continuation-in-part of
(Continued)

(51) Int. Cl.
*A61B 17/22* (2006.01)
*A61B 17/00* (2006.01)
(Continued)

(52) U.S. Cl.
CPC ........ *A61B 17/22012* (2013.01); *A61M 5/007* (2013.01); *A61B 2017/00022* (2013.01);
(Continued)

(58) Field of Classification Search
CPC ........ A61B 17/22012; A61B 2090/064; A61B 2017/00022; A61B 2017/00039;
(Continued)

(56) References Cited

U.S. PATENT DOCUMENTS

| 2,918,917 A | 12/1959 | Emerson |
| 3,769,960 A | 11/1973 | Robinson |
| (Continued) | | |

FOREIGN PATENT DOCUMENTS

| CA | 2651380 C | 5/2015 |
| DE | 19936162 A1 | 2/2001 |
| (Continued) | | |

OTHER PUBLICATIONS

Blankenship et al., Comparison of Slow Oscillating Versus Fast Balloon Inflation Strategies for Coronary Angioplasty, The American Journal of Cardiology, vol. 83, No. 5, Mar. 1999, p. 675-680, abstract only.

(Continued)

*Primary Examiner* — Tan-Uyen T Ho
*Assistant Examiner* — Cherie M Poland
(74) *Attorney, Agent, or Firm* — Bret E. Field; Bozicevic, Field & Francis LLP

(57) ABSTRACT

Pulsatile balloon catheter systems are provided. Aspects of the systems include: a pulse generator; and a balloon catheter assembly operably connected to the pulse generator. In embodiments, the balloon catheter assembly includes: a proximal connector operably connecting the balloon catheter assembly to the pulse generator and configured to transduce a first pulse energy generated by the pulse generator to a second pulse energy; a distal balloon; and a catheter component, where the catheter component includes a fluidic passage operably positioned between the proximal connector and the distal balloon, which passage is configured to propagate the second pulse energy from the proximal connector along the fluid passage to the distal balloon. Also provided are balloon catheter assemblies and kits that include the same. Also provided are systems and methods for assessing vessel compliance in-vivo. Also provided are (Continued)

systems and methods for determining system state of balloon catheter systems. The systems, assemblies and kits find use in a variety of different applications, including balloon angioplasty applications.

26 Claims, 31 Drawing Sheets

Related U.S. Application Data application No. PCT/US2022/014785, filed on Feb. 1, 2022.

(60) Provisional application No. 63/274,832, filed on Nov. 2, 2021, provisional application No. 63/241,295, filed on Sep. 7, 2021, provisional application No. 63/145,641, filed on Feb. 4, 2021.

(51) Int. Cl.
*A61B 90/00* (2016.01)
*A61M 5/00* (2006.01)

(52) U.S. Cl.
CPC ............ *A61B 2017/00039* (2013.01); *A61B 2017/00477* (2013.01); *A61B 2017/00964* (2013.01); *A61B 2017/22001* (2013.01); *A61B 2017/22038* (2013.01); *A61B 2017/22054* (2013.01); *A61B 2017/22062* (2013.01); *A61B 2090/063* (2016.02); *A61B 2090/064* (2016.02)

(58) Field of Classification Search
CPC ........... A61B 2017/00477; A61B 2017/00964; A61B 2017/22001; A61B 2017/22038; A61B 2017/22054; A61B 2017/22062; A61M 5/007
See application file for complete search history.

(56) References Cited

U.S. PATENT DOCUMENTS

| | | | |
|---|---|---|---|
| 4,332,254 A | 6/1982 | Lundquist |
| 4,446,867 A | 5/1984 | Leveen et al. |
| 4,936,281 A | 6/1990 | Stasz |
| 5,021,046 A | 6/1991 | Wallace |
| 5,215,523 A | 6/1993 | Williams et al. |
| 5,308,356 A | 5/1994 | Blackshear, Jr. et al. |
| 5,318,533 A | 6/1994 | Adams et al. |
| 5,344,395 A | 9/1994 | Whalen et al. |
| 5,407,424 A | 4/1995 | LaFontaine et al. |
| 5,458,468 A | 10/1995 | Ye et al. |
| 5,460,609 A | 10/1995 | O'Donnell |
| 5,545,133 A | 8/1996 | Burns et al. |
| 5,599,301 A | 2/1997 | Jacobs et al. |
| 5,609,606 A | 3/1997 | O'Boyle |
| 5,611,807 A | 3/1997 | O'Boyle |
| 5,722,979 A | 3/1998 | Kusleika |
| 5,846,218 A | 12/1998 | Brisken et al. |
| 5,891,089 A | 4/1999 | Katz et al. |
| 5,944,687 A | 8/1999 | Benett et al. |
| 6,176,235 B1 | 1/2001 | Benarrouch et al. |
| 6,179,815 B1 | 1/2001 | Foote |
| 6,354,999 B1 | 3/2002 | Dgany et al. |
| 6,544,224 B1 | 4/2003 | Steese-Bradley |
| 7,166,098 B1 | 1/2007 | Steward et al. |
| 7,604,618 B2 | 10/2009 | Dixon et al. |
| 7,942,850 B2 | 5/2011 | Levit et al. |
| 7,981,078 B2 | 7/2011 | Mandel |
| 7,998,107 B2 | 8/2011 | Nash et al. |
| 8,147,511 B2 | 4/2012 | Perry et al. |
| 8,197,505 B2 | 6/2012 | Hirszowicz et al. |
| 8,372,034 B2 | 2/2013 | Levit et al. |
| 8,574,248 B2 | 11/2013 | Kassab |
| 8,628,555 B2 | 1/2014 | Perry et al. |
| 8,728,091 B2 | 5/2014 | Hakala et al. |
| 8,747,416 B2 | 6/2014 | Hakala et al. |
| 8,808,237 B2 | 8/2014 | Thielen et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,011,462 B2 | 4/2015 | Adams et al. |
| 9,072,534 B2 | 7/2015 | Adams et al. |
| 9,138,249 B2 | 9/2015 | Adams et al. |
| 9,333,000 B2 | 5/2016 | Hakala et al. |
| 9,364,254 B2 | 6/2016 | Gershony et al. |
| 9,375,223 B2 | 6/2016 | Wallace |
| 9,433,428 B2 | 9/2016 | Hakala et al. |
| 9,468,745 B2 | 10/2016 | Bagaoisan et al. |
| 9,642,673 B2 | 5/2017 | Adams et al. |
| 2002/0045854 A1 | 4/2002 | Royo et al. |
| 2004/0133165 A1 | 7/2004 | Duchon et al. |
| 2004/0199230 A1 | 10/2004 | Yon |
| 2007/0088380 A1 | 4/2007 | Hirszowicz et al. |
| 2008/0140101 A1 | 6/2008 | Carley et al. |
| 2009/0171278 A1 | 7/2009 | Hirszowicz et al. |
| 2009/0247945 A1 | 10/2009 | Levit et al. |
| 2011/0196412 A1 | 8/2011 | Levit et al. |
| 2012/0253186 A1 | 10/2012 | Simpson et al. |
| 2014/0343566 A1 | 11/2014 | Wenderow et al. |
| 2018/0008763 A1 | 1/2018 | Thomas et al. |
| 2020/0046949 A1 | 2/2020 | Chisena et al. |
| 2020/0305742 A1 | 10/2020 | Ghodsian |
| 2020/0306512 A1 | 10/2020 | Bahmanyar et al. |
| 2021/0100570 A1 | 4/2021 | Schoenle |
| 2021/0220064 A1 | 7/2021 | Kottenstette et al. |
| 2022/0096747 A1 | 3/2022 | McCullough et al. |

FOREIGN PATENT DOCUMENTS

| | | | |
|---|---|---|---|
| EP | 0870484 A1 | 10/1998 | |
| EP | 3643260 A1 | 4/2020 | |
| JP | 2011528963 A | 12/2011 | |
| JP | 2012-517270 A | 8/2012 | |
| KR | 10-2016-0136904 A | 11/2016 | |
| WO | WO0110491 A2 | 2/2001 | |
| WO | WO2009141810 A2 | 11/2009 | |
| WO | WO2012006625 A2 | 1/2012 | |
| WO | WO2013056006 A2 | 4/2013 | |
| WO | WO2018201037 A1 | 11/2018 | |
| WO | WO-2019200201 A1 * | 10/2019 | ....... A61B 17/22012 |
| WO | WO2021076538 A1 | 4/2021 | |

OTHER PUBLICATIONS

Blankenship et al., Coronary Dissection Resulting from Angioplasty with Slow Oscillating vs. Rapid Inflation and Slow vs. Rapid Deflation, Catheterization and Cardiovascular Diagnosis, vol. 34, No. 3, Mar. 1995, p. 202-209, abstract only.

Blankenship et al., Oscillating Balloon Angioplasty: Does Pressure Oscillation Reach the Balloon?, Catheterization and Cardiovascular Diagnosis, vol. 37, No. 1, Jan. 1996, p. 109-112, abstract only.

* cited by examiner

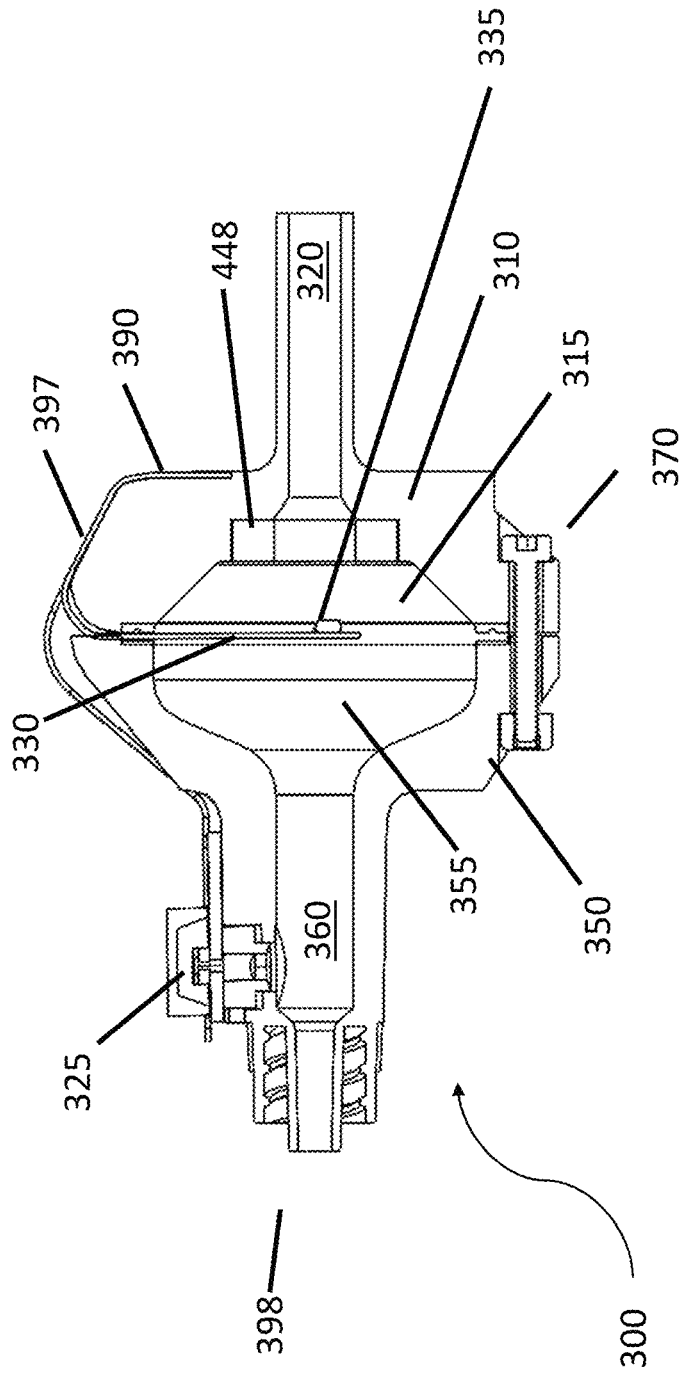

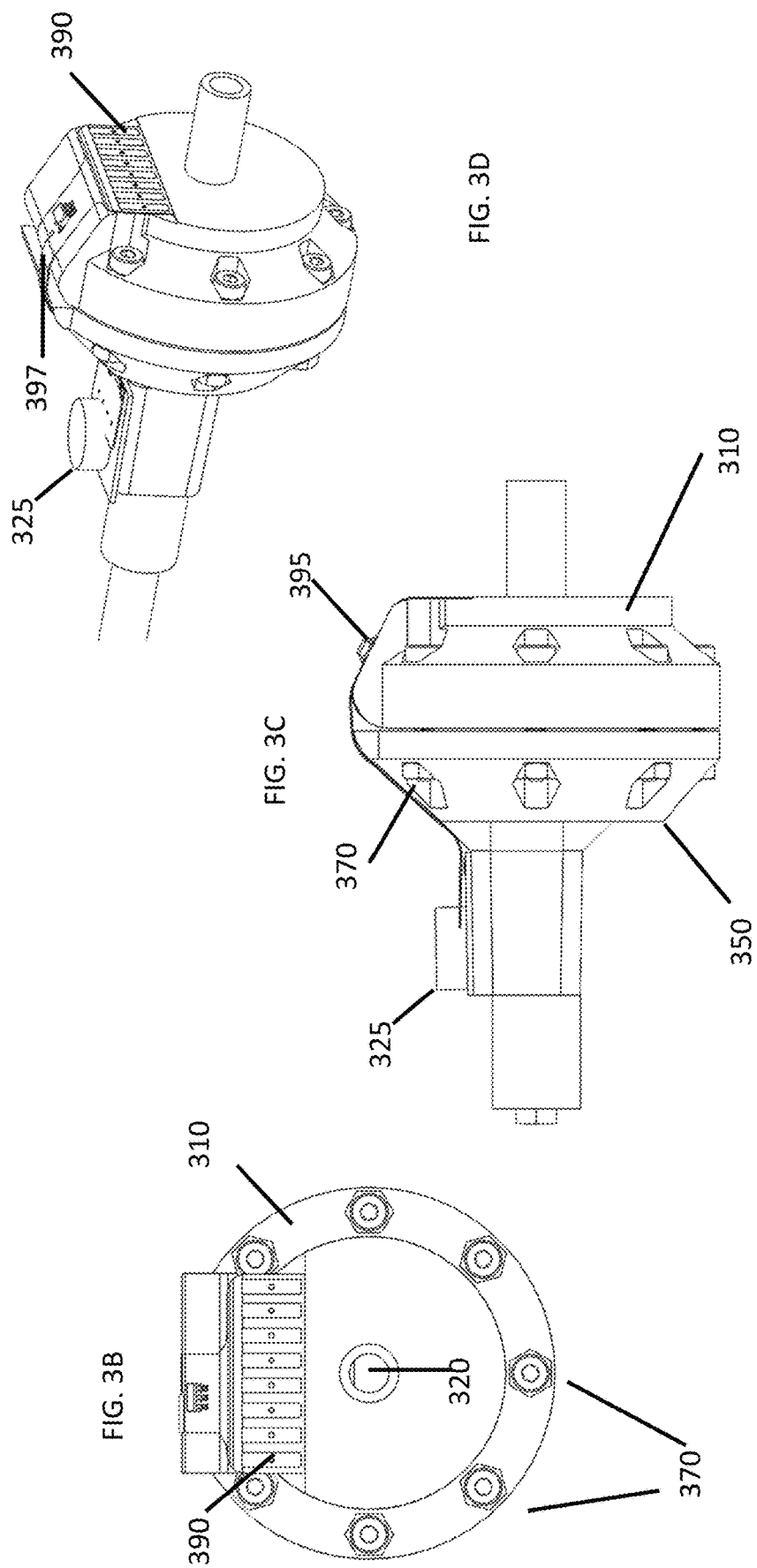

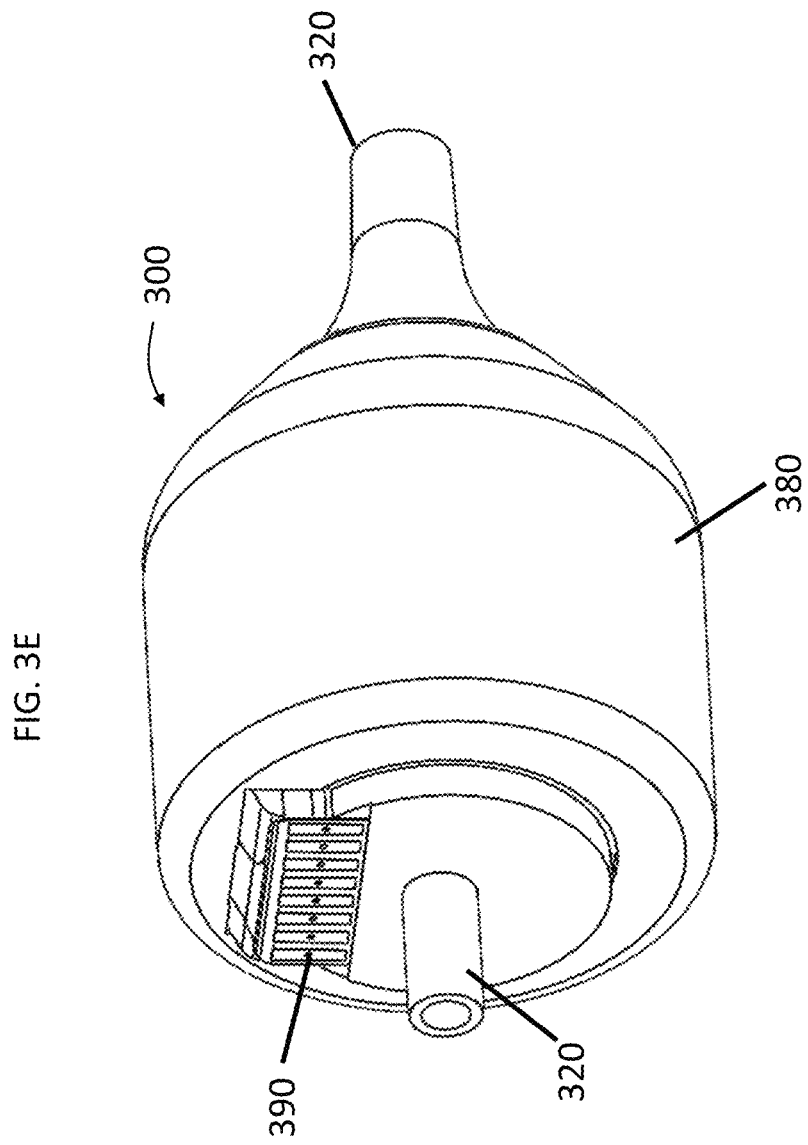

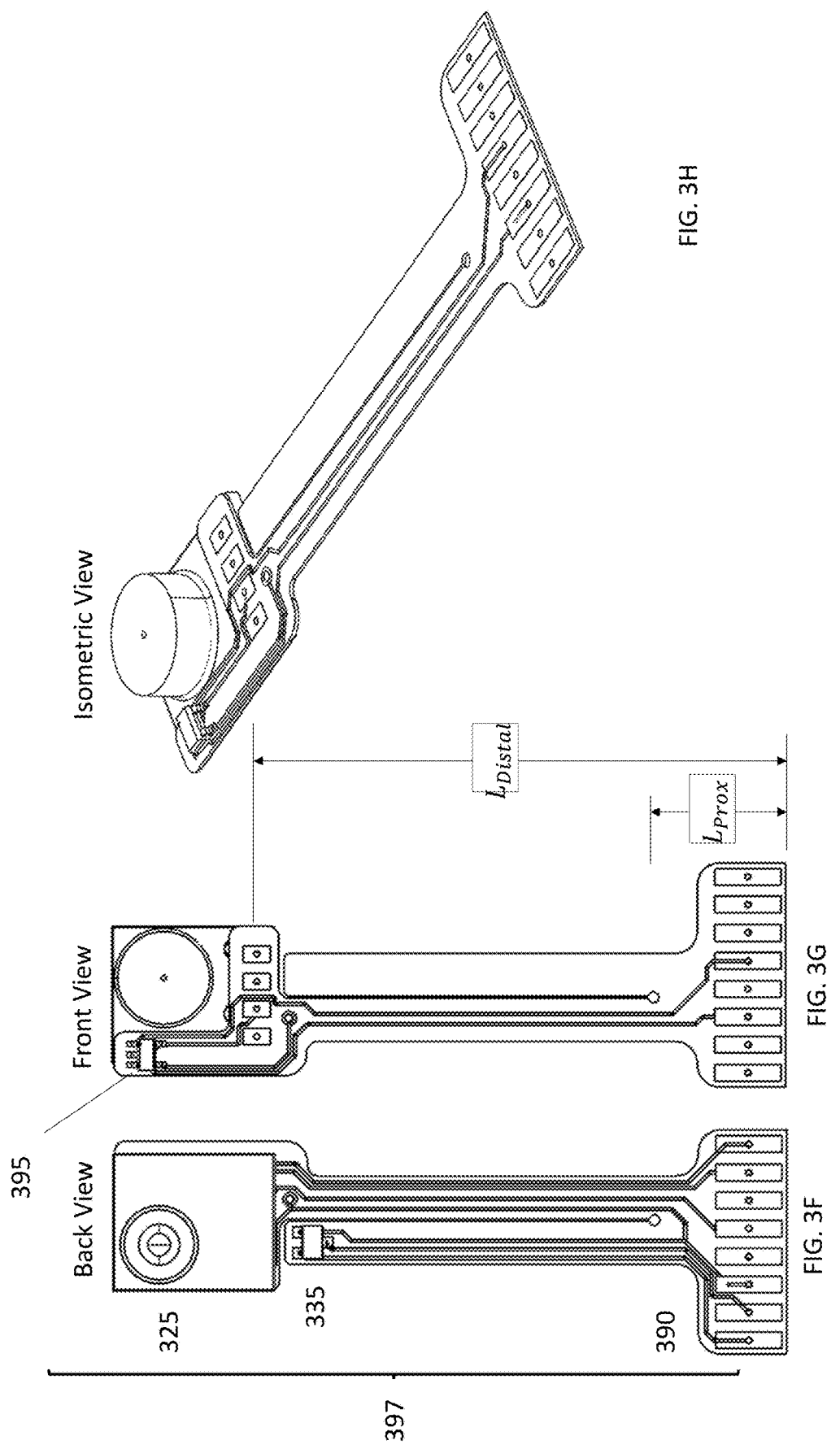

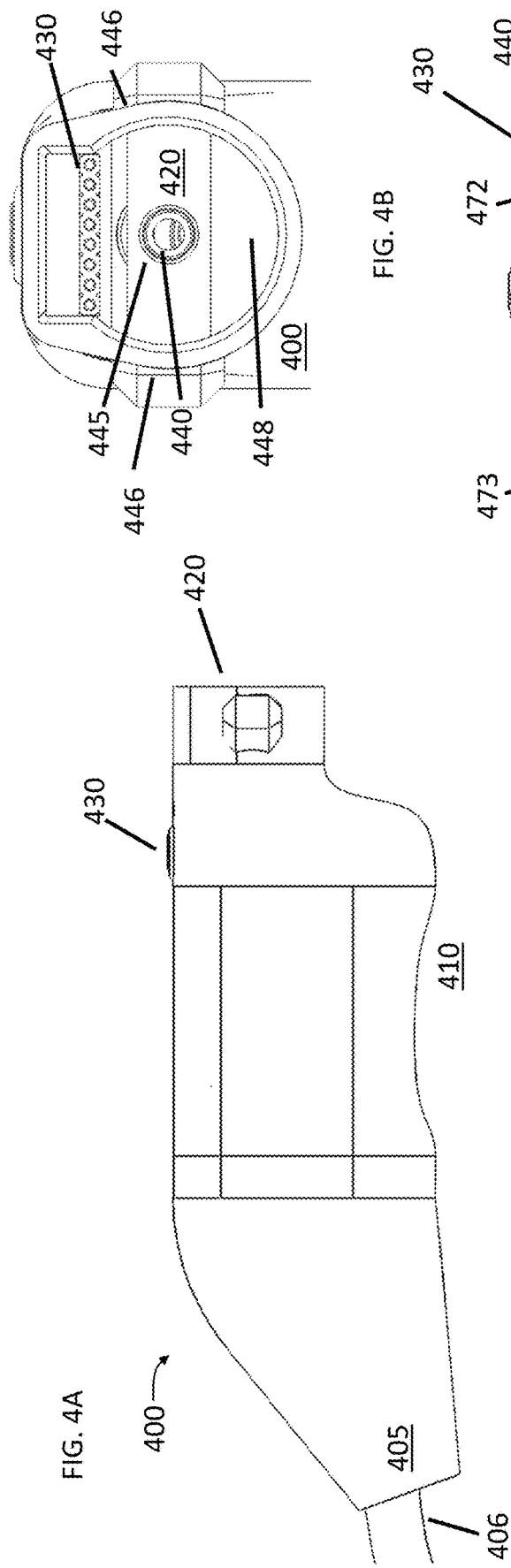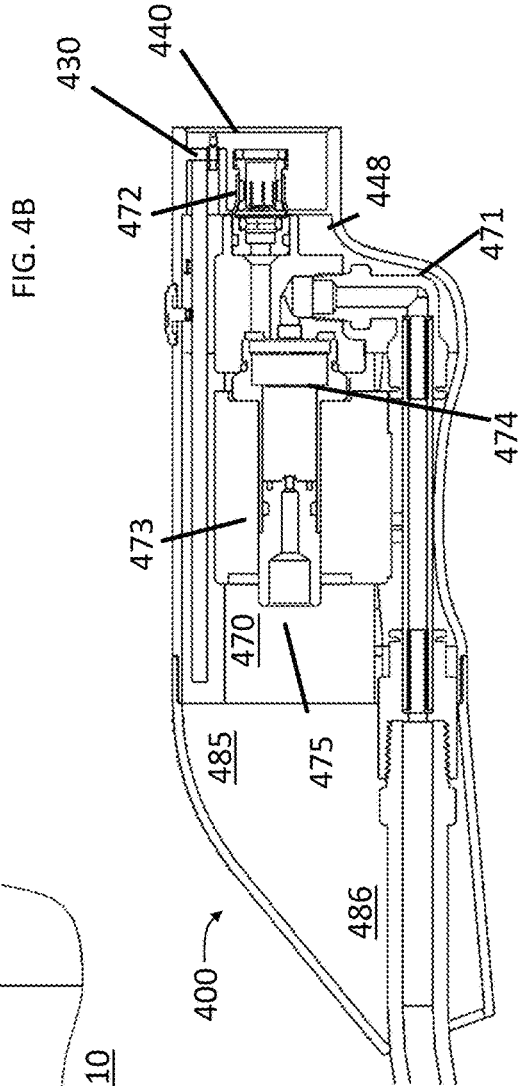

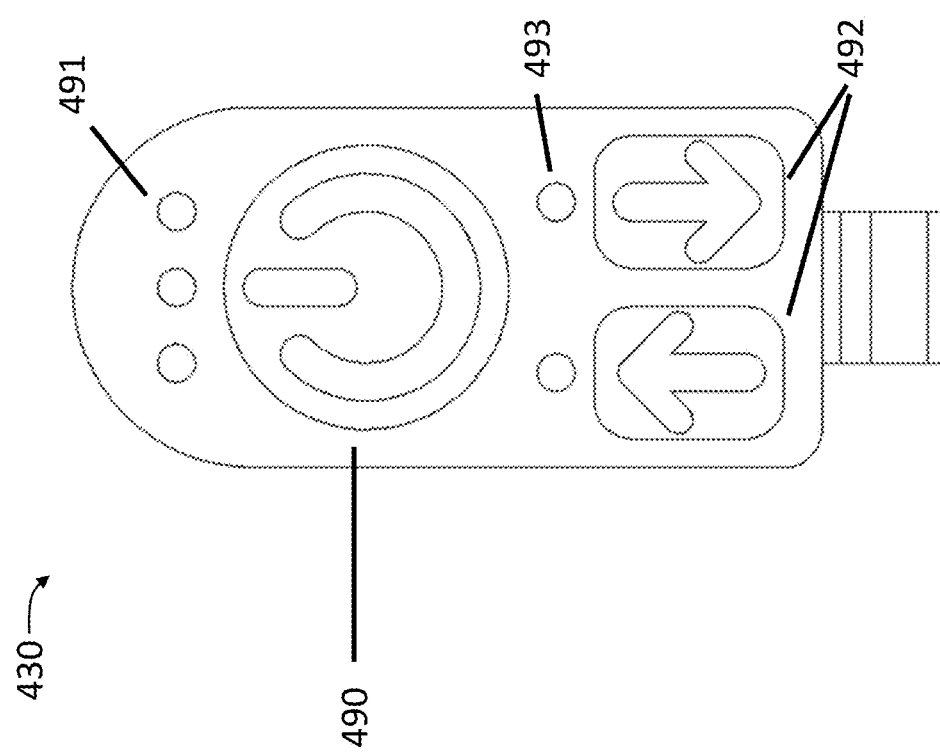

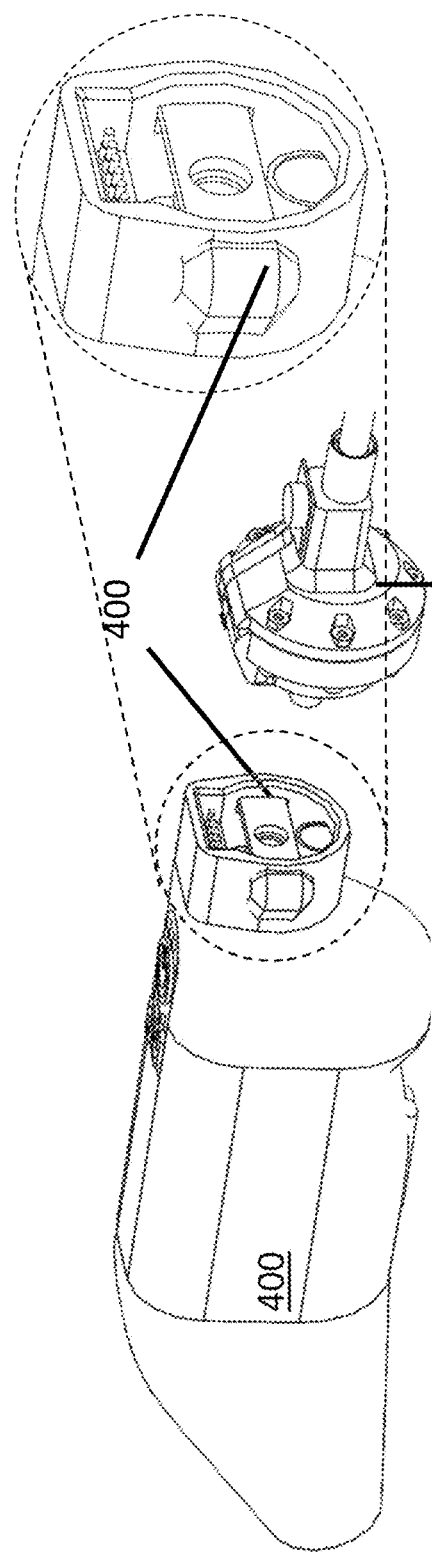
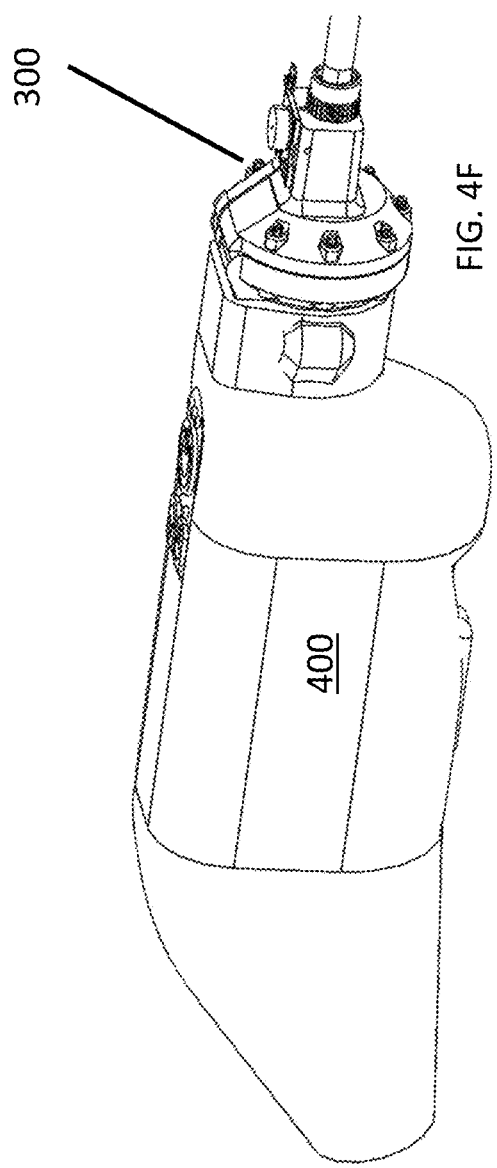
FIG. 4E
FIG. 4F

Description: (Panels A-B) Example fluoroscopy images of a focal lesion (shown by arrows). (Panels C-D) A balloon is inserted across the lesion and pressurized. In view (Panel C), the balloon appears to be expanded. However, in a normal projection image (Panel D), the balloon is under-expanded.

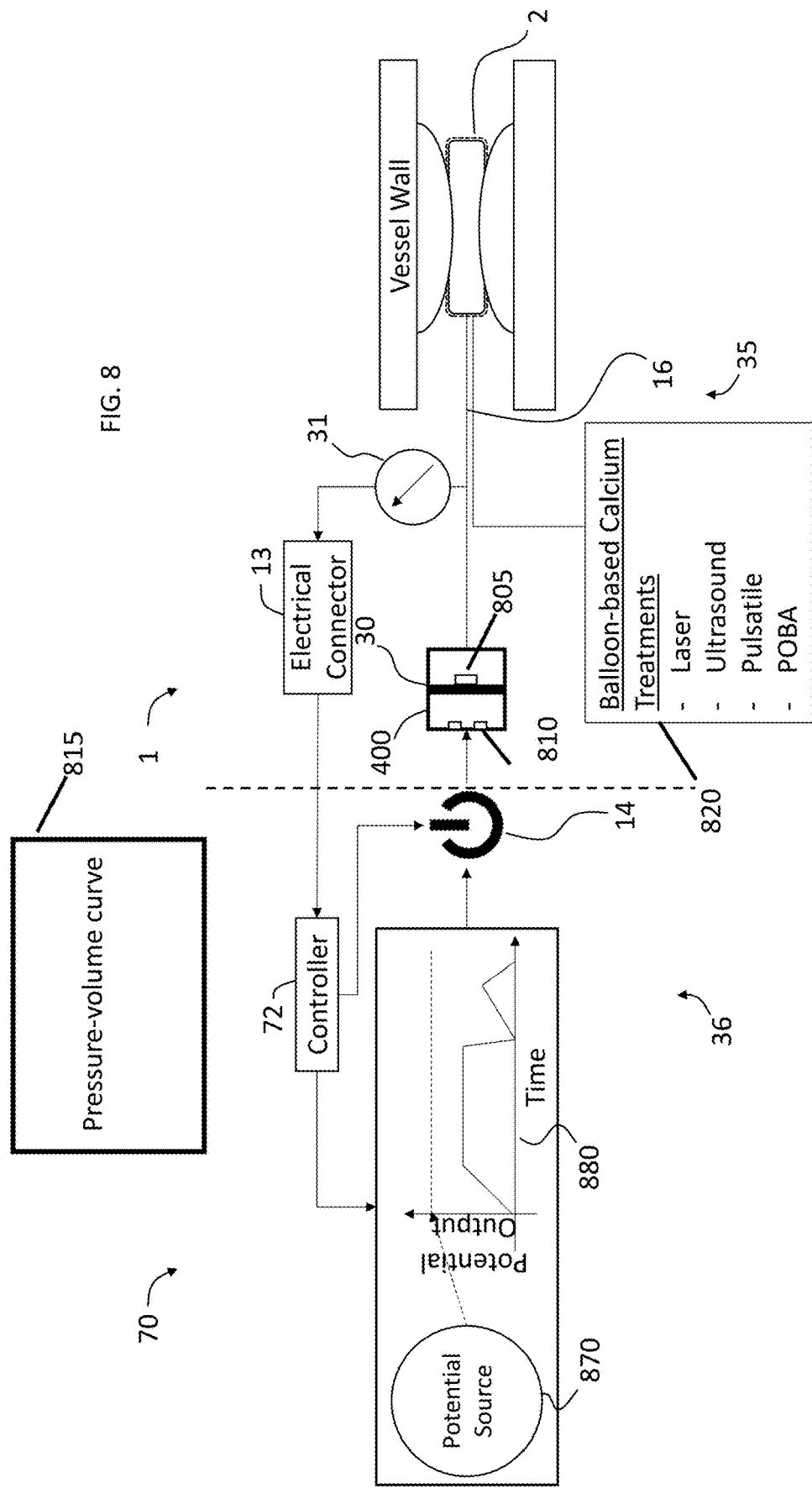

PULSATILE BALLOON CATHETER SYSTEMS AND METHODS OF USING THE SAME

CROSS-REFERENCE TO RELATED APPLICATIONS

This application is a continuation of U.S. patent application Ser. No. 17/827,169 filed May 27, 2022, which application is a continuation-in-part of International Application No. PCT/US22/14785 filed Feb. 1, 2022, which claims priority to the filing dates of: U.S. provisional patent application Ser. No. 63/274,832 filed Nov. 2, 2021; U.S. provisional patent application Ser. No. 63/241,295 filed Sep. 7, 2021; and U.S. provisional patent application Ser. No. 63/145,641 filed Feb. 4, 2021; the disclosures of which applications are incorporated herein by reference in their entirety.

INTRODUCTION

This section provides background information related to the present disclosure which is not necessarily prior art. This section also provides a general summary of the disclosure and is not a comprehensive disclosure of its full scope or all of its features.

Ischemic heart disease, the number one cause of death in the world, is caused by atherosclerotic plaque build-up within human vasculature. Worldwide, these diseases represent 84.5% of cardiovascular deaths and 28.2% of overall mortality. Ischemic heart disease is developed through a mechanism called atherosclerosis, which is the accumulation of fatty and calcified materials that cause stenosis, the narrowing of the arterial lumen. Both the coronary and peripheral arteries may suffer from atherosclerotic plaque accumulation. The plaque buildup from atherosclerosis limits blood flow through these arteries and can lead to major adverse cardiovascular events such as myocardial infarction, limb amputation, and mortality. In the early stages of atherosclerosis, plaques are soft and fatty, but as time and the disease progress, these plaques physically harden, or calcify. Calcified plaque (CP) that develops in the innermost layer of the artery wall occurs most frequently. These CPs result from the deposition and remodeling of calcium hydroxyapatite, a process that mimics bone formation. CP-burdened vessels have reduced vascular elasticity and impaired vessel perfusion. Because of this reduced compliance and perfusion, CPs are associated with an increased risk of mortality and other adverse events.

While many patients with CP are asymptomatic, a substantial number of patients develop symptoms and signs related to ischemia and undergo endovascular or surgical repair. Given its lower morbidity, endovascular approaches are generally favored. However, CP-burdened vessels pose special challenges for effective intravascular treatments. To treat CP-burdened vessels, a series of devices are often used. The CP-lesion is first pre-dilated using balloon angioplasty (BA). During BA, a balloon is advanced to the affected artery and is expanded to dilate a plaque-burdened vessel to restore normal blood flow. This pre-dilation step must be successful before secondary therapies such as drug-coated balloons or stents can be successfully used. For successful pre-dilation, BA must mechanically fracture the CP to ensure the long-term opening, or patency, of the vessel and to re-establish the elasticity of the surrounding healthy vessel. Often, high-pressure, non-compliant balloons are used to achieve success. However, because of the strength of CP, full balloon expansion is often restricted, and the CP remains unfractured. Without sufficient balloon expansion and CP fracture, the vessel remains with a residual stenosis limiting downstream blood flow indicating a poor outcome, a high risk of immediate or long-term failure, and the need for additional procedures. To ensure patency of diseased vessels, the high rupture strength of the CP must be overcome.

During standard BA, a pressurized catheter balloon is used to fracture atherosclerotic plaques and expand them into artery walls to re-establish normal blood flow in stenosed arteries. Typically, the balloon is pressurized via a manually actuated screw-driven syringe, which converts rotations of a physician-facing handle into a displacement of the syringe piston. The handle of the syringe is rotated by a clinician until the pressure within the system reaches a desired pressure, or the physician senses fracture of the calcified plaque. During treatment, the physician can sense if the calcified plaque has fractured in two ways: (1) from the outline of the balloon under fluoroscopy, a medical imaging technique commonly used in cardiovascular procedures, and (2) from a reduction in pressure within the hydraulic system as indicated by a pressure gauge. During angioplasty procedures, a radiopaque dye (i.e., contrast agent) is introduced into the balloon, which under fluoroscopy, illuminates the outline of the balloon and arterial walls. When the plaque is intact and the balloon is pressurized, the balloon assumes a characteristic dog-bone shape in which the proximal and distal edges are unrestricted to expand but the middle is obstructed by the plaque. The shape of the dog-bone informs the clinician of the severity and distribution of the plaque. In some scenarios, the entire artery is diseased, and the balloon remains uniformly unexpanded and does not achieve a full diameter. In other scenarios, the balloon may have indentation in one or more planes suggesting an eccentric plaque. A more uniformly expanded balloon indicates to the physician that the plaque has been treated. The second method used to sense plaque fracture is indicated by the pressure gauge attached to the balloon. When treating severe and/or circumferentially distributed plaque, pressure is increased in the balloon until the plaque fractures. Prior to fracture of the plaque, the balloon maintains the previously described restricted shape (e.g., a dog bone-shape). Upon fracture, the plaque no longer restricts the balloon expansion, and the balloon expands the plaque into the elastic artery. With this balloon expansion, the volume of the balloon increases, transforming it from a restricted shape (e.g., a dog-bone shape) into a fully expanded cylindrical shape. This volume increase causes the pressure in the balloon to drop, a change that may be visualized or sensed from the connected pressure gauge.

To overcome the rupture strength of CP, angioplasty balloons are often used in an off-label (i.e., not FDA-approved) fashion to aggressively expand CP-burdened vessels. In these cases, balloons are pressurized past their rated burst pressures (i.e., >20-40 ATM of pressure) to achieve sufficient balloon expansion that dilates the artery. These aggressive procedures subject patients to increased risks such as balloon rupture in 21% of cases, vessel dissection in 76% of cases and restenosis (i.e., post-procedure vessel re-narrowing) in 20-30% of cases. Other treatment strategies that attempt to fracture CP include cutting and scoring BA and Shockwave lithotripsy BA. Cutting balloons, which are balloons surrounded by sharp-tipped metallic blades, and scoring balloons, which are balloons constrained in a metallic cage, aim to generate stress concentrations for CP fracture. During balloon pressurization, the metallic blades or cage can become embedded in soft-tissue or CP causing major procedural issues. Poor outcomes have been associated with these balloons including restenosis in 20-30% of cases and major adverse events such as vessel perforation, myocardial infarction, or death in 6% of cases. Shockwave BA employs low-pressure balloons with embedded shockwave-generating lithotripters. Short-term efficacy and safety with lithotripsy devices have been demonstrated through clinical trials; however, recent case reports have shown that these >50 ATM cavitation explosions lead to dangerous arterial dissections and perforations. Another commonly employed treatment for CP is atherectomy, a technique that uses grinding to debulk CP. However, atherectomy is more challenging technically and grinds CP and surrounding healthy tissue, which can lead to long-term vessel injury.

In addition to the concern for patient outcomes, endovascular procedures and surgeries can significantly affect the treating physician. Over an interventional cardiologists' career, s/he can be exposed to an estimated 50 mSv-200 mSv of ionizing radiation, which is equivalent to 2,500-10,000 chest X-rays. With this amount of radiation exposure, treating physicians are exposed to serious long-term health issues such as cancer, cataracts, cognitive function, and reproductive effects. To mitigate the risks of ionizing radiation backscatter, physicians wear personal protective equipment (PPE) (e.g., heavy lead suits) for protection. Because of this PPE, a statistically significant group of interventional cardiologists reported musculoskeletal injuries that may have the effect of shortening careers.

There continues to be a need for improved balloon angioplasty devices and methods of use.

SUMMARY

Pulsatile balloon catheter systems are provided. Aspects of the systems include: a pulse generator; and a balloon catheter assembly operably connected to the pulse generator. In embodiments, the balloon catheter assembly includes: a proximal connector operably connecting the balloon catheter assembly to the pulse generator and configured to transduce a first pulse energy generated by the pulse generator to a second pulse energy; a distal balloon; and a catheter component, where the catheter component includes a fluidic passage operably positioned between the proximal connector and the distal balloon, which passage is configured to propagate the second pulse energy from the proximal connector along the fluid passage to the distal balloon. Also provided are aspects of robotic and/or stand-alone balloon catheter systems. Also provided are balloon catheter assemblies and kits that include the same. Also provided are systems and methods for assessing vessel compliance in-vivo. Also provided are systems and methods for determining system state of balloon catheter systems. The systems, assemblies and kits find use in a variety of different applications, including balloon angioplasty applications.

BRIEF DESCRIPTION OF THE FIGURES

FIGS. 3A to 3H provide various views of a proximal connector of a balloon catheter assembly according to an embodiment of the invention.

FIGS. 4A to 4F provide various views of a hand-held actuator of a pulse generator according to an embodiment of the invention.

FIG. 8 provides a schematic diagram of a system according to an embodiment of the invention configured to assess vessel compliance in-vivo.

DETAILED DESCRIPTION

Figure 1:
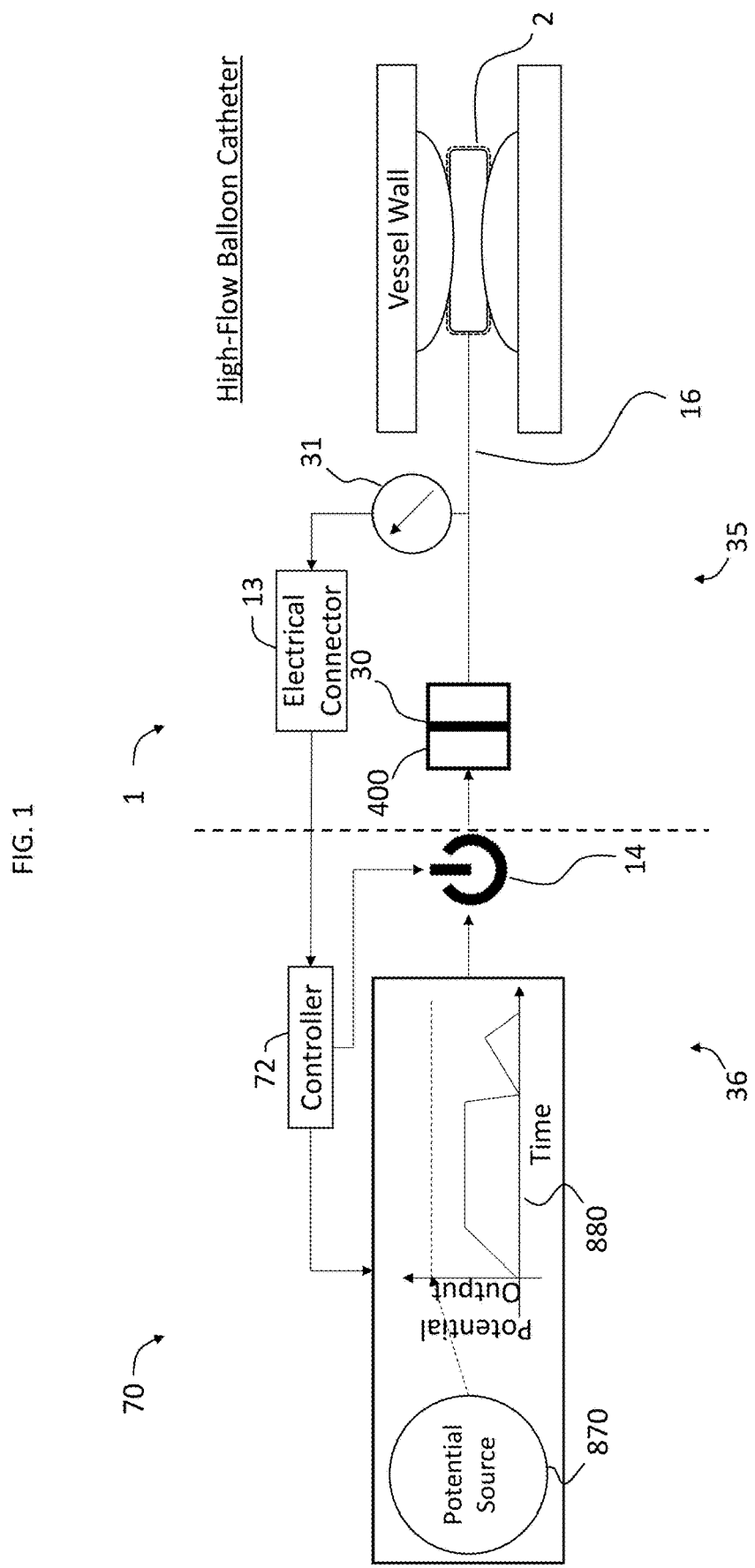
FIG. 1 provides a schematic diagram of a system according to an embodiment of the invention.

Pulsatile balloon catheter systems are provided. Aspects of the systems include: a pulse generator; and a balloon catheter assembly operably connected to the pulse generator. In embodiments, the balloon catheter assembly includes: a proximal connector operably connecting the balloon catheter assembly to the pulse generator and configured to transduce a first pulse energy generated by the pulse generator to a second pulse energy; a distal balloon; and a catheter component, where the catheter component includes a fluidic passage operably positioned between the proximal connector and the distal balloon, which passage is configured to propagate the second pulse energy from the proximal connector along the fluid passage to the distal balloon. Also provided are aspects of robotic balloon catheter systems. Also provided are balloon catheter assemblies and kits that include the same. The systems, assemblies and kits find use in a variety of different applications, including balloon angioplasty applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

In further describing various aspects of the invention, the systems and components thereof are described first in greater detail, followed by a review of methods of using the systems as well as kits for practicing the subject methods.

Pulsatile Balloon Catheter Systems

As summarized above, pulsatile balloon catheter systems are provided. Pulsatile balloon catheter systems of embodiments of the invention are configured to provide a distal end balloon that imparts pulsatile energy to internal tissue (e.g., luminal vascular tissue, such as an arterial inner wall location) in contact therewith, e.g., in the form of increasing and decreasing pressure applied at a desired frequency, duty cycle, and amplitude to the internal tissue in contact therewith. As used herein, the frequency is the number of full pressure pulse cycles (peak-to-peak) per unit time; the duty cycle is the percentage of time allocated to the high-pressure segment of a single pressure cycle; and the amplitude is the difference between the maximum and minimum pressure. As the energy imparted by the balloon to the internal tissue is pulsatile, it changes (e.g., increases and decreases) at a defined or determined frequency and duty cycle. During BA treatment, blood flow distal to the distal end balloon may be occluded, which may limit treatment time. To achieve a successful treatment within this time, the pulsatile frequency and amplitude must impart sufficient energy to the tissue to treat it. While the frequency of pulsatile energy imparted by the balloon to tissue associated therewith may vary, in some instances the frequency is high frequency, ranging in some instances from 0 to 100 Hz, such as 0 to 25 Hz. Similarly, the duty cycle of pulsatile energy imparted by the balloon to tissue may vary ranging in some instances from 10% to 100%, such as 60% to 80%. Amplitude of pulsatile energy imparted by the balloon to tissue may vary ranging in some instances from an internal balloon pressure from 0-100 ATM, such as 0-30 ATM. ` described below, during a given procedure, the frequency may vary over the course of the procedure, i.e., not remain constant, as desired.

Pulsatile energy, when exposed to diseased luminal vascular tissue, is effective in treating diseased tissue, such as CP tissue, while reducing the negative effects on surrounding healthy tissue. Important characteristics of pulsatile energy for achieving successful treatments may include the frequency and amplitude of the delivered pulsatile energy. In embodiments, such pulsatile energy can enable the safe, controlled, fatigue fracture of CP-lesions. Fatigue fracture is the process of cyclically loading a structure below the pressure that yields instantaneous failure. Whereas conventional treatments apply dangerous high-pressure bursts to the vessel that may create dissections and perforations, pulsatile angioplasty employs lower pressure high-frequency oscillations in an amplifier balloon to initiate low-pressure fatigue fracture of CP-lesions.

Input Signal Versus Output Signal in a Mechanical System

The described embodiments are dynamic physical systems, in which the output of the system (e.g., actual frequency, duty cycle, and amplitude) is governed by the system input (e.g., desired frequency, duty cycle, and amplitude) and the system characteristics (e.g., catheter length, friction, and flow channel lumen diameter). Embodiments of the systems are configured for generating controlled mechanical lithotripsy pulses in an angioplasty balloon such that the system output tracks, in some instances with minimal attenuation, the commanded, or desired, input signal. Signal attenuation is the reduction in amplitude in the system output versus the input because of the characteristics of the physical system. For successful treatment, minimal attenuation, in that the output pulsatile energy remains substantially similar, e.g., in terms of frequency, duty cycle, and/or amplitude, to the input pulsatile energy as it propagates from the system input (e.g., proximal connector) to the system output (e.g., the distal balloon), is required. As such, in some instances any change in frequency, if present at all, between the proximal connector and distal balloon would be 30% or less, such as 5% or less. In some instances, any change in amplitude, if present at all, of the pulsatile energy between the proximal connector and distal balloon would be 30% or less, such as 5% or less. In some instances, any change in duty cycle, if present at all, of the pulsatile energy between the proximal connector and distal balloon would be 30% or less, such as 5%.

Prior art (e.g., as described in WO 2017/168145 A1; US 2019/0000491 A1; U.S. Pat. No. 6,348,048 B1; WO 2001/010491 A2 and U.S. Pat. No. 8,574,248 B2) in this field has described methods of generating pressure pulses in an angioplasty balloon. However, because of system characteristics, the prior art either is required to proceed at low frequencies to achieve full pressure pulses or suffers from severe attenuation of the signals. In the case of low frequency pressure pulses, the balloon does not generate sufficient pulses in the vessel to achieve any improved treatment outcome. In the case of high frequency pressure pulses, the system output (i.e., the balloon pulse) does not track system inputs and/or the system output is so severely attenuated by the system characteristics that the treatment is ineffective. In other cases, the systems are designed such that the input pressure itself is generated with such high frictional losses (e.g., a piston pump system) that high frequency input pressure pulses are attenuated before being transmitted to the proximal connector.

As summarized above, pulsatile balloon catheter systems, which represents a mechanical system, according to embodiments of the invention include a pulse generator and a balloon catheter assembly operably connected to the pulse generator. The pulse generator of the systems is a component which is configured to generate a first pulsatile energy that can be transduced by the balloon catheter assembly to a second pulsatile energy, e.g., as described in greater detail below. The balloon catheter assembly is configured to receive the first pulsatile energy provided by the pulse generator and transduce it to a second pulsatile energy that may be received by the distal balloon to impart pulsatile energy to an internal tissue location, as described above, such as for use in DBA or lithotripsy applications, e.g., as described in greater detail below, as well as for use in final post-dilatation of the vessel, for example in one treatment comprising both applications. That is, embodiments of the present invention may be used first to apply pressure pulses to luminal tissue, such as a vessel, to crack calcium (i.e., CP-affected tissue) and then to subsequently expand the vessel using traditional, non-compliant balloon post-dilatation, e.g., as described in greater detail below. Embodiments of the pulse generator and the balloon catheter assembly are now reviewed in greater detail.

Pulse Generator

The first pulsatile energy may vary as desired, where examples of first pulsatile energy include, but are not limited to: pulsatile pressure energy, pulsatile mechanical energy, pulsatile electromagnetic energy, and the like. As the first pulsatile energy is pulsatile, the magnitude of the first energy changes or modulates over time, e.g., according to a determined or known, e.g., predetermined, frequency, according to the user, and/or according to treatment progression (as described below). While the frequency of the first pulsatile energy may vary, in some instances the frequency is high frequency, ranging in some instances from a low frequency to a high frequency, such as greater than 0 to 100 Hz, such as 2 to 25 Hz. As described below, during a given procedure, the frequency amplitude and/or duty cycle may vary over the course of the procedure, i.e., not remain constant, as desired (e.g., as described in conjunction with FIG. 6, below). The frequency, amplitude, and/or duty cycle also may vary depending on the type of balloon catheter (e.g., balloon length and/or diameter, shaft length), treatment type, lesion stiffness, etc. The frequency, amplitude, and/or duty cycle also may vary depending on user inputs, negative feedback from measurements, and/or positive feedback from system modeling.

Pulse generators of embodiments of the invention include potential sources configured to provide energy which may be regulated as desired by a regulator and an oscillator to provide for the pulsatile aspect of the first pulsatile energy. Any convenient potential source may be employed, where examples of potential sources include voltage sources, pressure sources, electromagnetic sources, electric field sources, chemical sources, and the like. In some embodiments, the potential source is a pressure source, where examples of suitable pressure sources include, but are not limited to: compressed gas cylinders, compressors, and the like. Where desired, the potential source may be operably coupled to a regulator, which serves to modulate energy to a suitable form so that it may be further acted upon by the oscillator. For example, where the potential source is a high-pressure gas source, e.g., as may be employed in a pneumatic pulse generator, the regulator may serve to regulate the pressure of the gas to a suitable value that can be input to the oscillator. In addition to the potential source and regulator, the pulse generators may include an oscillator. In such instances, the oscillator is used to modulate the magnitude and timing thereof of the potential energy from the potential source to provide for the desired first pulsatile energy.

The disparate components of the pulse generator may be present in a single housing or provided as two or more distinct, operably connected units. In some instances, at least some of the pulse generator components are present in a unit that is configured to be hand-held. In such instances, the hand-held component, e.g., hand-held actuator, is designed to be held and operated in a single adult human hand. While the form factor of such hand-held units may vary as desired, in some instances, such units have a general diameter and/or width ranging from 20 to 150 mm, such as 50 to 80 mm and length ranging from 50 to 300 mm, such as 100 to 200 mm, and a mass ranging from 100 to 2000 g, such as 500 to 750 g. For example, a pulse generator may include a first console component that houses the potential source and regulator, and a second hand-held actuator that includes the oscillator and an actuator for the oscillator, e.g., a manipulatable button. The hand-held actuator may include an electrical connector for providing electrical connection to various components, of the balloon catheter assembly, as desired. For example, the electrical connector may be used to receive data regarding diaphragm position, memory, and/or pressure and to provide power to these sensors, where examples of such are further described below.

In some instances, at least some of the pulse generator components are present in a mountable unit that is configured to be positioned or fixed on the operating table near a patient so that the physician does not need to be physically present to treat the patient. In such instances, the mountable unit is designed to be easily clamped, fixed, or independently stable on the operating table and can be operated by a distant control unit. In such instances, the mountable unit may include a communicator that provides for communication between the unit and the distal control unit, which may be implemented by any desired hardware and/or software configuration, and may be configured to communicate using wired or wireless protocols. Pulse generators employed in systems of the invention may be configured to be reusable or single use, as desired. Pulse generators employed in systems of the invention may be configured to receive a sterile sleeve such that the generator may be used while not contaminating the sterile field of the operating room. Further details regarding pulse generators and components thereof, e.g., potential sources, oscillators, regulators, etc., that may be employed in embodiments of the present invention are provided in United States Published Patent Application Publication No. 20200046949 as well as pending PCT Application Serial No. PCT/US2020/055458; the disclosures of which are herein incorporated by reference.

Balloon Catheter Assembly

As summarized above, in addition to the pulse generator, systems of the invention include a balloon catheter assembly. The balloon catheter assembly is configured to receive first pulsatile energy from the pulse generator and transduce it to a second pulsatile energy that may be propagated along the length of the assembly, e.g., along the fluid, e.g., liquid, passageway thereof, to a distal balloon. As the balloon catheter assembly transduces the first pulsatile energy to a second pulsatile energy, it changes the form of the pulsatile energy in some way. Examples of changes to the form of energy that may be made by the proximal connector include, but are not limited to: gas pressure and/or flow to liquid pressure and/or flow, mechanical potential and/or kinetic energy to fluid pressure and/or flow, optical potential and/or kinetic energy to fluid pressure and/or flow, electric field potential and/or kinetic energy to fluid pressure and/or flow, magnetic potential and/or kinetic energy to fluid pressure and/or flow, and the like. For example, where the first pulsatile energy is a pneumatic first pulsatile energy, the balloon catheter assembly may be configured to transduce the pneumatic first pulsatile energy to a second hydraulic pulsatile energy that may be propagated from the proximal end of the balloon catheter assembly to the distal end of the balloon catheter assembly, which is an example of gas to liquid transduction of the pulsatile energy. In some instances, the balloon catheter assembly propagates the second pulsatile energy from the proximal to distal end with little, if any attenuation, where the magnitude of any attenuation, if present, does not exceed 30% reduction, and in some instances does not exceed 5%, e.g., as described above.

In some instances, the balloon catheter assembly includes: (i) a proximal connector operably connecting the balloon catheter assembly to the pulse generator and configured to transduce a first pulse energy generated by the pulse generator to a second pulse energy; (ii) a distal balloon; and (iii)

a catheter component that includes a fluidic passage operably positioned between the proximal connector and the distal balloon.

The proximal connector is a component of the assembly located proximally in the assembly, e.g., at the proximal end or near the proximal end, e.g., within 1 cm or closer to the proximal end, where the proximal connector is configured to operably connect the assembly to the pulse generator and transduce the first pulsatile energy to the second pulsatile energy, e.g., as described above. The manner in which the proximal connector operably connects to the pulse generator may vary, as desired, where a given type of connector may be a press fit connector, latch connector, screw connector, threaded connector, magnetic connector, push-to-connect connector, Yor-lock connector, claw clamp connector, gasket connector, socket connector, flanged connector, cam-and-groove socket, quick-connect connector and the like, where aligners or detents may be employed, as desired, to provide for a connection that repeatably and accurately positions the proximal connector in relation to the pressure generator and/or electrical connectors.

As reviewed above, in some instances the conversion is fluid to fluid energy conversion, e.g., where the first pulsatile energy is pneumatic pulsatile energy, and the second pulsatile energy is hydraulic pulsatile energy. In such instances, the proximal connector may include a proximal chamber and a distal chamber separated by a membrane, e.g., where the membrane hermetically seals the distal chamber from the proximal chamber. The proximal chamber may be configured to receive pneumatic pulsatile energy from the pulse generator. The volume of the proximal chamber may vary, ranging in some instances from 0.1 mL to 100 mL, such as 1 mL to 4 mL, where in some instances the proximal chamber is occupied by a gas. In certain instances, the proximal chamber forms a minimum volume chamber while still being large enough to accommodate the volume change required to fill a balloon. In this case, the time to fill this minimum volume chamber to a certain pressure is minimized, which allows the frequency of the procedure to be increased. The distal chamber is fluidically coupled to the fluidic passageway of the catheter component. The volume of the distal chamber may vary, ranging in some instances from 0.1 mL to 100 mL, such as 1 mL to 4 mL, where in some instances the distal chamber is occupied by a liquid.

The membrane separating the proximal and distal chambers is configured to move in response to the first pulsatile energy and, in doing so, produces a second pulsatile energy in the distal chamber of the connector. The dimensions of the membrane may vary, where in some instances the membrane has an area ranging from 100 $mm^2$ to 5000 $mm^2$, such as 500 $mm^2$ to 2000 $mm^2$. The membrane may be fabricated from any convenient elastic (e.g., pliant) material, where in some instances the material has a hardness ranging from Shore 10 A to Shore 90 A, such as Shore 50 A, and a thickness between 0.5 mm to 5 mm, such as 1.0 mm to 2.5 mm. Examples of suitable membrane materials include, but are not limited to: silicone, rubber, and the like and in some cases may be strengthened by adding a reinforcing component, such as a braid. Where desired, a biasing component, such as a spring, may be provided to provide for a default or baseline membrane position. For example, a spring may be provided on the distal chamber side of the membrane which urges the membrane back to an initial position when force is removed from the proximal chamber side of the membrane.

While the form of proximal connectors of such embodiments may vary, in some instances the proximal chamber is defined by a proximal flange and the distal chamber is defined by a distal flange, where the proximal and distal flanges are positioned on either side of the membrane to define the proximal and distal chambers, which may be hermetically sealed from each other by the separating membrane. In such instances, the proximal flange may include a proximal port normal to (e.g., axial to) the proximal flange configured to receive the first pulse energy, e.g., pneumatic pulsatile energy, generated by the pulse generator. While the dimensions of the proximal port may vary as desired, in some instances the port has an outer diameter ranging from 1 mm to 30 mm, such as 3 mm to 8 mm and inner diameter ranging from 1 mm to 30 mm, such as 2 mm to 7 mm. In such instances where the proximal flange has a proximal port the port may have a length ranging from 1 mm to 50 mm, such as 3 mm to 10 mm. In such instances, the distal flange may include a distal port fluidically coupling the distal chamber with the fluidic passage of the catheter. While the dimensions of the distal port may vary as desired, in some instances the port has a luminal diameter ranging from 0.1 mm to 10 mm, such as 1 mm to 3 mm.

In instances where the proximal chamber includes a proximal port, the proximal port is fluidically coupled to the port. In such instances, the junction between the proximal port and the proximal chamber may include a nozzle and/or diffuser, which, in some cases, may be formed geometrically by the proximal flange. In such instances, the nozzle or diffuser may act to increase or decrease velocity of the flow at the expense of fluid pressure. With such increase or decrease of velocity of the flow, characteristics of the energy conversion may be improved, such as ramp up time or smoothness of energy conversion. In cases of pneumatic flow, the speed of the gas may be high enough to induce compressible fluid phenomena such as in sonic or supersonic flows. In such cases, specialized flow nozzles such as a convergent-divergent nozzle may be used to optimize flow velocity.

Where desired, the proximal connector may include one or more sensors, e.g., configured to provide data regarding one or more components of the connector and/or the balloon catheter assembly. Any convenient type of sensor may be included in the proximal connector, where sensors of interest include, but are not limited to: pressure sensors, positional sensors, displacement sensors, proximity sensors, flow sensors, temperature sensors and the like. In some instances, the proximal connector includes a pressure sensor operably coupled to the distal chamber. In such instances, the pressure sensor may detect pressure and changes thereof in the liquid in the distal chamber. When included, any convenient type of pressure sensor may be present, where examples of pressure sensors that may be present include, but are not limited to: resistive, capacitive, piezoelectric, optical, and MEMS-based pressure sensors, and the like. In some instances, the proximal connector includes a membrane positional sensor configured to provide spatial data regarding the position of the membrane at a given time, e.g., during use of the system. When present, any convenient membrane position sensor may be employed. In some instances, the membrane positional sensor is a Hall sensor, e.g., which may be employed in conjunction with a magnet (e.g., permanent or electromagnet) present at a fixed location relative to the membrane, such as a fixed location of the proximal connector or the pulse generator (e.g., hand-held actuator), etc., such that the fixed magnet is positioned to modulate voltage of the Hall Sensor upon membrane movement. In other instances, the membrane positional sensor may be an optical sensor, electric field potential sensor, resistive sensor, magnetic sensor, angle sensor, or acceleration sensor. Further, any combination of these sensors may be used to gather positional data of the membrane or diaphragm. In cases in which a combination of membrane positional sensors is employed, e.g., to ensure sensors provide correct data across a variety of frequencies, sensor data may be combined through "sensor fusion" techniques, such as those known in the art. When present, a membrane positional sensor may be employed for a variety of different purposes, e.g., to assess vessel compliance and treatment (such as described below), to assess proper filling of the balloon catheter assembly, to provide for a way to assess whether the membrane has been stretched beyond desired thresholds, etc. Fabrication methods of the membrane sensor may include, but are not limited to: adhesives, direct printing, welding, embedding and the like.

Where desired, the proximal connector may further include an electrical assembly. The electrical assembly may be configured to perform a number of functions, such as but not limited to, powering of one or more sensors, control of one or more sensors, storage of data obtained from one or more sensors, transmission of sensor data from one or more sensors to another location, storage of information about the balloon catheter assembly, writing and/or reading data and the like. The electrical assembly may vary, and in some instances may include circuitry and/or memory. When present, the memory may store a variety of different types of information, including but not limited to: information about the balloon catheter assembly and/or components thereof, e.g., the distal balloon, e.g., expiration date, batch number, balloon size (e.g., balloon diameter and length), balloon rated burst and nominal pressure, cycle limit (e.g., number of allowable cycles the balloon is rated for), and cycles used for, allowable pulse frequency or duration, previous use, balloon reference pressure-volume curve, and/or indication for use, etc. The electrical assembly, when present, may further include a connector, e.g., for operably connecting the electrical assembly to the pulse generator. The electrical assembly may be present in any convenient configuration, such as a printed circuit board, including a flexible printed circuit board. In some cases, the sensors may transmit data wirelessly, such as through Bluetooth RF.

The various components of the proximal connector, e.g., as described above, may be present in a housing or overmold, e.g., configured to protect the proximal connector components e.g., during an accidental fall or during packaging. The housing, if present, may be fabricated from a suitably rigid material, e.g., polymeric material, and may be transparent or opaque, as desired.

As summarized above, the balloon catheter assembly may include a catheter component positioned between the proximal connector and the distal balloon. The catheter component is configured to propagate or convey the second pulsatile energy from the proximal connector to the distal balloon, e.g., with minimal, if any, attenuation, such as described above. The catheter component includes a portion, e.g., a shaft, that is configured to be employed as a catheter, such that it may be introduced into a lumen of a human or another animal, e.g., mammal. While the dimensions of this portion may vary, in some instances this catheter portion has an outer diameter (OD) ranging from 1.50 mm to 2.50 mm, such as 1.75 mm to 2.20 mm.

While the structure of the catheter component may vary, in some instances the catheter component includes a proximal flexible tube; a distal catheter shaft (which is the catheter portion, e.g., as described above); and a connector connecting the distal end of the proximal flexible tube to the proximal end of the distal catheter shaft. The proximal flexible tube is made of a pliant material, e.g., braided or unbraided polyvinyl chloride (PVC), silicone, polycarbonate (PC), and the like, where the dimensions of the tube may vary. In some instances, the flexible tube has an inner lumen with a diameter ranging from 0.1 mm to 10 mm, such as 1 mm to 3 mm, and a wall thickness ranging from 0.1 mm to 5 mm, such as 0.5 mm to 2 mm. The length of the proximal flexible tube may also vary, ranging in some instances from 1 cm to 100 cm, such as 5 cm to 20 cm.

The distal catheter shaft may also vary. The distal catheter shaft may be fabricated from any suitable physiologically acceptable material, including but not limited to a polyimide, such as a polyimide braid, or a polyimide-type material and the like. In some instances, the distal catheter shaft has a length ranging from 10 cm to 1 m, such as 100 cm to 300 cm. The outer diameter of the distal catheter shaft may also vary, in some instances ranging from 1.50 to 2.50, such as 1.75 mm to 2.20 mm. The distal catheter shaft may include a first liquid passageway lumen, where the dimensions of this first liquid passageway lumen may vary. In some instances, the diameter of this first liquid passageway lumen ranges from 1.3 to 2.2 mm, such as 1.6 to 2.1 mm. The first liquid passageway may include on or more openings at the distal end for establishing liquid communication between the interior of the liquid passageway lumen and the interior of the distal balloon. The one or more openings, when present, are configured so as to not substantially attenuate, and in some instances, not attenuate at all, the second pulsatile energy as it enters the balloon from the liquid passageway. In some instances, these openings may be configured to be a nozzle and/or diffuser. In such instances, the nozzle or diffuser may act to increase or decrease velocity of the flow at the expense of fluid pressure. With such increase or decrease of velocity of the flow, characteristics of the balloon expansion may be altered, such as ramp up time, impact, force, and the like. The distal catheter shaft may also include a second guidewire lumen. When present, the dimensions of this second guidewire lumen may vary, where in some instances the diameter of the guidewire lumen ranges from 0.25 to 0.5 mm, such as 0.37 to 0.42 mm.

Also present in the catheter component of these embodiments is a connector connecting the distal end of the proximal flexible tube to the proximal end of the distal catheter shaft. The connector may vary as desired. In some instances, the connector includes a first branch configured to provide guidewire access to a guidewire channel of the catheter shaft and a second branch configured to fluidically couple the lumen of the proximal flexible tube and liquid passageway lumen of the distal catheter shaft. An example of a suitable connector is a Y connector.

In some embodiments, a fluidic passage of a catheter is configured to receive energy transduced from one or more connectors. For example, a single fluidic passage of a catheter may be configured to receive energy from two or more proximal connectors, each operably connected to the single fluidic passage, such that the fluidic passage receives pulse energy transduced by each connector. In another example, a fluidic passage of a catheter may be configured to receive energy from each of a connector that is a barrel syringe connector (i.e., a connector that is configured substantially as a barrel syringe, such as a barrel syringe connector comprising a pneumatic input port, a fluid output port, a plunger (i.e., a piston), a pneumatic chamber and a fluid chamber) as well as another proximal connector, as described herein. In such an embodiment, the barrel syringe and proximal connector may be configured to work synchronously to prime the fluidic passage and generate pulsatile energy. In such embodiment, the barrel syringe may be used to prime the system, i.e., apply a baseline pressure to fluid present in the fluidic passage, and the proximal connector is subsequently used to provide pulsatile energy to the fluid present in the fluidic passage at the baseline pressure. In embodiments, a fluidic passage may be connected to one or more connectors, such as one, two, three, four, five, six, seven, eight, nine, ten, 20, 50 or 100 or more connectors. Such connectors, each connected to a single fluidic passage, may be of the same type (e.g., proximal connectors, as described herein) and/or configuration or may differ in any relevant respect. Multiple connectors attached to a single fluidic passage may be synchronized or otherwise configured to transduce energy to the fluidic passage in any convenient manner. In other cases, the output of a single connector may be operably connected to a plurality of fluidic passages. For example, in an embodiment, the output of a single proximal connector may be operably connected to multiple fluidic passages, such that the proximal connector may be used to transmit pulse energy to each of the plurality of fluidic passages. In another exemplary embodiment, the output of a single barrel syringe connector may be operably connected to multiple fluidic passages, such that the barrel syringe connector may be used to prime fluid present in each of the plurality of fluidic passages. That is, the barrel syringe connector may be configured to apply a baseline pressure to fluid present in each of the plurality of fluidic passages, and because one barrel syringe is operably connected to multiple fluidic passages, each of the fluidic passages is primed simultaneously. In embodiments, a connector may be operably connected to multiple fluidic passages of a single catheter or more than one catheter. Further details regarding embodiments comprising a barrel syringe are described in U.S. Application Ser. No. 63/346,703 filed on May 27, 2022; the disclosure of which is incorporated herein by reference.

As described above, barrel syringe connectors of interest may include a pneumatic input port, a fluid output port, a plunger, a pneumatic chamber and a fluid chamber. In certain instances, the plunger (i.e., piston) of the barrel syringe may be connected to a biasing spring, which would enable the quick return of the piston to its original state. In this condition, some or all the fluid volume would be removed from a fluidly coupled distal balloon. In other embodiments, a barrel syringe-type connector is selectively connected to a vacuum (i.e., the proximal side of the connector), which would facilitate evacuation of the proximal side of the barrel syringe, such that the piston of the barrel syringe-type connector would return to an original position, i.e., an equilibrium position. In embodiments of such connectors, a fluidly coupled distal balloon positioned at a distal region of the catheter could be inflated or deflated rapidly. Embodiments of such connectors could have a variety of sensors monitoring the state of the connector and distal balloon fluidically coupled thereto, such as pressure sensors, volume sensors or the like.

As reviewed above, the balloon catheter assembly further includes a distal balloon. Any convenient balloon may be employed. Suitable balloons include, but are not limited to, standard angioplasty balloons, such as compliant and non-compliant angioplasty balloons. In one embodiment, the balloon is a composite balloon that includes two distinct layers, which layers include a non-compliant layer and compliant layer. To describe the improvements of the current composite balloon structure over the prior art, the two layers of the composite balloon as individual units will be described. Non-compliant angioplasty balloons are commonly used, and, in some cases, semi-compliant balloons are used, in percutaneous procedures because the set diameter of the balloon distributes its force equally to the surrounding vessel without bulging into the less stiff, healthy tissue surrounding a stenosis. When the non-compliant balloon material is pressurized, the balloon first fills, which yields a low pressure and high stretch state. When the non-compliant balloon reaches its nominal diameter, balloon pressure increases significantly for a correspondingly low stretch. When pressure is released in the balloon, the balloon remains at its nominal stretch because of the lack of elasticity in the balloon. This lack of elasticity is problematic for three reasons: (1) unless vacuum is generated, a de-pressurized balloon can remain filled, which can occlude blood flow, (2) it can lead to difficulty in removing the balloon catheter through the sheath after treatment, and (3) during pulsatile treatment, the balloon does not force fluid out during the low-pressure phase, which prevents the required stress relaxation in the surrounding tissues. Therefore, non-compliant balloons are useful at high pressures but have limitations at lower pressures. Compliant angioplasty balloons typically have a linear pressure-stretch curve. The use of these balloons is limited in percutaneous procedures because the balloon stretches non-uniformly around hardened segments of an artery, which may cause damage to the healthy, soft tissues surrounding the hardened diseased tissues. With a compliant balloon, there is typically a linear increase in balloon pressure. Compared to non-compliant balloons, compliant balloons have a "short" initial fill region, and therefore, when the pressure in the balloon is released, the balloon returns to its initial stretch state without requiring additional vacuum. This return to its initial state benefits the procedure because, upon return to the initial stretch state, blood flow is immediately restored, and the balloon can be more easily retracted through the sheath. Further, during pulsatile angioplasty, the compliance of the balloon serves as the impetus for forcing fluid out of the balloon, which is required to allow the surrounding tissue to relax with low stress during the low-pressure phases. Therefore, compliant balloons are helpful at lower pressures but are limited in their ability to treat at high pressures. Alone, non-compliant and compliant angioplasty balloons are not optimal for the various stages of pulsatile and standard percutaneous angioplasty. Together as a composite, though, they can meet important needs of both treatments. In one embodiment of the composite angioplasty balloon, a non-compliant balloon is covered with a compliant sleeve to achieve an "arrowed" pressure-stretch, e.g., as further described in pending PCT application serial no. PCT/US2020/055458; the disclosure of which is herein incorporated by reference. The compliant layer may be a rubber, silicone, polyurethane, or nitinol material or another material that can stretch up to 100-500% before failure, can withstand thousands of cycles before failure, and encounters minimal, if any, plastic deformation during expansion. During use, the exemplary composite balloon follows an arrowed response. During the low-pressure phase, the compliant material dominates the response. The composite balloon follows the compliant material curve until the balloon stretch intersects with the non-compliant balloon stretch. At this intersection and higher pressures, the non-compliant material dominates the balloon response. Immediately upon pressure release, the balloon returns along the arrowed response to the initial, or zero, stretch state. This exemplary composite balloon has the low-pressure benefits of compliant angioplasty balloons and the high-pressure benefits of non-compliant angioplasty balloons. Other benefits include self-folding and deflating of the balloon, tear and pin-hole mitigation, increased oscillation frequency during pulsatile angioplasty, and increased pushability of the balloon while crossing a lesion. Further details regarding composite angioplasty balloons finding use in embodiments of the invention may be found in pending PCT application serial no. PCT/US2020/055458; the disclosure of which is herein incorporated by reference.

The balloon catheter assembly may or may not be a "sealed" component. In some instances, the balloon catheter assembly is not sealed, such that a fluid, e.g., liquid, may be introduced into the liquid passageway(s) of the assembly at the time of use and/or gas may be removed from the assembly (e.g., via de-bubbling). In yet other instances, the balloon catheter assembly is a sealed or closed assembly, such that the liquid passageways and balloon are pre-filled with a liquid prior to use, and the liquid is sealed in the assembly. In either instance, the liquid that is introduced into the lumen(s) and balloon of the assembly may vary, where in some instances the liquid is saline. Where desired, the liquid may include a suitable contrast agent, where examples of contrast agents include, but are not limited to radiocontrast agents, such as but not limited to, iodine contrast agents, barium contrast agents, etc.

In some instances, the above embodiments may be configured such that the procedure may be performed completely autonomously and/or remotely. In these cases, the balloon catheter may be inserted into the patient manually or using a robotic catheterization system (as described in published application WO 2010/025338, the disclosure of which is herein incorporated by reference). With this system, equipment such as guidewires and balloon catheter can be advanced to the site of the lesion, and, once at the lesion, the balloon may be inflated or deflated. With the embodiments described above, the balloon may be pre-filled with fluid so that the user does not have to fill the balloon prior to pressurization. In other instances, the composite balloon embodiment may be used to ensure that the balloon deflates and wraps post-procedure so it may be easily removed. In such instances, the operator may be situated at a console to control the procedure including the pressure, frequency, and/or duty cycle. At the same time, the operator may be able see X-ray imaging at the same time to visualize the inflated balloon and procedural efficacy. In some instances, feedback, e.g., visual, audio, feel and the like, may be provided to the operator to indicate procedural characteristics such as volume and/or pressure change in the balloon, frequency, duty cycle, balloon expansion, balloon position and the like.

The balloon catheter assembly may be configured for single or one-time use, such that it is disposable. Prior to use, the balloon catheter assembly may be sterile, as desired.

Various aspects of the invention being generally described above, elements of the invention are now further reviewed in the context of specific embodiments.

Specific Embodiment

A system in accordance with embodiment of the invention for generating high frequency angioplasty balloon oscillations is schematically illustrated in FIG. 1. In some instances, the system can include a pulse generator which has a potential energy source, such as a high voltage or pressure source, a switching system, e.g., for controlling the high potential source, etc., and a balloon catheter assembly for converting the output of the pulse generator (i.e., first pulsatile energy), into hydraulic oscillations (i.e., second pulsatile energy) of an angioplasty balloon. In embodiments, the potential energy source acts to drive the balloon angioplasty oscillations, a switching system controls the frequency, duty cycle, and/or amplitude of the outputted energy from the pulse generator, a proximal connector of the balloon catheter assembly converts the outputted energy into hydraulic oscillations that thereby generate oscillations in an angioplasty balloon catheter, and the high flow balloon catheter allows the pressure oscillation inputs to the system to be achieved and optimized at the balloon output. Variations of this system are provided in each of the embodiments below. The following embodiments are not meant to be an exhaustive list but are meant to provide examples of various configurations of the overall system.

In some embodiments as illustrated schematically in FIG. 1, the system includes two components: a pulse generator 70 (to the left of the dashed line), which may be configured to be reusable; and a balloon catheter assembly 1 (to the right of the of the dashed line), which may be configured to be used a single time (e.g., such that it is disposable). The terms "reusable" and "disposable" as employed here and elsewhere throughout the description are used for convenience in describing an embodiment of the invention illustrated in FIG. 1. However, the invention is not so limited. As such, any part of the device may be configured for one time use or for use multiple times, as desired. In the embodiment illustrated in FIG. 1, the pulse generator 70 includes the potential source 870, a potential regulator 880, and a controller 72. The pulse generator also includes a switch or oscillator (such as a solenoid) 14, which may be a present in a hand-held component or actuator of the pulse generator, as desired. Also illustrated is the balloon catheter assembly 1 which includes a proximal connector 400 that includes a membrane 30, a pressure and/or flow transducer 31, an electrical connector 13, a high-flow catheter 16 and balloon 2. Inputs to the pulse generator 70 can include feedback from sensors, such as a pressure or flow transducer 31 or from user inputs such as buttons or switches. The output from the pulse generator 70 may include power, logic, and/or regulated 880 or un-regulated potential energy 870, such as that from high-pressure fluid or voltage in the form of first pulsatile energy and is transmitted to the balloon catheter assembly 1. The balloon catheter assembly 1 converts the first pulsatile energy output to hydraulic oscillations in the fluid communication path 35, which are output to the high-flow catheter 16 and balloon 2.

Figure 2:
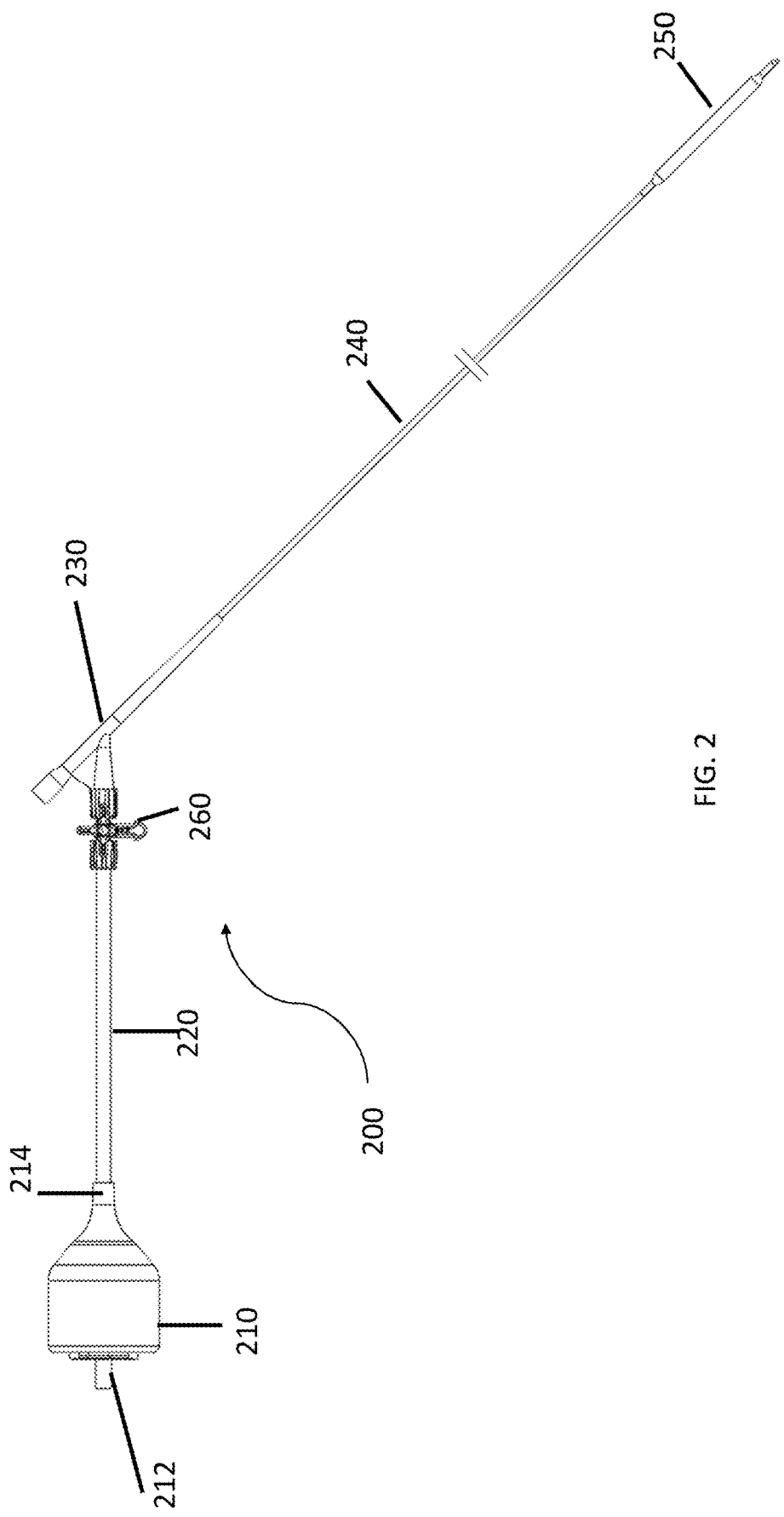
FIG. 2 provides a view of a catheter balloon assembly according to an embodiment of the invention.

FIG. 2 provides an illustration of a balloon catheter assembly 200 according to an embodiment of the invention, e.g., that may be used in a system as schematically illustrated in FIG. 1. Balloon catheter assembly 200 includes proximal connector 210 having a proximal port 212 for operably connecting to a pneumatic output of a pulse generator (not shown), a proximal flexible tube 220 coupled to a distal port 214 of the proximal connector; a distal catheter shaft 240 having an angioplasty balloon, such as a composite balloon 250 located at a distal end thereof; and a Y-connector 230 connecting the distal end of the proximal flexible tube 220 to the proximal end of the distal catheter shaft 240. Also shown is optional valve 260 positioned between the distal end of the proximal flexible tube 220 and the Y-connector 230. When present, the proximal flexible tube 220 acts a strain relief between the proximal connector 210 and the Y-connector 230, distal catheter shaft 240, and angioplasty balloon 250. When present, valve 260 may be employed to introduce fluid into the liquid passageways of the balloon catheter assembly. In some instances, valve 260 is not present. For example, as described above, the balloon catheter assembly may be a closed or sealed system that is provided to a user prefilled, e.g., with a suitable contrast agent containing liquid. In such instances, the valve 260 may not be provided since fluid priming is not required to use the assembly in the system of the invention.

FIGS. 3A to 3D provide different views of a proximal connector of a balloon catheter assembly in accordance with embodiments of the invention. FIG. 3A provides a cutaway side illustration of proximal connector 300. Proximal connector 300 includes proximal flange 310 and distal flange 350 separated by membrane 330. Proximal flange 310 defines proximal chamber 315 which is accessed by proximal port 320. Distal flange 350 defines distal chamber 355 which is accessed by distal port 360. Pressure transducer 325 is operably coupled to distal port 360 and distal chamber 355. The proximal and distal flanges 310,350 are held together by screws, as illustrated by screw 370. Alternatively, the flanges can be fixed via any other appropriate assembly method such as an adhesive, weld, or other means. In other instances, the flanges can be fabricated as a single component via a multi-stage injection molding or over-molding process around the flexible membrane and electronics. Also shown is Hall sensor 335, permanent magnet 448 (which may also be located in the handheld actuator 400, electrical connector 390, and flexible printed circuit board 397. The threaded portion 398 at the distal end of the distal port serves as the interface between the proximal flexible tube and the distal flange. FIG. 3B provides an end view of proximal flange 310 of proximal connector 300. As seen in FIG. 3B, screws 370 are positioned circumferentially around the flange to provide connection to the distal flange (not shown). Also shown is proximal port 320 and electrical connector 390, which provides for operable electrical connection to the pulse generator (not shown). FIG. 3C shows an outer side view of the proximal connector 300, showing the proximal and distal flanges 310,350 joined together by screws 370. Also shown is memory 395, which is electrically coupled to a flexible printed circuit board 397 which is electrically coupled to electrical connector 390. Similarly, pressure sensor 325 is electrically coupled to the flexible printed circuit board 397. FIG. 3D shows a perspective view of proximal connector 300. FIG. 3E provides a view of the proximal connector 300 with over-mold 380 which is fabricated from a rigid, opaque material that serves to protect the various components, e.g., circuitry, sensors, etc., of the proximal connector. The proximal connector may have diameter and width variations to accommodate different balloon types while still being able to be connected to a common hand-held actuator. For example, for peripheral or coronary balloons, the proximal connector may have dimensions to accommodate a volume change between 1-20 ml. For larger balloons such as valvuloplasty balloons, the proximal connector can be enlarged to accommodate a volume change up to 50 mL-100 mL.

The flexible printed circuit board, 397, which connects various sensors on the assembly to the proximal flange to allow connection to the handle, regardless of the size of the proximal connector, is further illustrated in FIGS. 3F to 3H, which provide front, back, and isometric views of flexible printed circuit board 397. This embodiment allows for the size of the proximal connector to change (e.g., as described above) with only an increase in length of the flexible PCB and not a complete redesign of the electronics. $L_{prox}$ of the flexible printed circuit board is the length required between the electrical connector 390 and the bend to the diaphragm for the Hall sensor 335. $L_{Distal}$ is the length from the electrical connector 390 to the pressure transducer 325. These two lengths can be adjusted to accommodate changes in the size of the proximal connector. Also shown is memory 395.

FIGS. 4A to 4C provide different views of a hand-held component, which may be referred to as an actuator, of pulse generator according to embodiments of the invention. FIG. 4A provides a side view of hand-held actuator 400, which is configured to be held in a hand of an adult human and includes a gripping region 410, a distal connector 420, proximal strain relief region 405, pulse generator connector 406, and actuator button 430. Gripping region 410 may be configured to be easily gripped by adjusting the geometry to fit the human hand, by using a soft plastic (e.g., rubber, silicone, thermoplastic elastomer (TPE)) over-mold, or the like.

FIG. 4B provides an end on view of the connector 420 of actuator 400. As seen in FIG. 4B, connector 420 includes electrical connector 430 and pneumatic connector 440 for establishing connection with the proximal port of the proximal connector (not shown). The connector 420 also includes a detent to ensure appropriate, reliable, and repeatable connection of the proximal connector. To release the proximal port of the proximal connector 300 from the pneumatic connector 440, a release plate 445 with release buttons 446 may be used.

FIG. 4C provides a cutaway view of actuator 400. Within actuator 400, an electromagnetic 3/2-way solenoid 470 may be used. The solenoid 470 includes a pressure inlet port 471, outlet port 472, electromagnetic coil 473, valve poppet and spring assembly 474, and exhaust port 475. The actuator may have added space for an electronic passageway or printed circuit board 485 and pneumatic passageway 486. Further, in some instances, a permanent magnet 448 may be situated in the connector 420 of the actuator 400 for inducing a voltage and/or current in the Hall effect sensor, which is attached to the membrane of the proximal connector (not shown). This electromagnet may also be located in the proximal connector. The 3/2-way solenoid 470 operates in two states—an ON and OFF state. During the ON state, the valve poppet and spring assembly 474 is actuated by energizing the electromagnetic coil 473 allowing high-pressure flow from the inlet 471 to proceed to the outlet 472 and the proximal connector (not shown) to pressurize the balloon. In the OFF state, the electromagnetic coil 473 is de-energized, and the valve poppet and spring assembly 474 is closed allowing the pressurized fluid from the proximal connector (not shown) to be exhausted through the inlet 472 to the exhaust port 475. To reduce noise, a noise reducer (not shown) at the exhaust port 475 may be used. Various electrical connectors may be used to transport signal and power to and from the pulse generator console (not shown) to the electrical contacts 430, actuator button 430, and electromagnetic coil 486 and may be located in region 485. Pneumatic connections may be transported and connected in the pneumatic connector region 486. FIG. 4D provides an overhead view of actuator button 430. Actuator button 430 may be a membrane-type switch or any similar type of button configuration, such as known in the art. The switch may by impenetrable to liquids or cleaning solutions. In some instances, the actuator button 430 may include an ON/OFF switch 490, ON/OFF LED configuration 491, control manipulator buttons 492, and control manipulator LEDs, 493.

FIGS. 4E and 4F provide exploded and assembled views, respectively, of an actuator 400 coupled to a proximal end connector 300 via connector 420. Electrical connector 430 may be spring loaded to account for any tolerance differences or movement generated during the repeated connection and disconnection of the proximal connector.

Model

A mathematical model of the oscillating system is described below. This model has several purposes including for controlling the system in real-time (e.g., for a state-space controller). The mathematical model describes the system of FIG. 1 where a high potential source is converted to fluid pressure oscillations in the catheter and to the balloon. The input oscillations may be modelled as instantaneous step inputs of pressure, $P_{input}$. The oscillations flow along a catheter with radius $2r$ and length 1 to the angioplasty balloon. The fluid responds rapidly to the step input, but as the balloon pressurizes, the fluid pressure gradient decays to equilibrium with the input step pressure. The volume-pressure relationship of the balloon determines the corresponding pressure generated in the balloon for a given volume and balloon stretch. After the step input, the pressure gradient is treated as quasi-static and independent of time for small time steps. The flow through the lumen of the catheter is modeled using the Navier-Stokes equation for pipe flow:

$$\rho\left(\frac{\partial v_z}{\partial t} + v_r\frac{\partial v_z}{\partial r} + \frac{v_\theta}{r}\frac{\partial v_z}{\partial \theta} + v_z\frac{\partial v_z}{\partial z}\right) = \\ -\frac{dP}{dz} + \rho G_z + \mu\left[\frac{1}{r}\frac{\partial}{\partial r}\left(r\frac{\partial v_z}{\partial r}\right) + \frac{1}{r^2}\frac{\partial^2 v_z}{\partial \theta^2} + \frac{\partial^2 v_z}{\partial z}\right] \quad (1)$$

where system parameters are identified in Table 1.

The tube is assumed to be rigid, resulting in unidirectional flow ($v_r = v_\theta = 0$). The contrast mixture is modeled as an incompressible fluid, so that $$\nabla \cdot \vec{v} = \frac{\partial v_z}{\partial z} + \frac{\partial v_r}{\partial r} + \frac{\partial v_\theta}{\partial \theta} = 0.$$

Gravitational effects are neglected. The pressure gradient is treated as quasi-static for small time steps, $$\frac{\partial}{\partial f}\left(\frac{dP}{dz}\right) = \frac{dP}{dz}.$$

Applying these assumptions reduces equation (1) to:

$$\rho\frac{\partial v_z}{\partial t} = -\frac{dP}{dz} + \mu\left[\frac{1}{r}\frac{\partial}{\partial r}\left(r\frac{\partial v_z}{\partial r}\right)\right] \quad (2)$$

TABLE I

DEFINITIONS AND VALUES

| Symbol | Quantity | Units/Value |
|---|---|---|
| P | Pressure | Pa |
| v | Velocity | m/s |
| ρ | Density | 1100 kg/m³ |
| μ | Viscosity | 1.3E-3 Pa*s |
| $G_z$ | Acceleration due to gravity | 9.81 m/s² |
| R | Outer radius of catheter shaft | 0.8 mm |
| φ | Dimensionless velocity | — |
| ξ | Dimensionless radial position | — |
| τ | Dimensionless time | — |

The dimensionless parameters include dimensionless radial position ξ:

$$\xi = \frac{r}{R} \quad (3)$$

$$v_z = -\frac{R^2}{4\mu}\frac{dP}{dz}\varphi(\xi)\tau = \frac{\mu t}{\rho R^2}$$

where r is a radius of the tube, the z-direction velocity $v_z$ is:

$$v_z = -\frac{R^2}{4\mu}\frac{dP}{dz}\varphi(\xi) \quad (4)$$

where $$\frac{dP}{dz}$$

is the pressure gradient along the tube and $\varphi(\xi)$ is dimensionless velocity along the radius of the tube, and dimensionless time is τ:

$$\tau = \frac{\mu t}{\rho R^2} \quad (5)$$

Thus equation (2) becomes $$\frac{\partial \varphi}{\partial \tau} = 4 + \frac{1}{\xi}\frac{\partial}{\partial \xi}\left(\xi\frac{\partial \varphi}{\partial \xi}\right) \quad (6)$$

Letting $$\varphi = 1 - \xi^2 - \Psi \quad (6)$$

so that the no slip boundary condition is $\Psi = 1 - \xi^2$ at $\tau = 0$. Solving (3) by separation of variables gives $$\Psi = \sum_n A_n e^{-\alpha_n^2 \tau} J_0(\alpha_n \xi) \quad (6)$$

where $J_0$ is the Bessel function of zeroth order and first type, and $\alpha_n$ are its zeros. If the fluid is initially at rest ($\varphi = 0$ at $\tau = 1$), then $$A_n = \frac{8}{\alpha_n^3 J_1(\alpha_n)} \quad (6)$$

The velocity profile is then defined $$v_z = \frac{1}{4\mu}\frac{dP}{dz}R^2\left[\xi^2 - 1 + 8\sum_n \frac{J_0(\alpha_n \xi)}{\alpha_n^3 J_1(\alpha_n)}e^{-\alpha_n^2 \tau}\right] \quad (6)$$

and the volumetric flow rate is $$Q = \pi R^2 \bar{v}_z \quad (6)$$

If the fluid is instead at some fully developed velocity with an average velocity $\bar{v}_{z0}$, then the initial condition is modified $\varphi=\bar{v}_z$ at $\tau=0$, or $\Psi=1-\xi^2-\bar{v}_{z0}$. Now, $$A_n = \frac{2\alpha^2 \bar{v}_{z0} + 8}{\alpha_n^3 J_1(\alpha_n)} \quad (6)$$

For a coaxial catheter shaft, the volumetric flow rate is modified with a scale factor to account for additional frictional losses at the inner wall, where $k=R_i/R$ (Papanastasiu, 1999).

$$Q = \pi R^2 \bar{v}_z \left[ (1-k^4) - \frac{(1-k^2)^2}{\ln(1/k)} \right] \quad (6)$$

To use this model for real-time control or procedural planning, system parameters are identified. System parameters of this model include step input characteristics, balloon dimensions, catheter construction and dimensions, pressure-volume relationship of the balloon, and the like.

Step input characteristics are system dependent and can be measured (e.g., during the manufacturing process) and built into the system. Likewise, with various sensor measurements built into the system, the system, in certain embodiments, may be able to measure the step input response generated by the pressure generator.

In certain embodiments, balloon dimensions and catheter construction and dimensions can be pre-loaded onto the balloon catheter memory. These dimensions include balloon length, diameter, shape, and the like. Catheter construction and dimensions include details such as the shape of the cross-section of the catheter lumen (e.g., co-axial, co-extrusion, etc.) and catheter length, outer diameter, inner diameter, ratio of flow channel area to guidewire channel area, and the like. In certain embodiments, the pressure-volume relationship of the balloon can be measured and pre-loaded onto the balloon catheter memory. An example of a pressure-volume relationship for an unrestrained 4 mm diameter×20 mm length balloon is shown in FIG. 5.

Figure 6:
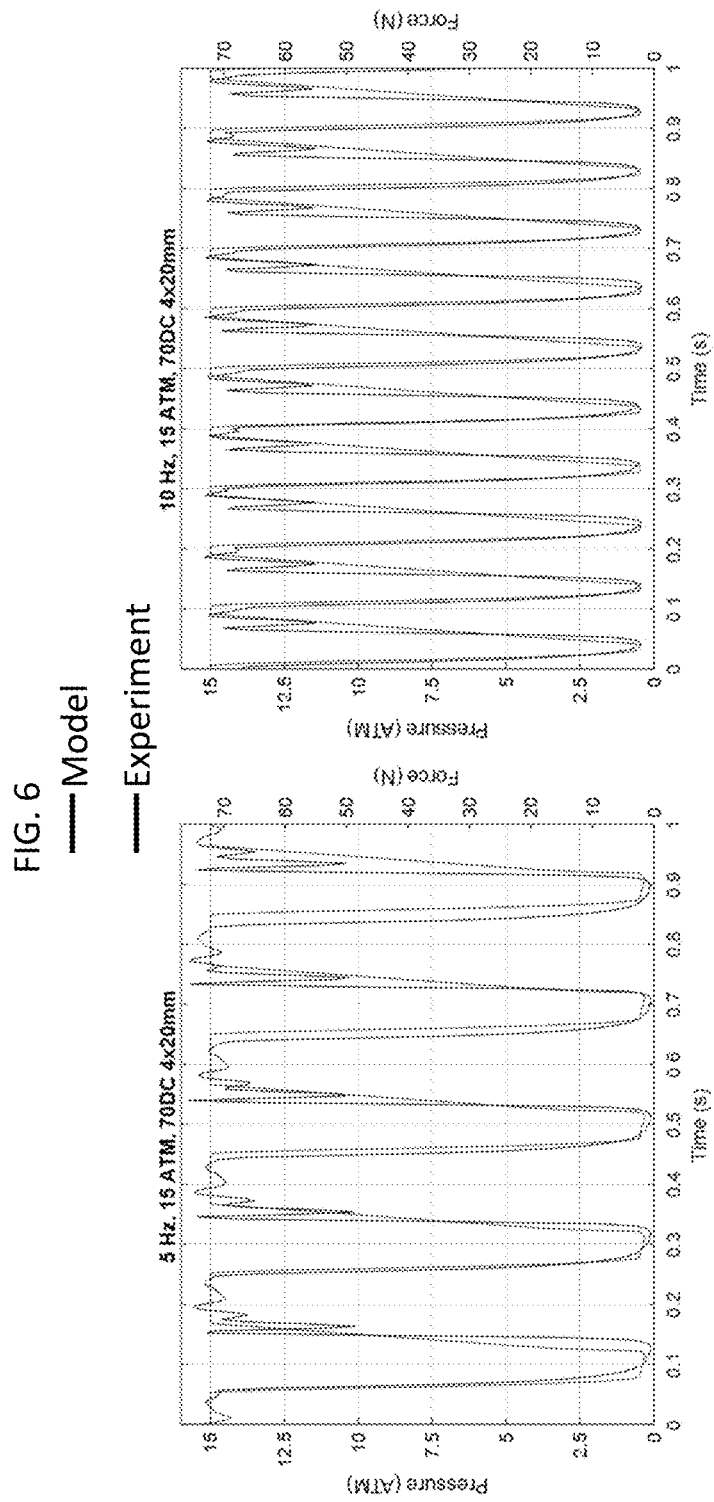
FIG. 6 provides two examples of the experimentally measured pressure in the balloon and force output from the balloon of FIG. 5.

Using these measured system characteristics and the model derived above, the system may be controlled in real time (e.g., using negative feedback control and/or feedforward control) to ensure pressure amplitude, duty cycle, and frequency are appropriately set during the procedure. Two examples of the experimentally measured pressure in the balloon and force output from the balloon is shown in FIG. 6. The model, as derived above, predicts the experimental measurements accurately. With such a predictive model and with feedback from system measurements, procedural characteristics (frequency, pressure input, and duty cycle) can be adjusted to ensure maximized treatment effect.

Figure 5:
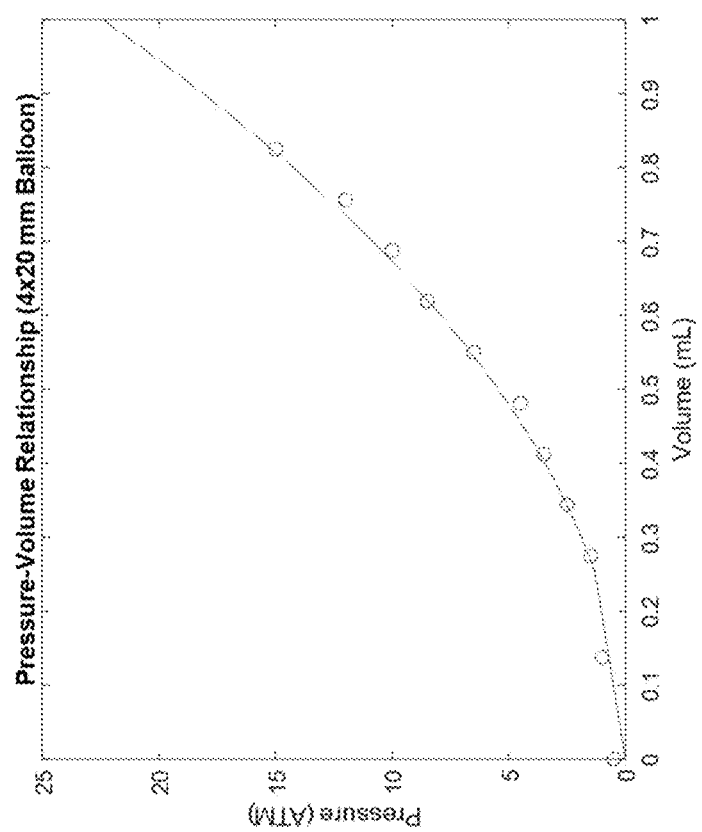
FIG. 5 provides an example of a pressure-volume relationship for an unrestrained 4 mm diameter×20 mm length balloon.
Figure 7A:
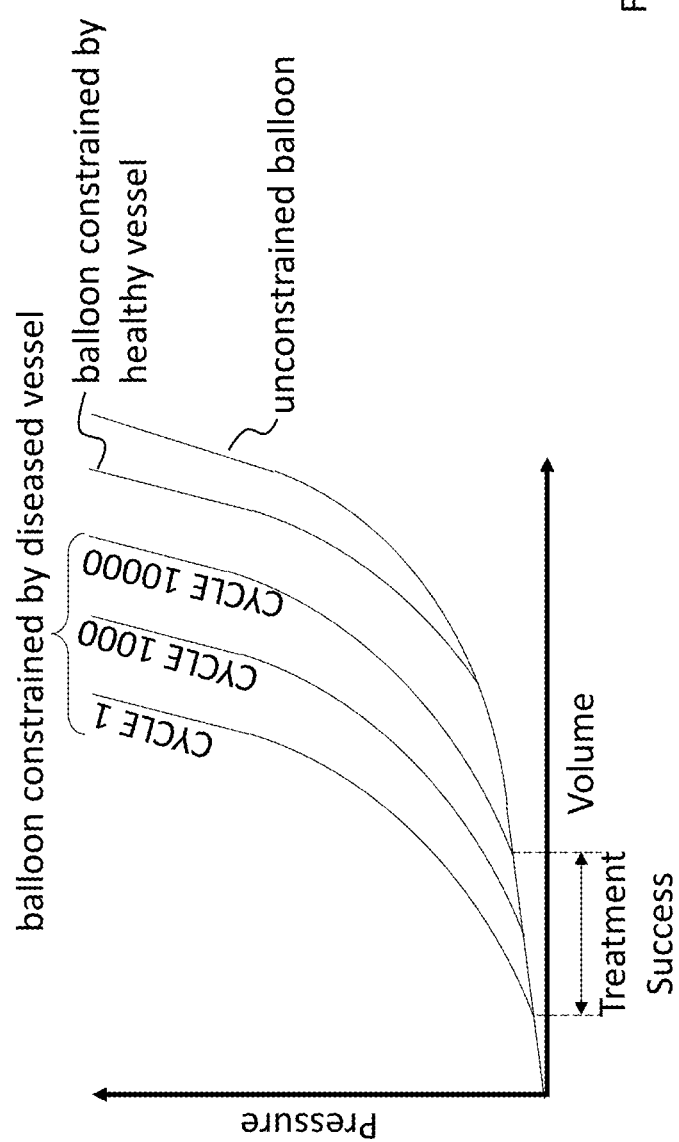
FIG. 7A provides an illustration of pressure-volume relationships under various physical constraints.
Figure 7B:
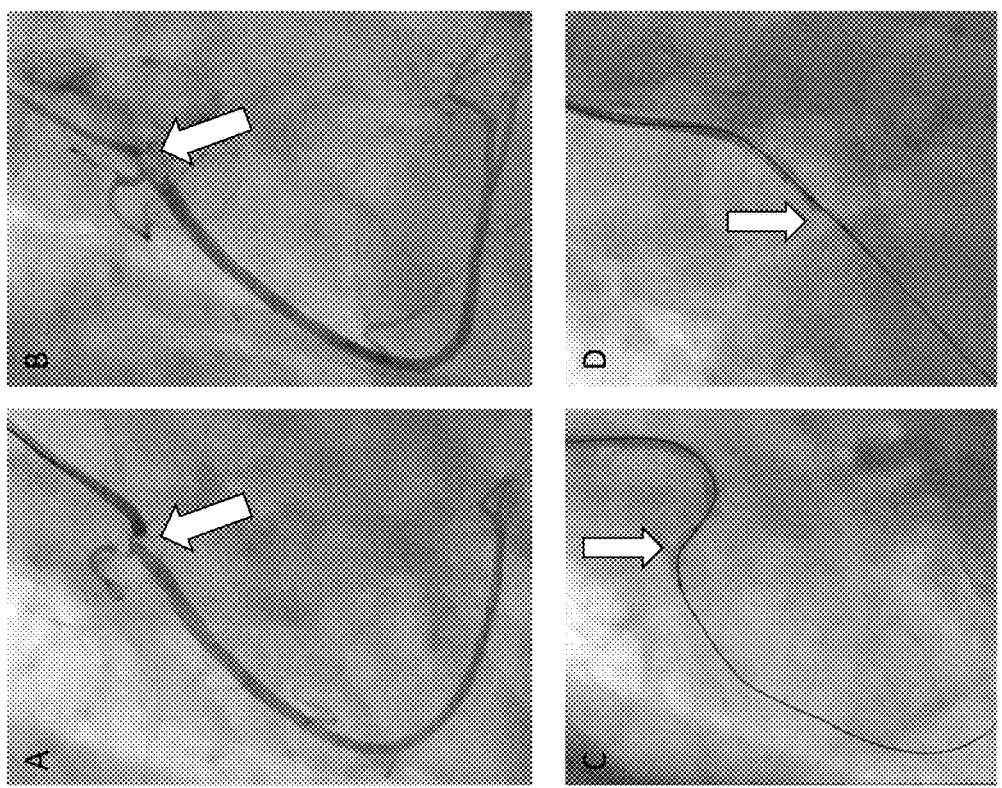
FIG. 7B: (Panels A-B) Example fluoroscopy images of a focal lesion (shown by arrows). (Panels C-D) A balloon is inserted across the lesion and pressurized. In view (Panel C), the balloon appears to be expanded. However, in a normal projection image (Panel D), the balloon is under-expanded.

This pressure-volume relationship of FIG. 5 and "unconstrained balloon" of FIG. 6 represents the relationship between pressure and volume of the balloon when the balloon is not constrained by an external constraint (e.g., a hard stenosis embedded within a vessel wall). When the balloon is constrained by healthy tissue, this pressure-volume relationship is different. In certain cases where the balloon is constrained, the curve has a steeper slope (i.e., the pressure increases with a higher rate for a smaller volume of fluid). Therefore, the pressure-volume curve is case dependent and may be steeper with more diseased tissue. Because this curve is case dependent, the pressure-volume curve must be generated on a case-by-case basis inside the patient (i.e., in-situ) and during treatment. With the described embodiments of the system, both the pressure and the volume in the system can be measured in-situ with varying inputs to the system. For example, at the beginning of the procedure, according to the above embodiments, the pressure in the balloon may be increased to known values while the volume in the balloon (e.g., using the described positional sensor) is measured to generate the in-situ pressure-volume curve (CYCLE 1 of FIG. 7). In certain instances, this treatment-based pressure-volume curve may be compared to the unconstrained pressure-volume curve, which in some cases is an indication of a successful treatment, or to curves measured during the treatment progression (CYCLE 1000 or CYCLE 10000 of FIG. 7). Comparing the pressure-volume curves in this way can be used to provide a repeatable measure of outcome, e.g., treatment success, insufficient balloon diameter, balloon under-expansion, and the like even during pulsatile balloon angioplasty. In other instances, if the treatment is not successful at a certain pressure level over the treatment progression (i.e., the balloon volume remains substantially the same indicating an under-expanded balloon and non-compliant/non-treated vessel), the system may incrementally increase the pressure within a safe range until the balloon volume increases. Alternatively, the system may provide feedback (audio, visual, feel, and the like) to the operator to indicate the pressure amplitude of the pulses is not high enough. In other instances, the system is configured to detect single-plane under-expansion, an example of which is shown in FIG. 7B (Panels A-D). FIG. 7B (Panels A-B) show a fluoroscopy image of a focal lesion, which is restricting blood flow. To treat the lesion, standard BA is performed by inserting the balloon across the lesion and increasing the pressure in the balloon. In one fluoroscopy plane, after increasing the pressure, the balloon expands as shown in FIG. 7B (Panel C). However, as seen in the normal fluoroscopy image plane (FIG. 7B (Panel D)), the balloon remains under-expanded, which could be missed by the physician. With the embodiments described above, the system can measure when the balloon is under-expanded without requiring multiple projection fluoroscopy images. This benefit reduces procedural time, radiation exposure to the physician and patient, and injected contrast.

Measurements of Vessel Compliance

As described in detail below, vessel compliance is a measurable characteristic of blood vessels calculated based on a ratio of the change in vessel volume for a given change in pressure. Vessel compliance is an important characteristic for observation because improving vessel compliance is a prerequisite to definitive treatment of certain underlying blood vessel disease conditions, such as atherosclerosis. Changes in vessel compliance are seen in the different pressure-volume curves depicted in FIG. 7A, described above. In FIG. 7A the pressure-volume, i.e., vessel compliance, characteristic of a treated vessel changes as a result of treatment from CYCLE 1 to CYCLE 1000 to CYCLE 10000.

Figure 7C:
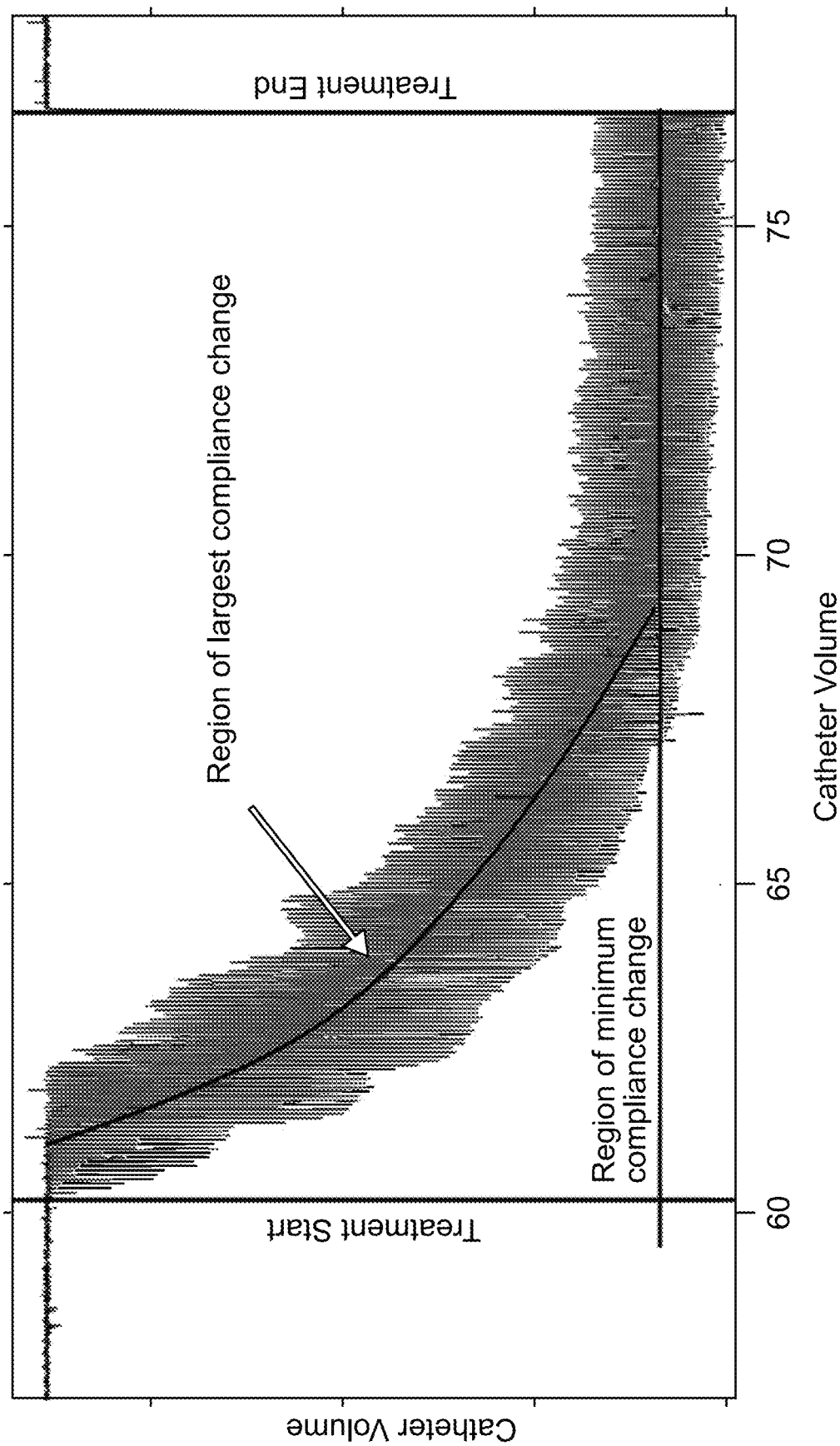
FIG. 7C provides an example of measurements of changes in vessel compliance obtained during treatment using a system according to the present invention.

Systems according to the present invention may be configured to assess vessel compliance by obtaining measurements in-vivo of changes in volume at different pressures (or changes in pressure) applied to vessels. FIG. 7C provides an example of measurements of changes in vessel compliance obtained during treatment using a system according to the present invention. As described in detail below, embodiments of the present invention enable measurement of relative compliance change of the luminal tissue (i.e., a vessel) in real time during application of a system of the present invention to provide pulsatile intravascular lithotripsy treatment. Systems of the present invention may be configured to measure, and update, treatment parameters based on compliance change of the vessel. For instance, after calcium cracking (i.e., breaking up of CP tissue), the luminal tissue (i.e., a vessel) and balloon may expand significantly, contributing to a large gain in compliance, as measured by the system. However, after the vessel has fully expanded, changes in compliance, as measured by the system, may subside. Identification of such conditions may indicate that treatment may be halted because no further appreciable luminal gain is occurring.

Systems may be configured to measure pressure in any convenient manner. In some instances, embodiments of systems according to the present invention may comprise a pressure gauge as described herein for measuring pressure in, for example, fluid passages and distal balloon of a balloon catheter assembly, including, for example, balloon catheter assemblies according to the present invention. In some instances, a pressure gauge may be installed such that it is configured to measure pressures of a distal chamber of a proximal connector, as seen, for example, in pressure transducer 325 in FIG. 3A.

Systems may be configured to measure changes in volume of a vessel in any convenient manner. In some instances, embodiments of systems according to the present invention may be configured such that changes in the position of a membrane separating proximal and distal chambers of the proximal connector reflect changes in volume of the distal balloon. Changes in the volume of the distal balloon reflect changes in the cross-sectional area of a vessel and therefore changes in volume of the vessel. Such embodiments may further comprise a Hall sensor and a permanent magnet for measuring changes in the position of such a membrane. A Hall sensor refers to a sensor configured to sense the presence of, or changes in, a magnetic field, i.e., by use of the Hall Effect. A permanent magnet may be comprised of any convenient magnetic material, or an electromagnet, as desired, such that relative changes in position of the Hall sensor with respect to the permanent magnet are detected by the Hall sensor. Sensors such as the Hall sensor and permanent magnet described above may be used to measure the change in volume of the distal balloon as well as the rate at which the distal balloon inflates, i.e., the rate of vessel volume change.

FIG. 8 depicts the system according to an embodiment of the present invention shown in FIG. 1, further configured to assess vessel compliance according to an embodiment of the present invention. Elements of the system shown in FIG. 8 that are identical to those shown in FIG. 1 are described above in connection with FIG. 1. Hall sensor 805 is positioned on membrane 30 such that changes in position of membrane 30 relative to permanent magnet 810 positioned on proximal connector 400 trigger changes in output of Hall sensor 805. Such changes in output of Hall sensor 805 are indicative of changes in volume of distal balloon 3. As described in connection with FIG. 1, pressure or flow transducer 31 is configured to measure pressure applied to catheter 16 and balloon 2. Measurements of changes in volume based on Hall sensor 805 and permanent magnet 810 and changes in pressure based on pressure gauge 31 are used to measure vessel compliance in-vivo. Such measurements of vessel compliance can be taken during treatment. Such measurements are used to develop pressure-volume curves 815 showing the pressure-volume relationship at a treatment stage. Pressure-volume curves 815 can be generated at different stages of treatment and may be used to assess treatment effectiveness, compare treatment across different settings or to revise or otherwise adjust treatment in order to optimize the effectiveness of treatment. In embodiments, pressure-volume curves 815 may resemble those set forth in, for example, FIG. 7A, described above, or FIG. 17, described below. The data used from these pressure volume curves can be gathered and batched and eventually used to predict (i) success or failure of therapy, (ii) a need to adjust or attenuate energy used in future treatments of populations or similar vessels, (iii) complicating conditions, such as circumferential calcium versus 270 degrees of calcium or (iv) the location of areas in the arterial anatomy that are relatively fixed or those exposed to significant torsion or flexion. While the exemplary embodiment for measuring vessel compliance according to the present invention is shown in FIG. 8 in the context of the system described in connection with FIG. 1, it is to be understood that the technique for measuring vessel compliance according to the present invention is not so limited and may be applied to other balloon-based systems such as those indicated in 820 of FIG. 8, such as, for example, laser-based techniques, ultrasound-based techniques, pulsatile balloon-based techniques, such as those described herein, or plain balloon angioplasty-based techniques. It is also understood that data collected upon application of the system, e.g., in connection with treatment, such as pressure-volume data as described above, may be used to apply various algorithms for machine learning. Such machine learning applications may be trained to make predictions such as those described above, e.g., regarding the success or failure of a treatment, a need to change aspects of the treatment, such as energy applied, the presence of complicating conditions or aspects of the underlying anatomy of a subject or population of subjects. Any convenient machine learning algorithm or technique or model may be applied, for example algorithms or techniques that apply supervised learning, unsupervised learning, semi-supervised learning, reinforcement learning or dimensionality reduction. In embodiments, machine learning techniques of interest may include artificial neural networks, including convolutional neural networks or other methods of applying deep learning techniques, decision trees, support vector machines, regression analysis, Bayesian networks or genetic algorithms. Machine learning techniques of interest may be implemented in software such that they can be executed on a general-purpose processor, such as commercially available general-purpose processors, or a special purposes processor, such as graphics processors, such as commercially available graphics processors, or may be implemented on dedicated hardware.

Figure 9A:
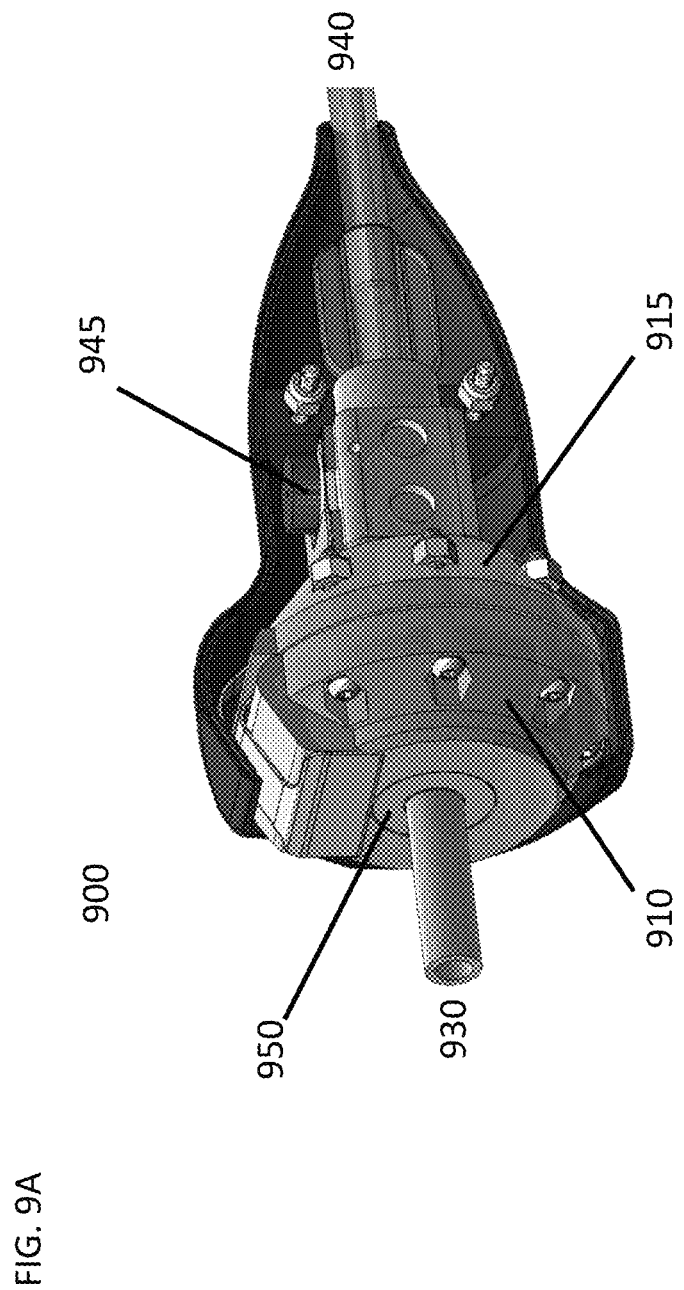
FIGS. 9A and 9B provide various views of a proximal connector of a balloon catheter assembly according to an embodiment of the invention configured to assess vessel compliance in-vivo.
Figure 9B:
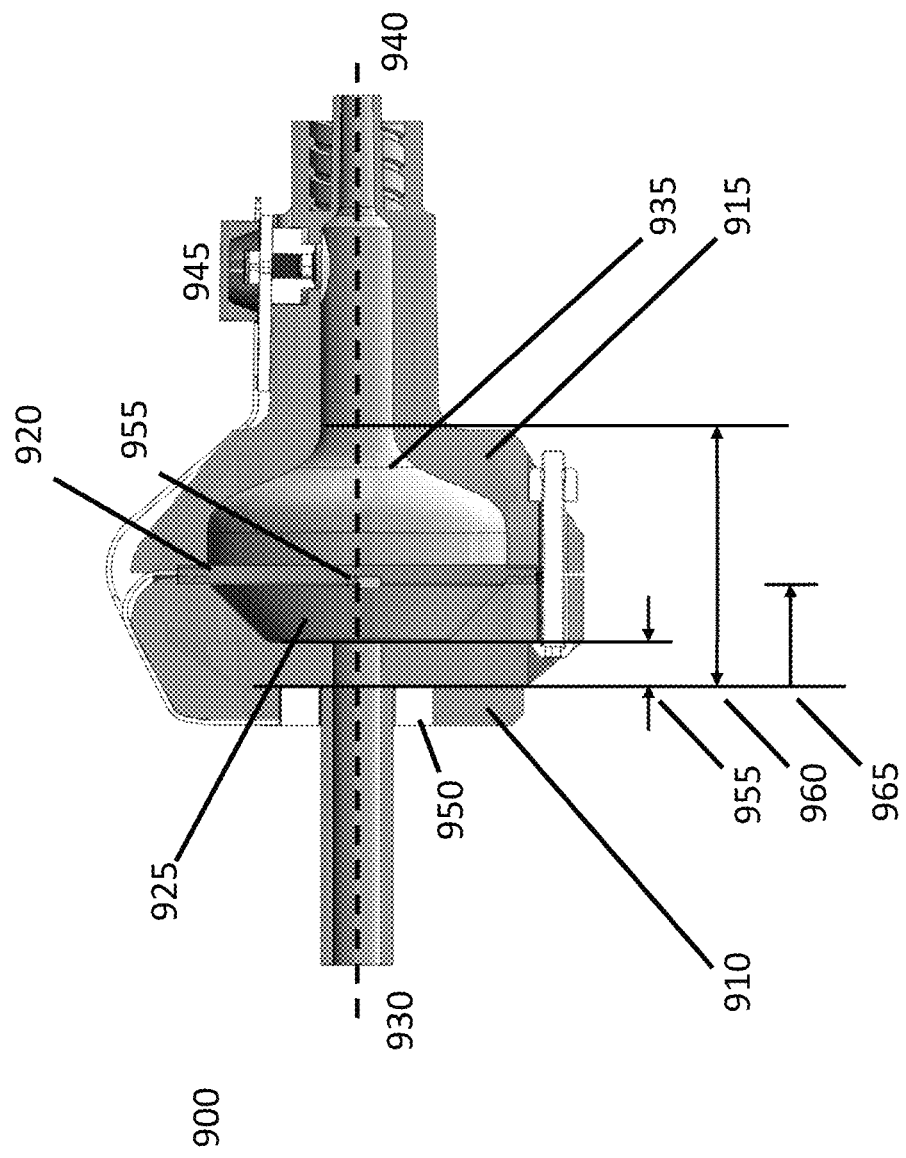

FIG. 9A depicts an isometric view of proximal connector 900 according to an embodiment of the present invention configured for measuring vessel compliance, and FIG. 9B depicts a cutaway view of proximal connector 900. Proximal connector 900 includes proximal flange 910 and distal flange 915 separated by membrane 920. Proximal flange 910 defines proximal chamber 925 which is accessed by proximal port 930. Distal flange 915 defines a distal chamber 935 which is accessed by distal port 940. Pressure transducer 945 is operably coupled to distal port 940 and distal chamber 935 defined by distal flange 915. Pressure transducer 945 is configured to observe changes in pressure applied to a distal balloon connected via distal flange 915. Permanent magnet 950 is connected to proximal flange 910 and is configured to remain in a fixed position relative movement of membrane 920. Hall sensor 955 affixed to membrane 920 is configured to move with membrane 920 relative to permanent magnet 950 enabling observation and measurement of changes in volume of a distal balloon.

Distance 955 represents the furthest left position ($X_l$) that membrane 920 can travel within proximal chamber 925. Distance 960 represents the furthest right position ($X_r$) that membrane 920 can travel within distal chamber 935. Distance 960 represents the position (x) of membrane 920 depicted in FIG. 9B. Hall sensor 955 and permanent magnet 950 are configured to sense changes in membrane 920 position between leftmost distance 955 and rightmost position 960.

Figure 10:
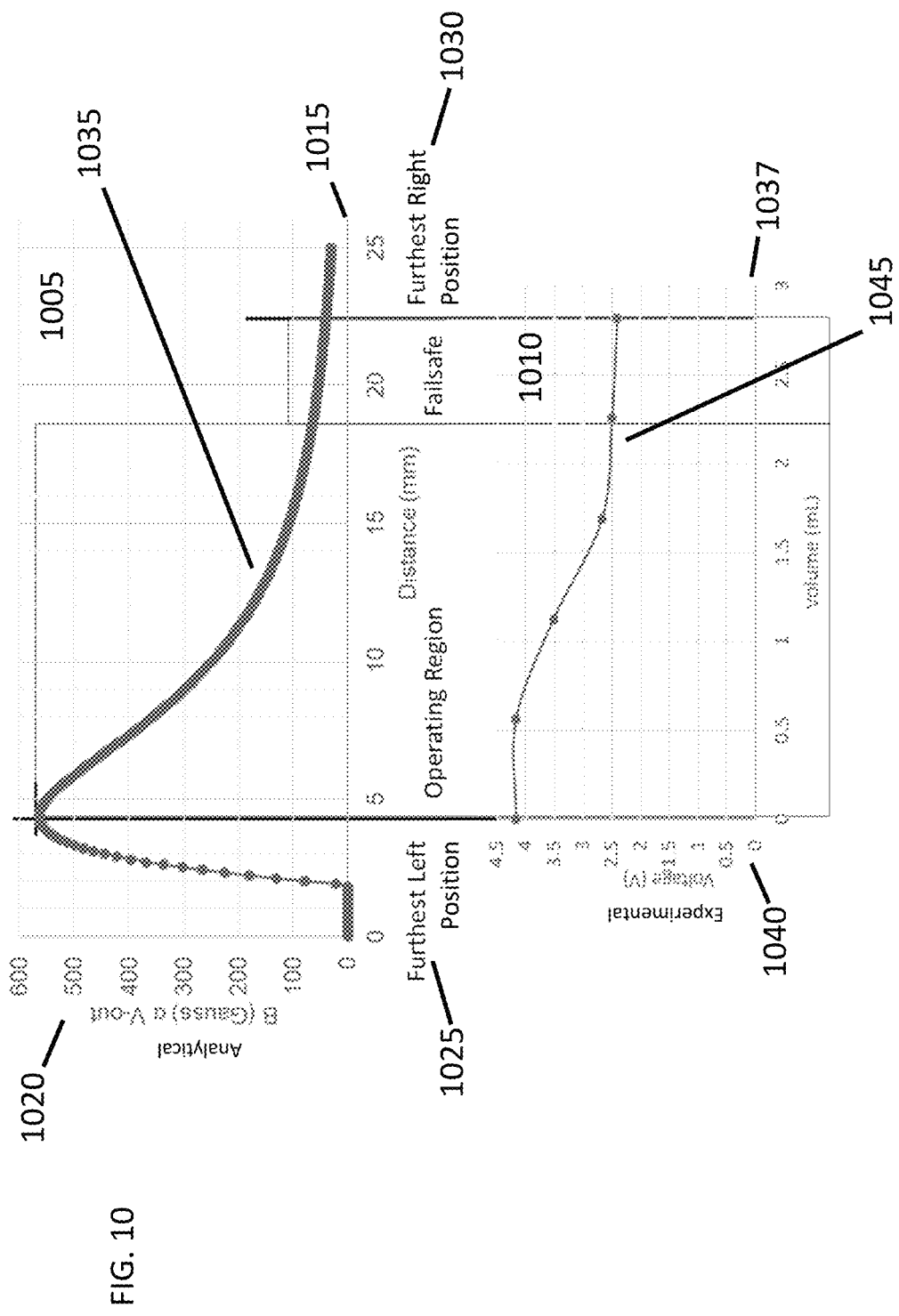
FIG. 10 provides an example of analytical and experimental relationship between membrane position, balloon volume and Hall sensor output.

FIG. 10 depicts a plot 1005 of the calculated, i.e., analytical, output of a Hall sensor affixed to a membrane, such as the configuration of Hall sensor 955 and permanent magnet 950 in the schematic shown in FIGS. 9A and 9B, and a plot 1010 of experimental results confirming the analytical results of plot 1005. The analytical calculation for the magnetic flux density, B, i.e., the magnitude of the effect of the magnetic field, along the symmetry axis of a permanent, axially magnetized ring magnet such as in the configuration of permanent magnet 950 in the schematic shown in FIGS. 9A and 9B is:

$$B = \frac{B_r}{2}\left[\frac{D+z}{\sqrt{R_a^2 + (D+z)^2}} - \frac{z}{\sqrt{R_a^2 + z^2}} - \left(\frac{D+z}{\sqrt{R_i^2 + (D+z)^2}} - \frac{z}{\sqrt{R_i^2 + z^2}}\right)\right]$$

where $B_r$ is the remanence field of the magnet independent of the magnet's geometry, z is the distance from a pole face on the magnet's axis, D is the thickness of the ring, $R_a$ is the outside radius of the ring, and $R_i$ is the inside radius of the ring. The magnitude of the magnetic flux density induces a measurable voltage change in the Hall Effect sensor depending on the distance, z, of the Hall effect sensor from the permanent magnet.

The x-axis 1015 of plot 1005 indicates distance of a membrane from a reference position (i.e., position of a permanent magnet), such as membrane distances 955, 960 and 965 in FIG. 9B. The y-axis 1020 of plot 1005 relates to the magnetic flux density, i.e., the magnitude of the effect of the magnetic field, associated with a permanent magnet at different distances from the permanent magnet. Plot 1005 depicts the leftmost possible membrane position at position 1025, and the rightmost possible membrane position at position 1030 (where "right" and "left" refer to membrane positions seen in FIG. 9B, described above). Analytical results of the effect of the magnetic field versus distance from the permanent magnet are shown on curve 1035. Curve 1035 indicates that effects of the magnetic field vary over the operable range of the membrane, in particular, between position 1025 and position 1030, providing confirmation that a Hall sensor, such as, for example, the configuration of membrane-mounted Hall sensor and permanent magnet shown in FIGS. 9A and 9B, is a feasible solution to measure membrane position and therefore volume of the distal balloon (and therefore changes in vessel volume).

The x-axis 1037 of plot 1010 represents changes in volume of a distal balloon based on different membrane positions. The y-axis 1040 of plot 1010 represents voltage levels generated by a Hall sensor as the Hall sensor travels different distances from a permanent magnet. Curve 1045 reflects voltage data collected from a Hall sensor such as, for example, the configuration of membrane-mounted Hall sensor and permanent magnet shown in FIGS. 9A and 9B. Curve 1045 indicates a different voltage value for each balloon volume value shown on x-axis 1037 (associated with different membrane positions or distances between the membrane and a permanent magnet). That is, each membrane position, and therefore balloon volume, results in a different voltage level generated by the Hall sensor. That is, the function represented by curve 1045 provides a unique solution such that each voltage corresponds to a different membrane position (diaphragm distance from the permanent magnet), which relates to balloon volume. The largest change in measured voltage (plotted on y-axis 1040 of plot 1010) occurs between volume displacement measurements of approximately 0 mL and approximately 2.75 mL, allowing for precise volume measurements through an operating region of interest, i.e., balloon volumes between 0 mL and 2.75 mL. These results provide confirmation that a membrane-mounted Hall sensor is a feasible approach to monitoring volume changes of a distal balloon in-vivo and during treatment.

As described above, measurements of changes in vessel volume in combination with changes in vessel pressure can be used to assess vessel compliance. Use of the systems and techniques described herein allow for assessment of vessel compliance in-vivo and during treatment. Changes in vessel compliance, including changes during treatment or pre- and post-treatment may be used to assess treatment efficacy and/or to adjust vessel treatment. For example, changes in vessel compliance may be used to adjust therapeutic intensity and/or duration. Understanding and collection of data related to treatment, such as measurements of vessel volume and pressure, can be used for future predictive algorithms such that therapy is administered at varying frequencies and/or oscillations to reduce the time necessary for treatment and to more accurately predict the energy required prior to administering therapy. Such aspects of a treatment, e.g., frequency of the system and/or oscillations, may be adjusted by the operator, or in other cases, may be automatically adjusted based on, for example, machine learning and/or other predictive algorithms, as described herein.

As described in detail below, systems and techniques for measuring vessel compliance according to the present disclosure may be further configured to obtain concomitant measures of vessel volume (i.e., absolute, in addition to relative changes in, vessel volume), such as intraarterial cross-section imaging, in order to generate absolute vessel compliance measurements. Imaging techniques such as, for example, ultrasound, cineangiography, computed tomography, intravascular ultrasound (IVUS) and/or optical coherence tomography (OCT), may be used to image treated vessels pre- and post-treatment to obtain absolute vessel compliance measurements. Such measurements of absolute vessel compliance may be compared across treatment groups.

While FIGS. 8, 9A, 9B and 10 depict configurations for measuring vessel compliance in connection with pulsatile balloon catheter systems in accordance with the present invention, such presentation is for illustrative purposes only and disclosure is not limited to such embodiments. It is to be understood that the techniques described for measuring vessel compliance, including in-vivo measurements during treatment by, for example, measuring volume by using a Hall sensor and permanent magnet in conjunction with a pressure gauge, may also be applied to other balloon-based systems and methods, such as other balloon-based systems and methods of treating diseased vessels.

Measurements During Treatment for System Control

Balloon angioplasty systems, such as, for example, pulsatile balloon catheter systems according to the present invention, may benefit from being configured to monitor for safe and effective operation of the system. Systems according to the present invention may be configured to monitor one or more measurable characteristics to ensure safe and effective operation and treatment. For example, in some embodiments of systems of the invention, an output pulse of energy should correspond to an expected value, such as an input pulse of energy or a threshold amplitude of an energy pulse. Such embodiments may be configured to measure, or to compare, or to otherwise monitor, output pulses of energy to ensure compliance. In other embodiments of systems of the invention, the input pressure applied to the system should correspond to the peak pressure measured in the system. In still other embodiments, the input pressure applied to a catheter component should correspond to a target threshold pressure. By "correspond to" an expected value, it is meant, in some cases, that the measured value is greater than the expected value or, in other cases, that the measured value is less than the expected value, in each case depending on the configuration of the system. In another example, in some embodiments of systems of the invention the input pressure applied to the system should correspond to a minimum, or maximum, or acceptable range of, changes in volume of the distal balloon.

More generally, systems according to the present invention may be configured to detect system states. System states may refer to a normal operation state of the system or a fault operation state. A fault operation may mean the system is in any undesired system state, such as an unexpected pressure drop or a system leak or a balloon burst or any other unsafe or ineffective state.

This aspect of the present invention relates to a simple, effective, and fast technique for detecting system states, as described above, and providing an alarm signal indicating such system fault. In addition, this aspect of the system can also be used to predict what amount of oscillation or energy is needed rapidly after the earliest data is collected on compliance. In pulsatile balloon catheter systems, system states may be determined by configuring the system to compare a measured characteristic of the system, e.g., catheter pressure, such as peak catheter pressure, or distal balloon volume, to an expected threshold, i.e., target pressure or target volume, or minimum or maximum expected values thereof. Catheter pressure may be measured using any convenient pressure sensor, such as, for example, a pressure gauge, as described above. In some cases, a pressure sensor may be integrated into a distal chamber of a proximal connector of an embodiment of a system according to the present invention. In such cases, the pressure sensor may be configured to measure pressure applied to a distal balloon, by, for example, measuring fluid pressure in the distal chamber in fluidic communication with a distal balloon. Distal balloon volume may be measured using any convenient sensor, such as, for example, a membrane positional sensor or displacement sensor or other sensor, such as those described herein, configured to measure changes in volume of the distal balloon. In some cases, the membrane positional sensor is a Hall sensor and a magnet present at a fixed location of the membrane of the proximal connector configured to measure changes in volume corresponding to the distal balloon, as described above.

In embodiments, an electronic circuit may be configured to determine system states. In such embodiments, a sensor configured to measure a system characteristic, such as those described herein, may be further configured to output an electronic signal based on the measured characteristic. A person of skill in the art will understand that any desired, measurable system characteristics may be measured by an appropriately configured sensor. In embodiments, a sensor configured to measure a system characteristic, such as a pressure sensor configured to measure system pressure or a membrane positional sensor configured to measure distal balloon volume, may be further configured to output an electronic signal based on the measured characteristic, such as measured pressure or measured volume. Such electronic signal may vary based on the output of the sensor, i.e., the measured system characteristic, for example, the amount of pressure measured by a pressure sensor or the volume of the distal balloon measured by the membrane positional sensor. The electronic signal corresponding to the measured system characteristic may be a digital signal or an analog signal. When the signal is an analog signal, its voltage or current, or any other characteristic of the signal, such as a frequency, may vary based on different measurements observed by the sensor. The electronic circuit may be configured to compare the measured system characteristic, such as the measured pressure signal or measured volume signal, to a target pressure or target volume (i.e., a minimum or maximum or acceptable range of the system characteristic) in any convenient manner. For example, the measured signal may be compared to a target threshold, such as a target pressure or target volume, using a comparator circuit to compare the measured system characteristic to a reference voltage corresponding to a target threshold. Any convenient comparator circuit capable of comparing the difference between characteristics of signals, such as comparing signal voltage or current, and producing a digital (i.e., binary) output indicating the result of the comparison, e.g., which signal is larger, may be applied. In some cases, the comparator circuit may be an analog comparator circuit, such as a differential amplifier, for example, a high-gain differential amplifier. In other cases, the comparator circuit may be a digital circuit, such as an adder circuit or a more complex or more specialized digital logic circuit.

In some cases, the signal corresponding to the measured system characteristic, such as a measured pressure or a measured volume, may be inverted and summed with a signal corresponding to a target value or threshold, such as a target pressure or target volume. The result of the summation may then be applied to a comparator circuit for comparison against a threshold where the threshold represents a tolerance or expected difference between the measured system characteristic and a target threshold (e.g., measured pressure and a target pressure or measured volume and a target volume). Such a configuration, where the difference between the measured system characteristic and a target value of the system characteristic (e.g., measured pressure and a target pressure or measured volume and a target volume) is compared to a threshold, may allow for a buffer around the expected system characteristic, which in some cases, may account for noise or other signals that are not representative of system state.

In embodiments, the result of the comparator circuit may be (or in some cases may be converted to) a digital signal, where the logical value of the digital signal indicates whether the measured system characteristic (such as measured pressure or measured volume) is an expected or unexpected reading. For example, the circuit may be configured such that the comparator produces a digital high signal, i.e., a logical 1, when the measured system characteristic (e.g., measured pressure or measured volume) falls outside of an expected range and a digital low signal, i.e., a logical 0, when the measured system characteristic falls within an expected range. Such digital signal may be stored in a memory. Any convenient electronic circuit capable of storing a digital logic signal may be applied. In some cases, the memory may consist of a flip-flop circuit, for example a flip-flop capable of storing a single bit. In such instances, the output value of the flip-flop reflects system state. For example, the output of the flip-flop may indicate a logical 0 when the system state is normal and a logical 1 when the system state is in a fault state. Such an output of the flip-flop may be treated as an alarm signal such that when the alarm signal is raised, continued use of the system may be unsafe or ineffective. Such signal may be conveyed to an operator of the system in any convenient manner. For example, in some cases, system state may be conveyed to the operator through a warning signal such as a warning light or sound or vibration. In other cases, system state may cause the system to automatically take an action, such as automatically turning off aspects of the system.

In certain embodiments, it may be desirable for the system state value stored in memory, e.g., the value stored in the flip-flop, to reflect a comparison of the maximum or minimum of the measured system characteristic, such as a comparison of the measured pressure at peak amplitude of the measured pressure or a comparison of the measured distal balloon volume at peak amplitude of the measured volume. That is, in embodiments, the system state reflects peak catheter pressure or peak distal balloon volume. This digital data can be used for understanding population and anatomic variables and the pressures and energy needed as well as in connection with machine learning techniques, such as, for example, training data for machine learning models, to predict the energy needed and best therapeutic energy to apply. In such embodiments, system state may reflect whether the peak measurement of a system characteristic rises to or above a target measurement value of the system characteristic, e.g., whether the peak amplitude of the measured pressure or measured distal balloon volume rises to or above a target pressure or volume, respectively, at an expected time. In such embodiments, when the peak value of the measured characteristic fails to rise to the level of an expected target value at an expected time, an unexpected pressure drop, for example, may be indicated. In some embodiments, the system may be configured to continuously monitor a system characteristic, such as catheter pressure or distal balloon volume, and continuously compare such measurement against target value. In such cases, in order for the output state of the flip-flop to accurately reflect system state, the system may be configured such that the result of the comparator circuit is written to the flip-flop at a time corresponding to the time when the catheter is expected to be exposed to a peak measurement value, e.g., peak pressure or peak volume. That is, the flip-flop write operation is coordinated with the time the system is expected to exhibit a peak measurement value, e.g., peak pressure or peak volume. Any convenient technique to synchronize sensor readings at the appropriate time may be applied. In some cases, the flip flop write operation may be synchronized by setting the flip-flop clock signal to an inverted control signal used to control input pressure to the catheter. In such instances, the leading edge of the flip flop clock signal corresponds to the time that the control signal turns off pressure to the catheter, which in turn corresponds to a time that pressure has been applied to the catheter the longest, i.e., peak catheter pressure. Those skilled in the field will understand that alternative configurations may be employed with similar effect, such as using a falling-edge triggered flip-flop without inverting the pressure control signal.

When configurations such as those described above for synchronizing a flip-flop write operation with a peak value of a system characteristic, such as peak system pressure or peak distal balloon volume, are applied, the system state reflected in the logical value of the memory device, i.e., flip-flop, reflects the peak value of the measured system characteristic, e.g., peak pressure or peak volume. As such, system state may indicate that the system fails to reach a peak measurement value at any time during pulsatile cycle of applying and then removing pressure to the distal balloon and therefore the system is not functioning safely or effectively or otherwise as expected.

Figure 11:
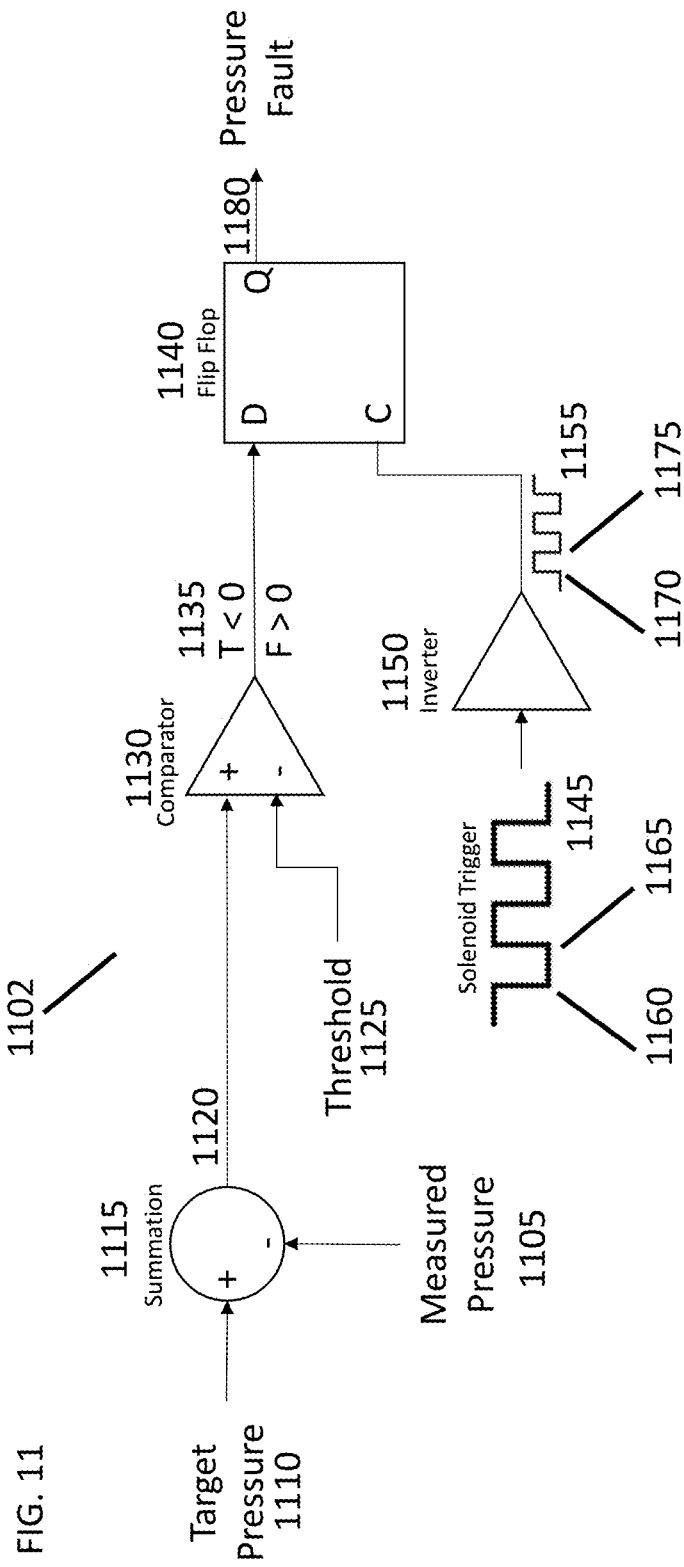
FIG. 11 presents a circuit diagram of an exemplary electronic circuit for monitoring system state according to the present invention.

FIG. 11 presents a circuit diagram of an exemplary electronic circuit 1102 for monitoring system state via catheter pressure according to aspects of the present invention. While the diagram shown in FIG. 11 relates to measuring catheter pressure, those skilled in the field will understand that similar configurations may be employed to measure other system characteristics, such as, for example, distal balloon volume. As seen in FIG. 11, measured pressure 1105 is an input signal to circuit 1102. As described herein, the measure pressure signal may be an analog or digital signal ultimately generated by a pressure sensor attached to the embodiment of the system and used to measure energy applied to the system, such as catheter pressure. Target pressure 1110 is another electronic signal that is an input signal to circuit 1102. Target pressure signal 1110 may be hardwired to a specified value or may be configurable based on different types of distal balloons, different types of treatment strategies, including the amount of pressure expected to be applied to the catheter. Measured pressure 1105 and target pressure 1110 are routed to a summation circuit 1115 configured to compute the difference between measured pressure 1105 and target pressure 1110. That is, in the embodiment depicted in FIG. 11, summation circuit 1115 is configured to add target pressure 1110 to a negative value of measured pressure 1105.

Summation result 1120 of summation circuit 1115 is compared against threshold value 1125. Summation result 1120 and threshold value 1125 are both inputs to comparator circuit 1130. Threshold value 1125 is an input signal to circuit 1102 and may be a hardwired value or may be a configurable value that in either case reflects acceptable tolerance between measured pressure 1105 and target pressure 1110. Comparator circuit 1130 is configured to produce a comparator result 1135 that is a digital low value, i.e., logical 0, if the result of the comparator circuit 1130 is within an allowable tolerance and to produce a digital high value, i.e., logical 1, if the result of the comparator circuit 1130 is outside an allowable tolerance. That is, for example, in the event measured pressure signal 1105 is unacceptably low, summation result 1120 will, as a result, also be unacceptably low, causing comparator result 1135 to be a digital high value or logical 1. Comparator result 1135 is connected to the data-in port of flip-flop 1140, used to store system state, in this case in the form of a one-bit digital logic value.

Solenoid trigger signal 1145 is a pressure control signal used to control a solenoid that turns on pressure to a catheter. That is, when solenoid trigger signal 1145 is high, the solenoid is controlled such that pressure is input into the catheter (not shown in FIG. 11) and therefore applied to the distal balloon (not shown in FIG. 11). When embodiments are configured as such, pressure will have been applied to the catheter for the longest amount of time upon the trailing edge (i.e., falling edge) of solenoid trigger signal 1145. Because the catheter will have been exposed to pressure for the longest time upon the trailing edge of solenoid trigger signal 1145, catheter pressure is expected to be at its peak amplitude at that time. That is, maximum catheter pressure is expected upon each trailing edge of solenoid trigger signal 1145.

Prior to being routed to the flip-flop clock input signal, solenoid trigger signal 1145 is inverted using inverter 1150. Any convenient inverter circuit or digital logic NOT gate may be applied to cause inverter output 1155 to logically reflect an inverted solenoid trigger signal 1145, such that, for example, leading edge 1170 of inverter output 1155 corresponds to trailing edge 1160 of solenoid trigger signal 1145 and falling edge 1175 of inverter output 1155 corresponds to leading edge 1165 of solenoid trigger signal. Therefore, when flip-flop 1140 is a positive-edge triggered flip-flop, i.e., it is configured such that the stored value is written upon each leading edge of the flip-flop clock signal, comparator result 1135 will be written to flip-flop 1140 upon each trailing edge of solenoid trigger signal 1145. When comparator result 1135 is written at the trailing edge of solenoid trigger signal 1145, comparator result 1135 reflects a comparison of measured pressure 1105 at the peak amplitude of pressure applied to the distal balloon through the catheter.

In the embodiment shown in FIG. 11, flip-flop output signal 1180 reflects system state. When the system is functioning normally electronic circuit 1102 is configured so that flip-flop output signal 1180 is a digital low or logical 0 value meaning measured pressure appears to be within an acceptable threshold of target pressure and no unexpected pressure drop is detected. When the system is in a fault state, electronic circuit 1102 is configured so that flip-flop output signal 1180 is a digital high or logical 1 value meaning measured pressure appears to be outside an acceptable threshold of target pressure and an unexpected pressure drop has been detected.

Figure 12A:
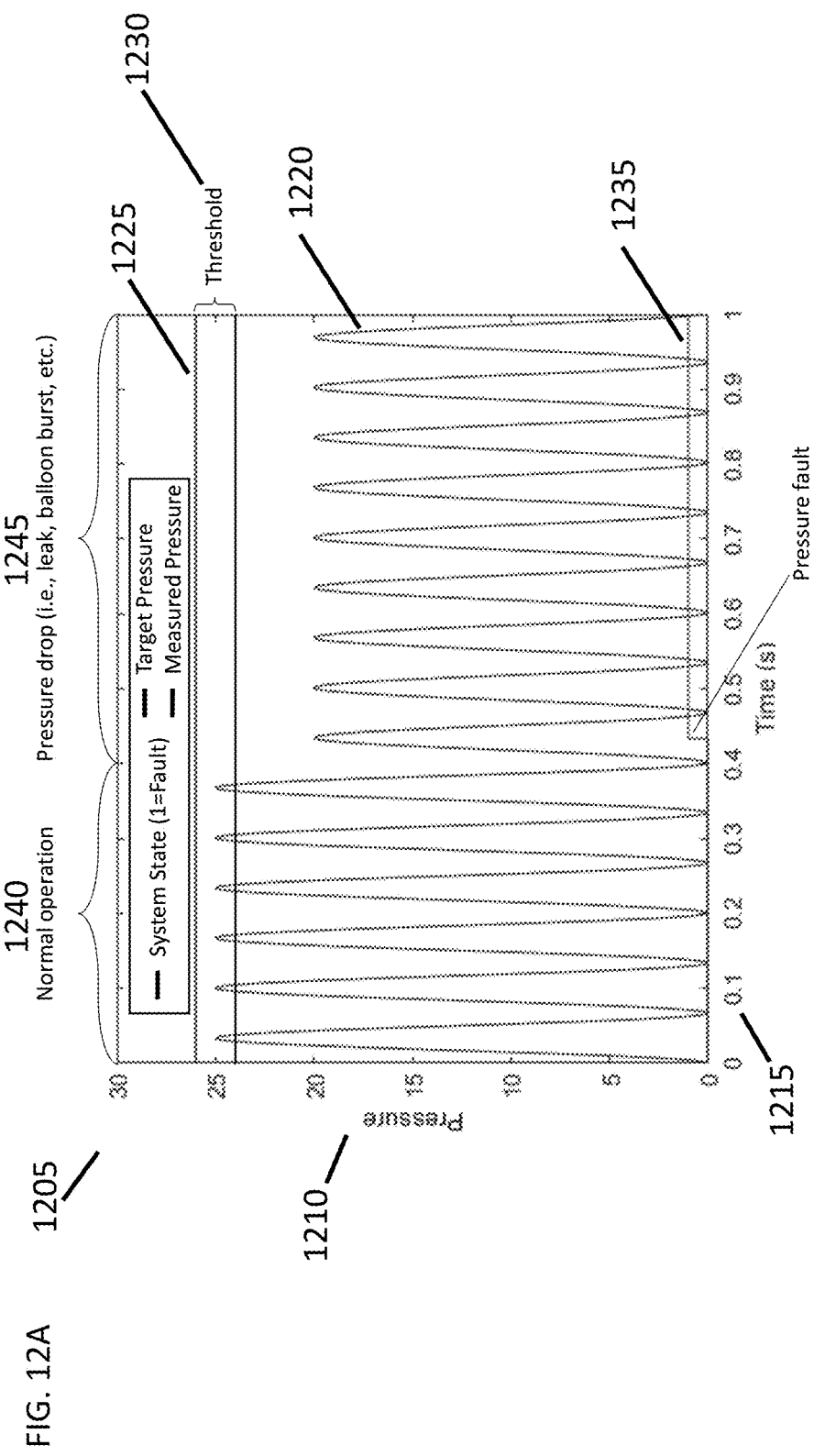
FIG. 12A shows results of operation of an exemplary electronic circuit for monitoring system state according to the present invention.

FIG. 12A shows results of operation of an exemplary electronic circuit used to monitor system state according to the present invention, such as, for example, the operation of electronic circuit 1102 depicted in FIG. 11 and described above. Plot 1205 is a graph of pressure 1210, shown on the y-axis of plot 1205, over time 1215, shown on the x-axis of plot 1205. Pressure measured in the system, i.e., catheter pressure, is shown on the plot on curve 1220. Because pressure applied to the catheter is pulsed, i.e., is pulsatile, measured pressure 1220 forms a waveform with a peak (i.e., greatest magnitude of pressure) and a trough (i.e., least magnitude of pressure) in a periodic manner (in embodiments, the amplitude of the waveform may remain constant or can change based on feedback from a variety of sensors or other system feedback or pre-programmed instructions, for example). Target pressure for the system, i.e., the maximum expected pressure, is depicted by line 1225, which shows an exemplary target pressure on plot 1205. The threshold for tolerable variances from target pressure 1225 is shown as the pressure band 1230 reflecting a range of acceptable differences in pressure values from target pressure 1225. System state signal 1235 reflects logical values 0 or 1, where logical value 0 indicates normal operation of the system and logical value 1 indicates a system fault.

Plot 1205 shows normal system operation during time period 1240, between approximately time 0 and 0.4 seconds. During time period 1240, peak measured pressures consistently rise nearly to target pressure 1225 and is consistently within the acceptable threshold 1230 of target pressure 1225. Because catheter pressure is consistently within an acceptable pressure range during this time, the electronic circuit configured to monitor system state consistently indicates normal system operation. This result is reflected in system state signal 1235 remaining at logical 0 during time period 1240.

Also shown on plot 1205 is a period of system fault during time period 1245, between approximately 0.4 seconds and 1 second. During time period 1245, peak measured pressures consistently fail to rise to target pressure 1225 and are consistently outside of the acceptable threshold 1230 of target pressure 1225. Because peak catheter pressure is consistently outside the acceptable pressure range during this time, the electronic circuit configured to monitor system state consistently indicates a system fault due to the measured pressure drop. This result is reflected in system state signal 1235 rising to and remaining at logical 1 during time period 1245.

Catheter Burst Detection

Systems according to the present invention may be configured to detect whether a catheter is an intact catheter, whether the catheter has completely failed or whether the catheter has a leak.

Figure 12B:
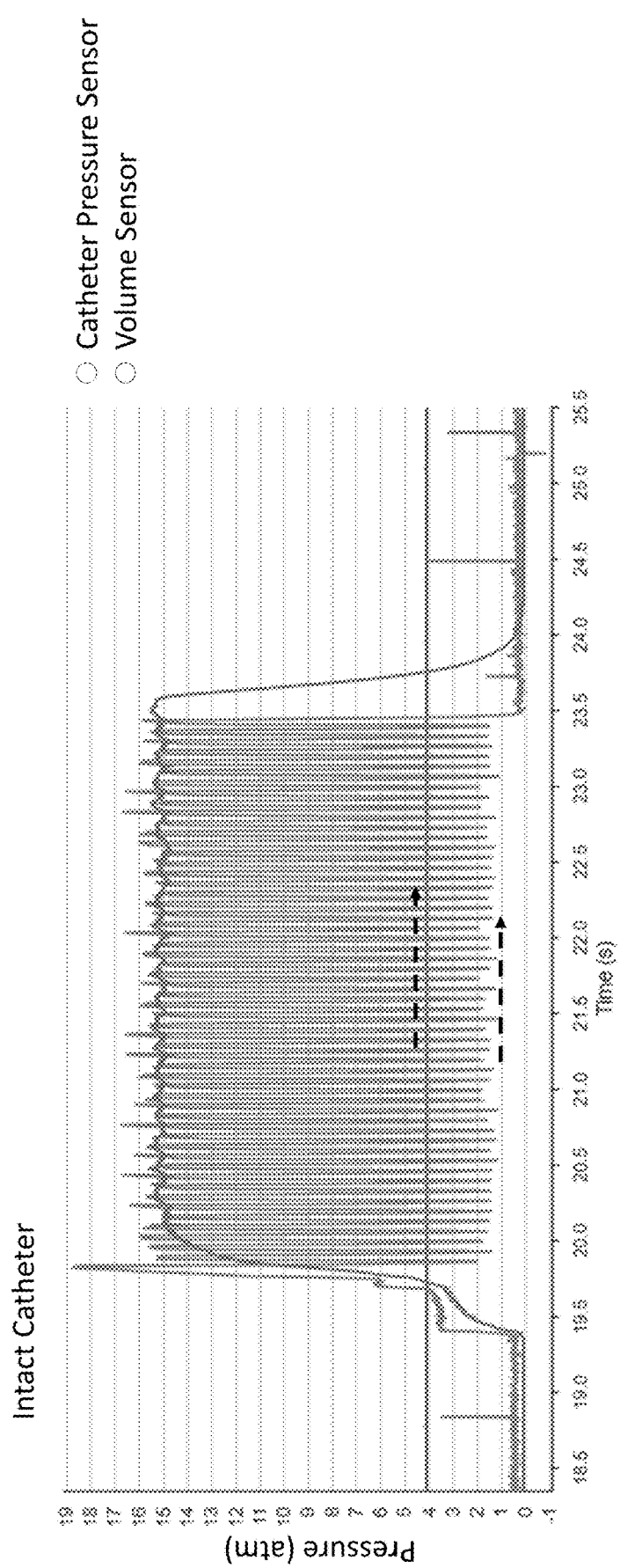
FIG. 12B depicts example behavior of pressure and volume measurements from an intact (i.e., not leaking) catheter of a system according to the present invention during treatment.

FIG. 12B depicts example behavior of pressure and volume measurements from an intact (i.e., not leaking) catheter of a system according to the present invention during treatment. In FIG. 12B, the peak and trough pressures remain substantially the same throughout treatment and the volume over the treatment does not decline.

Figure 12C:
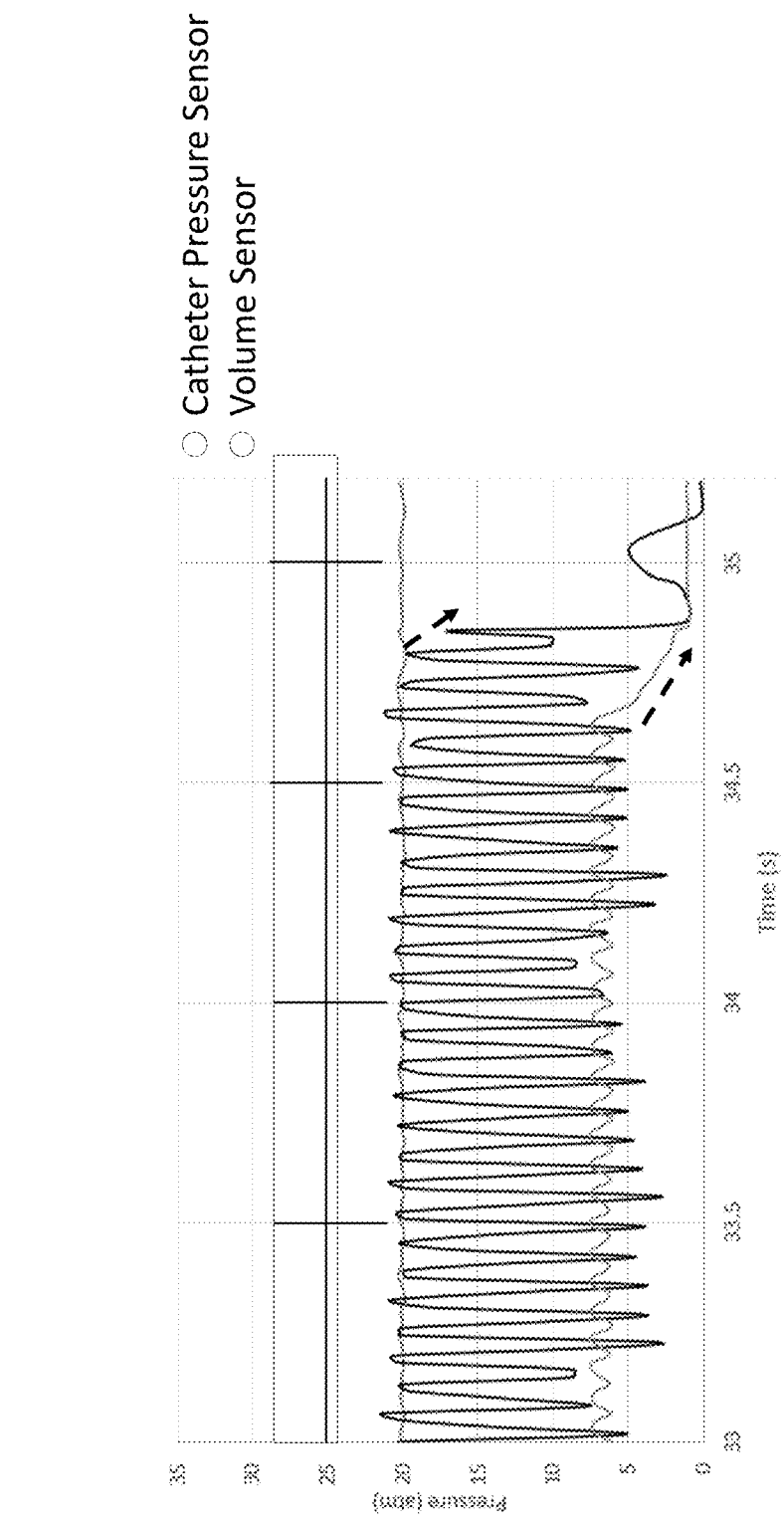
FIG. 12C depicts example behavior of pressure and volume measurements from a completely failed catheter of a system according to the present invention during treatment.

FIG. 12C depicts example behavior of pressure and volume measurements from a completely failed catheter of a system according to the present invention during treatment. A completely failed catheter can cause damage to the lumen and can cause damage to the amplifier assembly. Using catheter pressure and volume change, a burst catheter may be detected within less than 0.05-2 seconds such as 0.1 seconds of treatment. In the figure above, the volume sensor measures a drop in volume, which triggers a system warning and stops the treatment. Volume decrease may be in the range of 0.01 to 10 mL/sec such as 0.5 mL/sec. Peak pressure also decreases during the burst but lags the volume change.

Figure 12D:
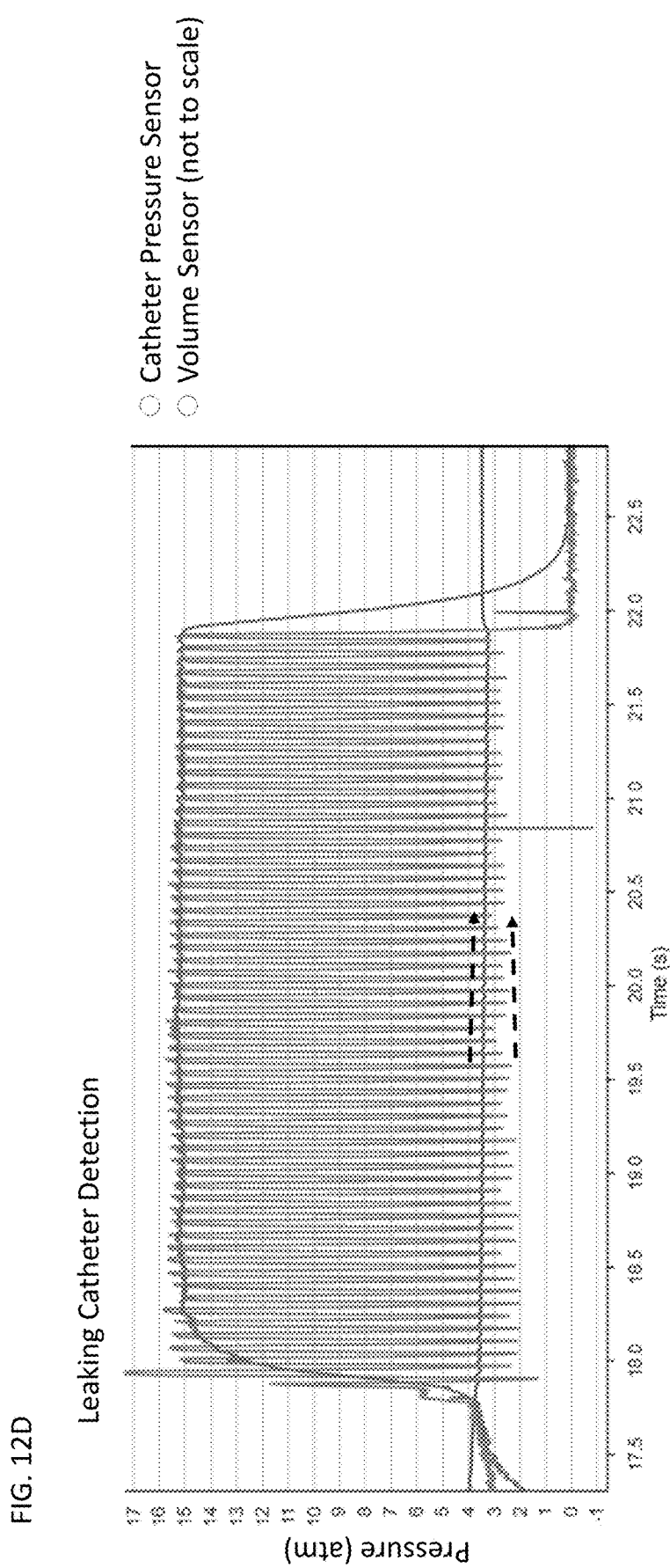
FIG. 12D depicts example behavior of pressure and volume measurements from a leaking catheter of a system according to the present invention during treatment.

FIG. 12D depicts example behavior of pressure and volume measurements from a leaking catheter of a system according to the present invention during treatment. A leaking catheter can cause a jet of fluid that damages the vessel wall. Using catheter pressure and volume change, as measured by an embodiment of the present invention, the leaking of the catheter can be detected by measuring an increase in trough pressure during the pressure cycle along with a decreasing volume in the catheter. Trough pressure increase may be in the range between 0.1-10 atm such as 1-2 atm. Volume decrease may be in the range of 0.01 to 10 mL/sec such as 0.1 mL/sec. In certain embodiments, a software-based scheme may be used to detect the combination of these conditions to immediately shut off the system during pulsatile intravascular lithotripsy therapy.

Specific Embodiment of Barrel Connector

Figure 13:
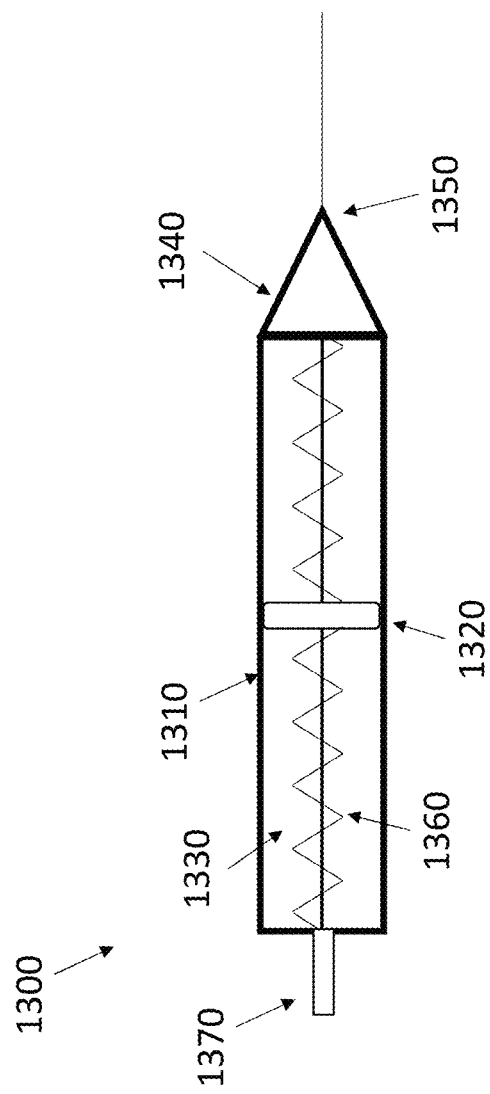
FIG. 13 provides a schematic of an embodiment of an alternative connector configured to deliver a high-volume, low-frequency, and low-pressure pulse.

FIG. 13 provides a schematic of an alternative connector 1300 configured to deliver a high-volume, low-frequency and low-pressure pulse (i.e., pulsatile energy). Connector 1300 comprises barrel syringe 1310 with plunger (i.e., piston) 1320 separating pneumatic chamber 1330 from fluid chamber 1340. Pneumatic chamber 1330 comprises pneumatic input port 1370, configured to receive energy (i.e., a first pulse energy) from the manifold assembly (not shown), e.g., in the form of pneumatic pressure, and transmit such energy to pneumatic chamber 1330. Plunger 1320 is configured to translate in response to pressure applied to pneumatic chamber 1330, in turn transmitting energy to fluid chamber 1340. Fluid chamber 1340 comprises fluid output port 1350 operably connected to a catheter (not shown) and configured transmit energy to catheter (i.e., a fluidic chamber thereof) in response to movement of plunger 1320 compressing fluid chamber 1340. Connector 1300 further comprises biasing spring 1360 configured to urge plunger 1320 to return to a starting position when plunger 1320 is displaced.

In instances where a connector comprises an internal fluid, the connector may be configured to receive fluid through a fluidly coupled priming port (not shown). For example, such a fluid port may be connected to fluid chamber 1340 in connector 1300 of FIG. 13. Through such a port, a fluid such as radiopaque contrast, saline, $CO_2$ or the like may be injected to prime the fluid chamber. Additionally, a vacuum may be applied to such a port so that the connector as well as the system as a whole can be, for example, de-gassed prior to treatment. The priming port may be closed and sealed so that no fluid may exit the port during treatment.

Methods

Systems of the invention find use in a variety of applications. In some instances, the systems find use in fracturing hardened materials embedded within an elastic conduit. For embodiments presented herein, the present disclosure describes applications related to treating atherosclerotic calcifications within an arterial conduit, such as a coronary or peripheral artery. However, the present system and teachings are not solely limited to atherosclerotic calcifications nor arterial conduits and may be generally applied to other applications as determined by those skilled in the art. For example, this is especially true for circumstances that alter arterial compliance (vessel compliance, as described above, of an artery) or for cases that involve medical interventions, such as the presence of a previous stent with subsequent blockage. The compliance of the vessel is altered by the intra-luminal placement of a previous stent. Data and feedback of vessel compliance curves can be used in connection with future therapies as well as for prediction techniques, such as machine learning techniques described herein.

Figures 14A, 14B, 14C, 14D, 14E:
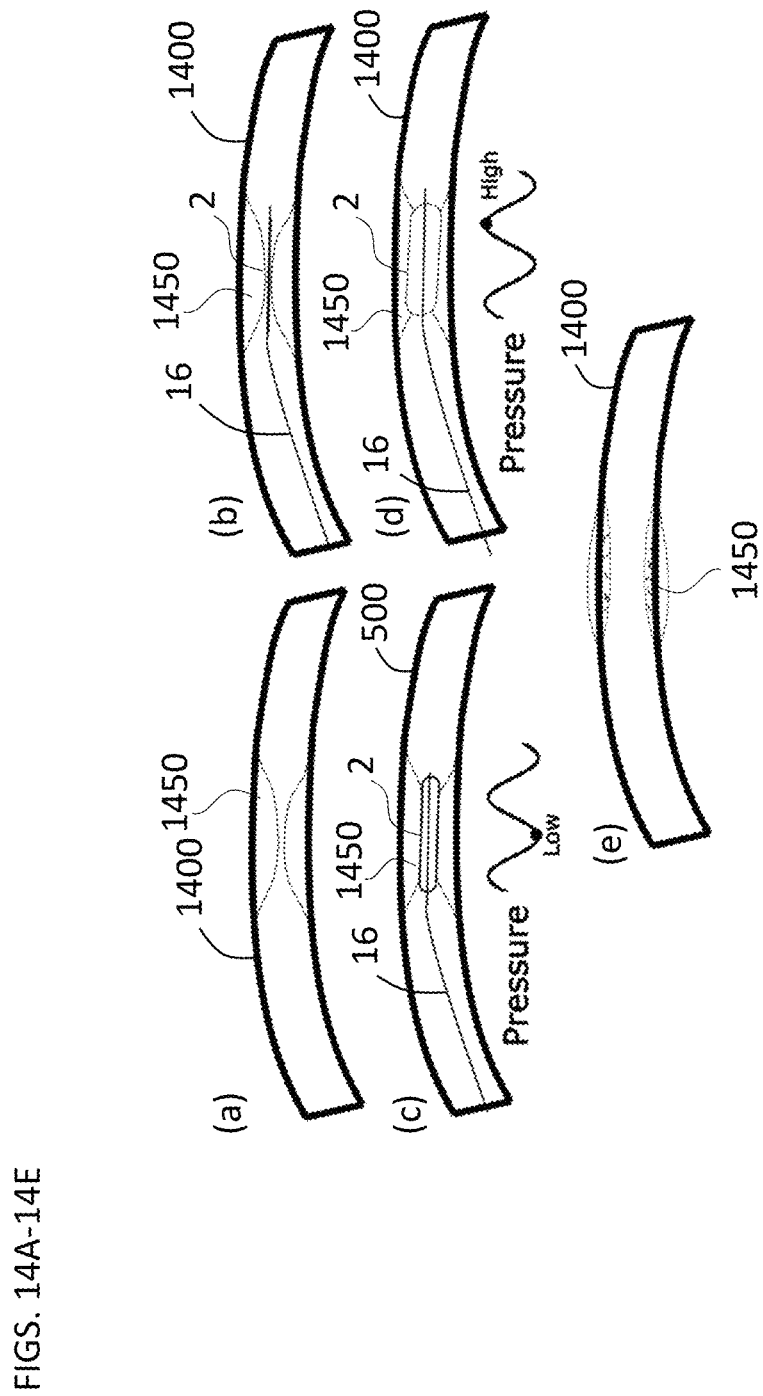
FIG. 14A is a schematic view of an elastic conduit (e.g., artery) having a hardened material (e.g., calcified plaque) embedded therein to be treated by the dynamic balloon angioplasty (DBA) techniques and devices according to some embodiments of the present teachings.
FIG. 14B is a schematic view of the elastic conduit of FIG. 14A having a DBA angioplasty balloon navigated to the affected region and pre-pressurized.
FIG. 14C is a schematic view of the elastic conduit of FIG. 14A having the DBA angioplasty balloon cycled to a low pressure.
FIG. 14D is a schematic view of the elastic conduit of FIG. 14A having the DBA angioplasty balloon cycled to a high pressure.
FIG. 14E is a schematic view of the elastic conduit of FIG. 14A having the hardened material fractured according to the principles of the present teachings.

In some instances, the various embodiments of the systems described herein are employed in methods of dynamic balloon angioplasty (DBA), a technique that uses pressure oscillations with a generalized waveform (in some embodiments, harmonic, or frequency-specific, pressure waveform oscillations) to effectively and safely fracture calcified lesions during angioplasty. The concept of DBA for treating arterial calcified plaque is illustrated in FIGS. 14A-14E. In DBA, a catheter 16 with balloon 2 is deployed to the vessel 1400 with calcification 1450 (FIG. 14B), e.g., with the assistance of a guidewire using any convenient protocol, such as those known in the art. Through the angioplasty balloon, the plaque is subjected to high-frequency pressure oscillations (FIGS. 14C-14D). In the low-pressure phase of the oscillations (FIG. 14C), the balloon pressure is reduced to near the minimum pressure needed to achieve balloon inflation, typically 1-2 atm. In the high-pressure phase of the oscillations (FIG. 14D), the balloon is inflated to a peak pressure, which can be set by the physician or system. Typical peak inflation pressures may be from above the low-pressure range to the balloons' max rated pressure, which could be 25 atm or more. Pressure cycling of the balloon in this manner induces cyclical loading of the calcified plaque 1450 below the calcified plaque's rupture stress yet in the plastic deformation zone. The heterogeneity of the calcified plaque interior is composed of many microfractures with sharp corners. Through the fracture mechanisms described herein, the cyclic loading described in FIGS. 14A-14E causes cyclic stresses at these sharp corners near plaque microfractures and irregular surfaces. The cyclic stress initiates and grows these sharp corners, which expand the microfractures into larger macroscopic fractures. The growth of these microfractures leads to the more complete fracture of plaque at lower inflation pressures compared to static pressure. Higher frequency pressure cycles and higher-pressure differences between the cycles is expected to increase the effectiveness of this crack growth mechanism. By generating controlled high-frequency pressures cycles in an angioplasty balloon, DBA lowers the required balloon pressure for fracturing calcified plaque (e.g., in some instances between 1 to 50%, such as 20 to 30%, as compared to a suitable non-DBA control), improves stent deployment, improves and controls drug delivery for drug-coated balloons, stress-softens soft, lipid-core atheromatous plaques, expands calcified in-stent restenoses, and fracture calcifications on diseased cardiac valve leaflets and improves balloon-based expansion and deployment of prosthesis and devices. Further details regarding embodiments of DBA methods in which the systems described herein may be employed are provided in United States Published Patent Application Publication No. 20200046949 as well as pending PCT Application Serial No. PCT/US2020/055458; the disclosures of which are herein incorporated by reference.

Figure 15:
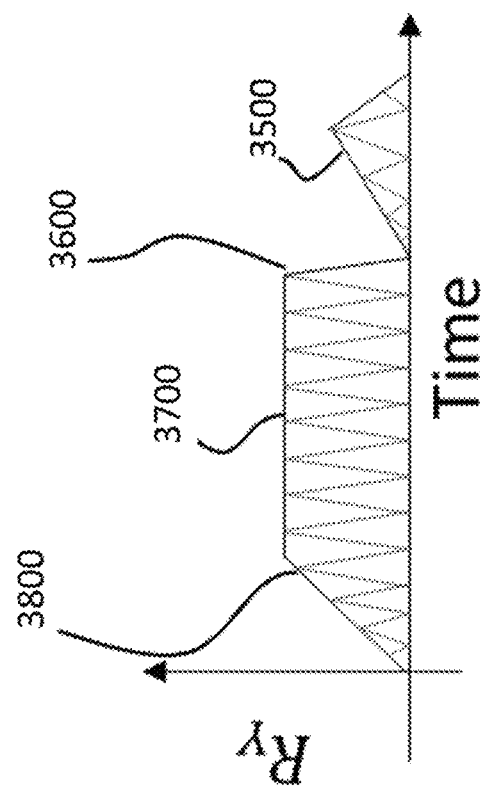
FIG. 15 provides a depiction of a pulsatile treatment plan in accordance with an embodiment of the invention.

In some instances, systems of the invention, e.g., as described above, are employed in a manner sufficient to achieve a four-part pulsatile treatment plan, e.g., as illustrated in FIG. 15, which four-part pulsatile treatment plan provides for safe, controlled expansion of hardened plaques and surrounding healthy soft tissues. To treat these multi-compositional vessels, a four-part treatment algorithm may be employed, which four-part treatment algorithm includes the following steps: (1) soft-tissue low-stress expansion phase 3800 via Mullins' Effect; (2) plastic deformation phase 3700 in the calcified plaque until plaque fracture; (3) plaque fracture detection and immediate reduction in pressure phase 3600 to reduce surrounding tissue stress; and (4) soft-tissue low-stress expansion phase 3500 via Mullins' Effect to expand soft-tissue post-calcium fracture. An embodiment in which the force applied to the vessel over time by this four-part algorithm is illustrated in FIG. 6. Because of the significant attenuation across the catheter and the lack of pressure control in prior art approaches, the input pressure to the catheter is not successfully transmitted to the balloon (the system output). Therefore, tissue stress in prior art systems is not returned to a low state (i.e., there is no tissue relaxation period) during high frequency oscillation, which limits the effect of Mullins' stress cycling. Through attenuation minimization and pressure control, the present system induces pressure oscillations in the balloon (the system output) that follows the pressure input from the proximal source with pressure oscillations between 0-50 ATM, frequencies between 0-25 Hz, and duty cycles between 60-80%. This advancement is important for two reasons: (1) it allows the tissue to relax during the depressurization cycle (following the Mullins' Effect) and (2) it allows sufficient oscillations to be applied to the vessel within the limited time during which an artery is occluded during treatment. Further details regarding methods in which embodiments of the invention may be used are found in pending PCT application serial no. PCT/US2020/055458; the disclosure of which is herein incorporated by reference.

In certain instances, embodiments of the present invention may be applied to assess vessel compliance. Blood vessels are naturally compliant, elastic structures. Their compliance is required to convert the pulsatile flow from the heart into steady flow in the capillaries. Over time, however, the aging and atherosclerotic process can diminish the compliance of vessels and reduce lumen area, creating flow mismatches and additional stress to the vascular system. Vessel compliance is especially diminished during and after the formation of intimal and medial calcified plaque in the vessel wall.

Improving vessel compliance is a prerequisite to a more definitive treatment of atherosclerosis. See Dattilo R, Himmelstein S I, Cuff R F. The COMPLIANCE 360° Trial: a randomized, prospective, multicenter, pilot study comparing acute and long-term results of orbital atherectomy to balloon angioplasty for calcified femoropopliteal disease. J Invasive Cardiol. 2014; 26(8):355-360. http://www.ncbi.nlm.nih.gov/pubmed/25091093. To maximize vessel wall compliance after calcium buildup, angioplasty or intravascular lithotripsy therapy can be used to shatter intimal and medial calcium rings to expose the more elastic components of the tubular vessel and to release it from the mummifying calcium. As noted above, embodiments of the present invention may be used to apply pulsatile intravascular lithotripsy enabling both for cracking of calcium (i.e., cracking CP tissue as shown in FIG. 14) as well as to apply a final post-dilatation of the vessel. In some cases, embodiments of the present invention may apply both applications, cracking CP tissue and applying a final post-dilation of the tissue, in a single treatment. That is, embodiments of the present invention can also be used to apply DBA first to apply pulses to a vessel to crack CP tissue and then to subsequently expand the vessel using, for example, a traditional, non-compliant balloon post-dilatation.

By vessel compliance, it is meant a measurable quantity defined by the following relationship:

$$C = \frac{\Delta V}{\Delta P}$$

where $\Delta V$ is the change in vessel volume for a given change in pressure $\Delta P$. Because of tissue incompressibility, vessel volume can be converted to area by dividing by vessel length. Since the pressure-volume relationship in an artery is non-linear, compliance is often defined at a given pressure or volume.

Vessel compliance can be difficult to obtain because simultaneous in-vivo measurements of pressure change, $\Delta P$, and vessel cross-sectional area or volume change, $\Delta A$ or $\Delta V$, respectively, may be challenging. Systems according to the present invention find use in addressing this difficulty by accurately assessing vessel compliance in-vivo as described below.

As reviewed above, the proximal connector of the catheter balloon assembly may include a membrane positional sensor, such as a Hall sensor, which provides data regarding the spatial position of the membrane at any given time, as well as a pressure gauge for measuring pressure in the liquid passages and distal balloon of the balloon catheter assembly. In such instances, the systems may be employed to assess volume expansion of the balloon in real time, and/or vessel compliance at the site of the balloon.

As a consequence of measuring the diaphragm (i.e., membrane) position, the change in volume in the balloon can be assessed in real time and the corresponding balloon pressure can be measured. That is, the system is configured to pressurize the balloon-based catheter while simultaneously reading pressure and volume in the catheter system. This volume-pressure relationship can provide a measure of vessel compliance, since, as described above, vessel compliance is the ratio of a change of vessel volume to a change in pressure. To enable this measurement, the balloon volume-pressure relationship can be measured when the balloon is uninhibited by a surrounding vessel. When located within a stiff vessel, the balloon requires a higher pressure for the equivalent balloon volume in its uninhibited, baseline state. Therefore, the balloon may be used to measure compliance of the vessel. With the ability to accurately record diaphragm position (a surrogate measurement for balloon volume) and balloon pressure, the compliance of the vessel can be measured easily in-vivo. This compliance measure can be used as a measure of a successful treatment with a lower compliance indicating adequate or therapeutic balloon expansion and a successful treatment. In some instances, the system is employed in methods analogous to those described in U.S. Published Application Publication No. 20150080747 (the disclosure of which is herein incorporated by reference), where membrane displacement is used as the measure of balloon volume.

Systems and methods for measuring vessel compliance according to the present invention may be configured to obtain pre-, during, and post-treatment pressure-volume measurements. Using the data obtained during these measurements, change in vessel compliance can be obtained to determine treatment efficacy. Change in vessel compliance may also be used to adjust therapeutic intensity and/or duration.

In addition, embodiments of the present invention may be used to generate pressure-volume (i.e., compliance curves) at various instances during treatment. A relative change in compliance pre- and post-treatment may be obtained. These changes may be compared amongst similar vessel segments to understand an appropriate level of compliance change.

In addition, methods according to the present invention may also comprise obtaining concomitant measures of intraarterial cross-section using other available measuring techniques such as ultrasound, cineangiography, computed tomography, intravascular ultrasound (IVUS), and/or optical coherence tomography (OCT). In some instances, systems according to the present invention may be configured to incorporate information obtained from such measurements, i.e., sensor fusion techniques. Volume and/or area measurements obtained through such visualization techniques may be combined with pressure and volume readings of embodiments of a balloon system according to the present invention (i.e., measurements of changes or relative volume and/or pressure) to generate absolute compliance measurements of vessels with increased accuracy. Such absolute compliance measurements may then be used to compare treatments across vascular beds for optimizing treatments for both short- and long-term success. In addition, an absolute measure of the compliance curve of a vessel may be obtained and compared across treatment groups.

While systems and methods of measuring vessel compliance have been described in the context of pulsatile balloon catheter systems according to the present invention, such systems and methods for measuring vessel compliance may be applied to other systems as well, such as systems configured to deliver static balloon angioplasty, pulsatile intravascular lithotripsy, cavitation-based intravascular lithotripsy, and/or externally-applied lithotripsy pulses.

Figure 16:
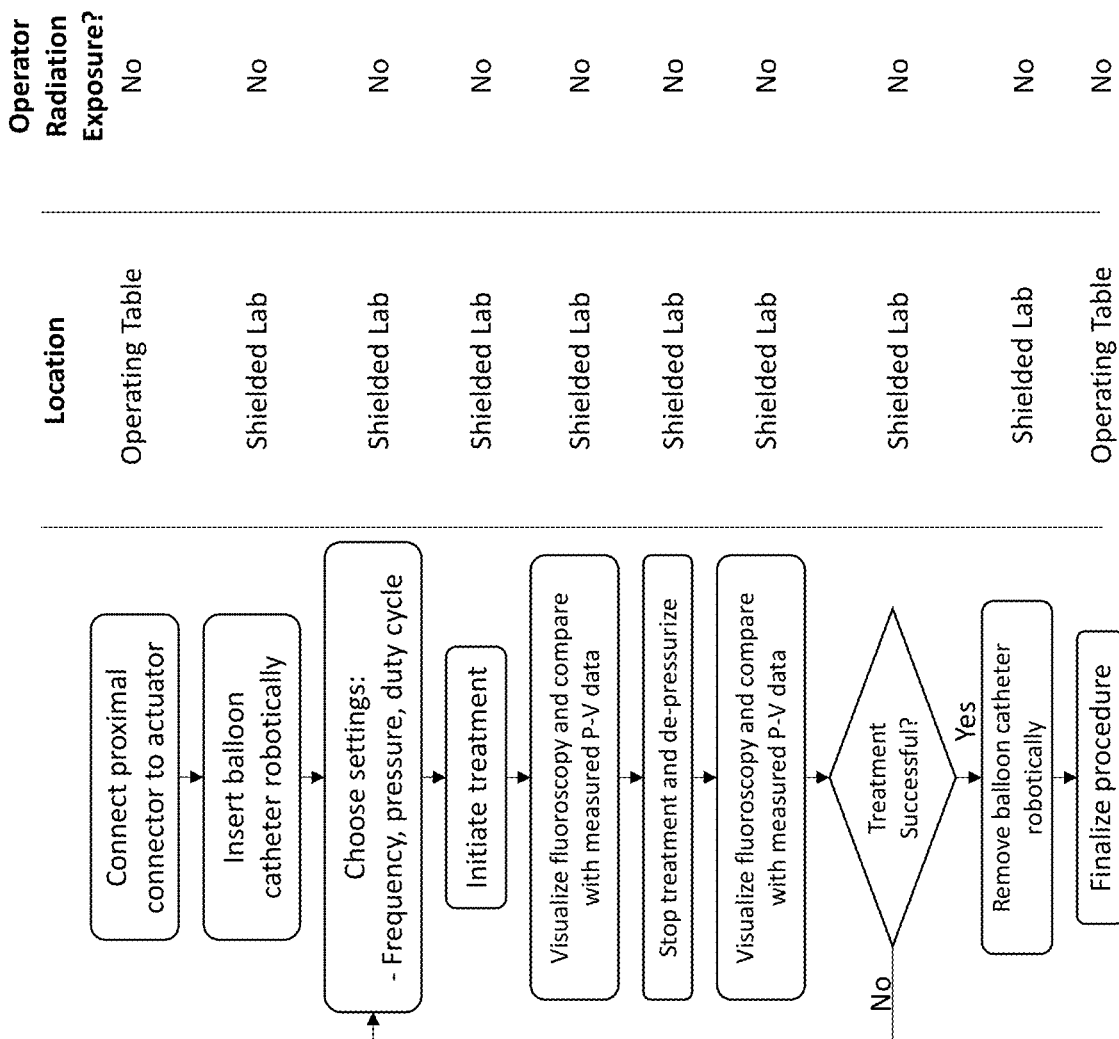
FIG. 16 shows the procedural steps of an autonomous angioplasty procedure performed with embodiments of the invention.

FIG. 16 shows the procedural steps of an autonomous angioplasty procedure performed with the embodiments described above. To initiate this autonomous procedure, the physician or technician in the sterile field may connect the proximal connector to the actuator of the embodied system. This step may involve some human interaction with the patient but, fluoroscopy may be paused to minimize operator exposure. In this embodiment, a robotic catheterization device (such as those known in the art may) be used to insert the angioplasty balloon across the lesion. This step may include fluoroscopy imaging and radiation but can be performed from within a shielded lab, eliminating operator radiation exposure. Once the appropriate balloon is across the lesion, the operator may choose the appropriate treatment setting and then initiate the treatment. Prior to, during, or after the procedure, the operator may visualize the fluoroscopy images and compare those images with the measure pressure-volume data. If the treatment is not successful, the procedure may be continued with the same or different settings. If the treatment is unsuccessful, the balloon catheter may be removed robotically. During these steps, the operator may remain inside the shielded lab and protected from radiation. In some instances, the pre-filled and/or spring-biased balloon catheter and/or a composite balloon may be used to minimize radiation exposure of the operator. In these instances, the operator does not have to fill the catheter with contrast solution, nor does s/he have to remove and collapse the balloon on procedure completion. Once all of these steps are performed and fluoroscopy is no longer needed, the procedure may be finalized.

Figure 17:
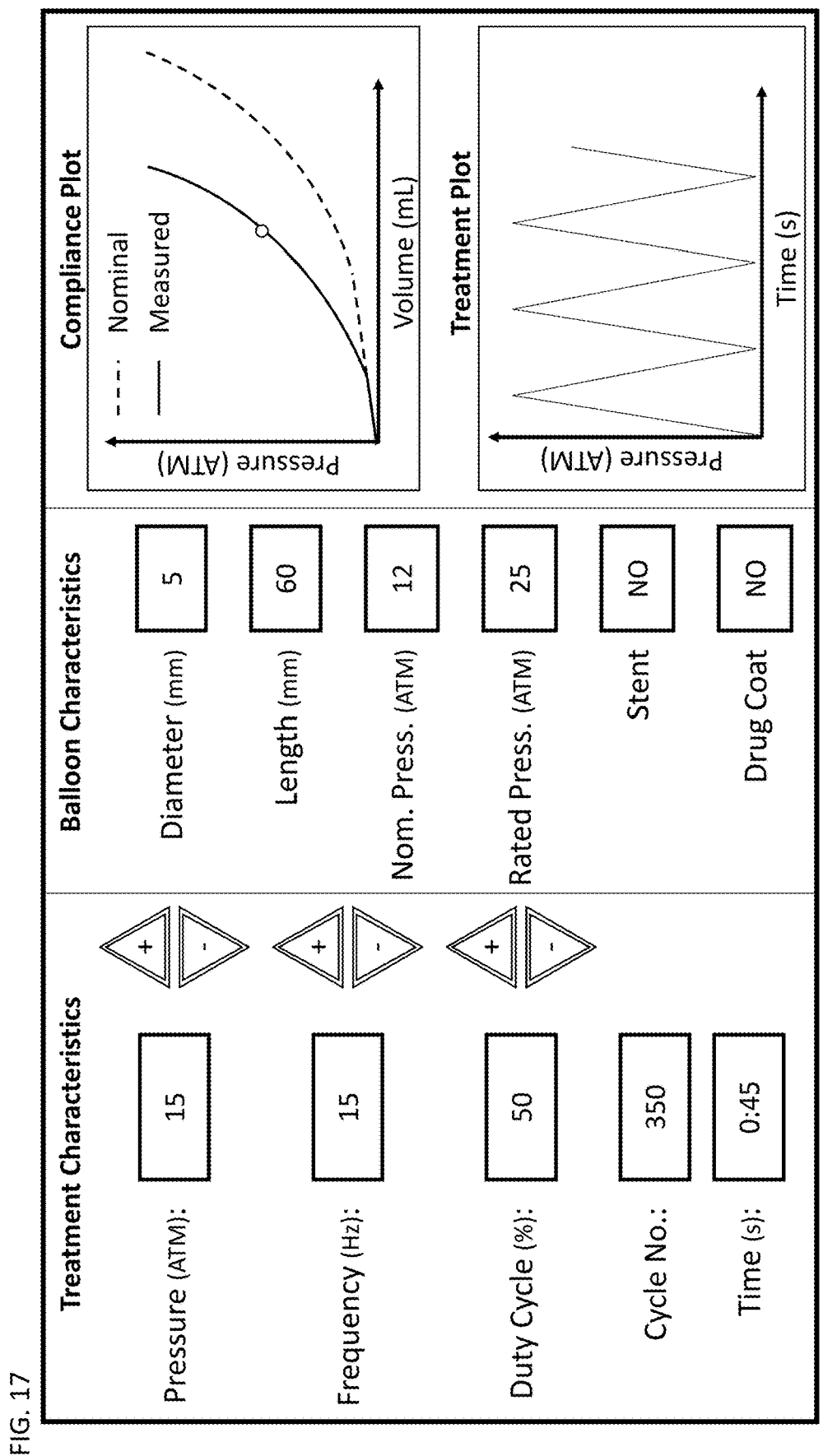
FIG. 17 shows a graphical user interface (GUI) that with which an operator may interface during an autonomous angioplasty procedure of embodiments of the invention, such as illustrated in FIG. 16.

FIG. 17 shows a graphical user interface (GUI) that the operator may interface with during the autonomous angioplasty procedure. In this embodiment, the GUI may have several information zones such as a Treatment Characteristics zone, Balloon Characteristics zone, and Plotting zone. The Treatment Characteristics zone indicates the important procedural characteristics that the operator employs during the procedure. Such characteristics include pressure, frequency, duty cycle, cycle number, and procedure time. Some or all of these characteristics may be updated or changed by the system and/or by the user. The Balloon Characteristics zone may include information regarding the balloon that has been attached to the handheld actuator. Information that may be displayed includes balloon diameter, length, nominal pressure, and rated pressure, and other balloon characteristics, such as drug-coated or stent covered balloons. Additionally, balloon catheter connectivity information (i.e., whether a balloon has been connected or not) can be included in this section. In the Plot zone, various procedural plots may be displayed including a compliance plot and treatment plot. The compliance plot may include a nominal pressure-volume curve that may be provided with the balloon. Additionally, a pressure-volume curve measured in-situ during the procedure may be plotted and updated throughout the procedure. The operator may use this plot to determine treatment effect as a measure of compliance or efficacy. The pressure plot may include a display of pressure versus time. Other information that may be included (not shown) on the GUI include treatment status and intensity, ON/OFF switches, indicator LEDs, and the like.

The systems may be used to apply pulsatile energy to internal tissue locations of any number of different subjects. In some instances, the subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans.

Kits

Also provided are kits that include systems, or one or more components thereof, e.g., as described above. As such, kits may include, in some instances, one or more of, balloon catheter assemblies, which may or may not be prefilled, pulse generators, or components thereof, e.g., hand-held actuators thereof, etc. The kit components may be present in packaging, which packaging may be sterile, as desired.

Also present in the kit may be instructions for using the kit components. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD- or CD-ROM, etc. The instructions may take any form, including complete instructions for how to use the device or as a website address with which instructions posted on the world wide web may be accessed.

The following example(s) is/are offered by way of illustration and not by way of limitation.

EXAMPLES

Figure 18:
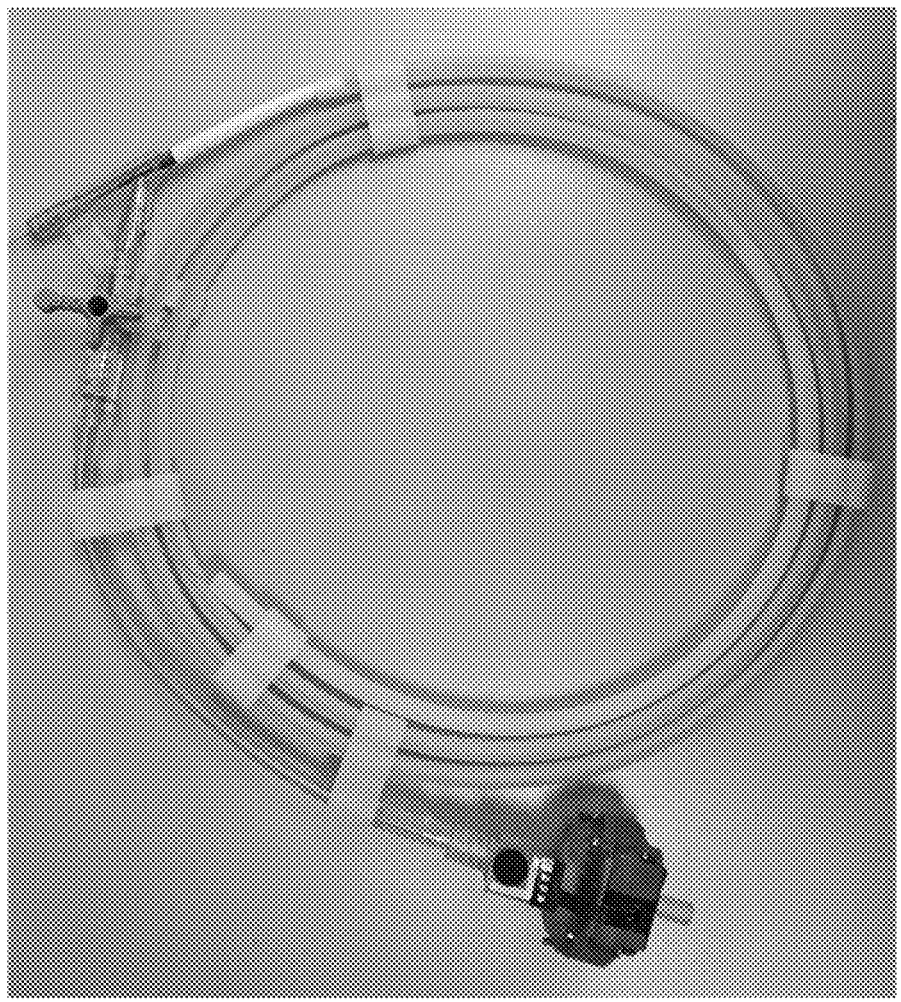
FIG. 18 provides a photograph of a balloon catheter assembly according to an embodiment of the invention.
Figure 19:
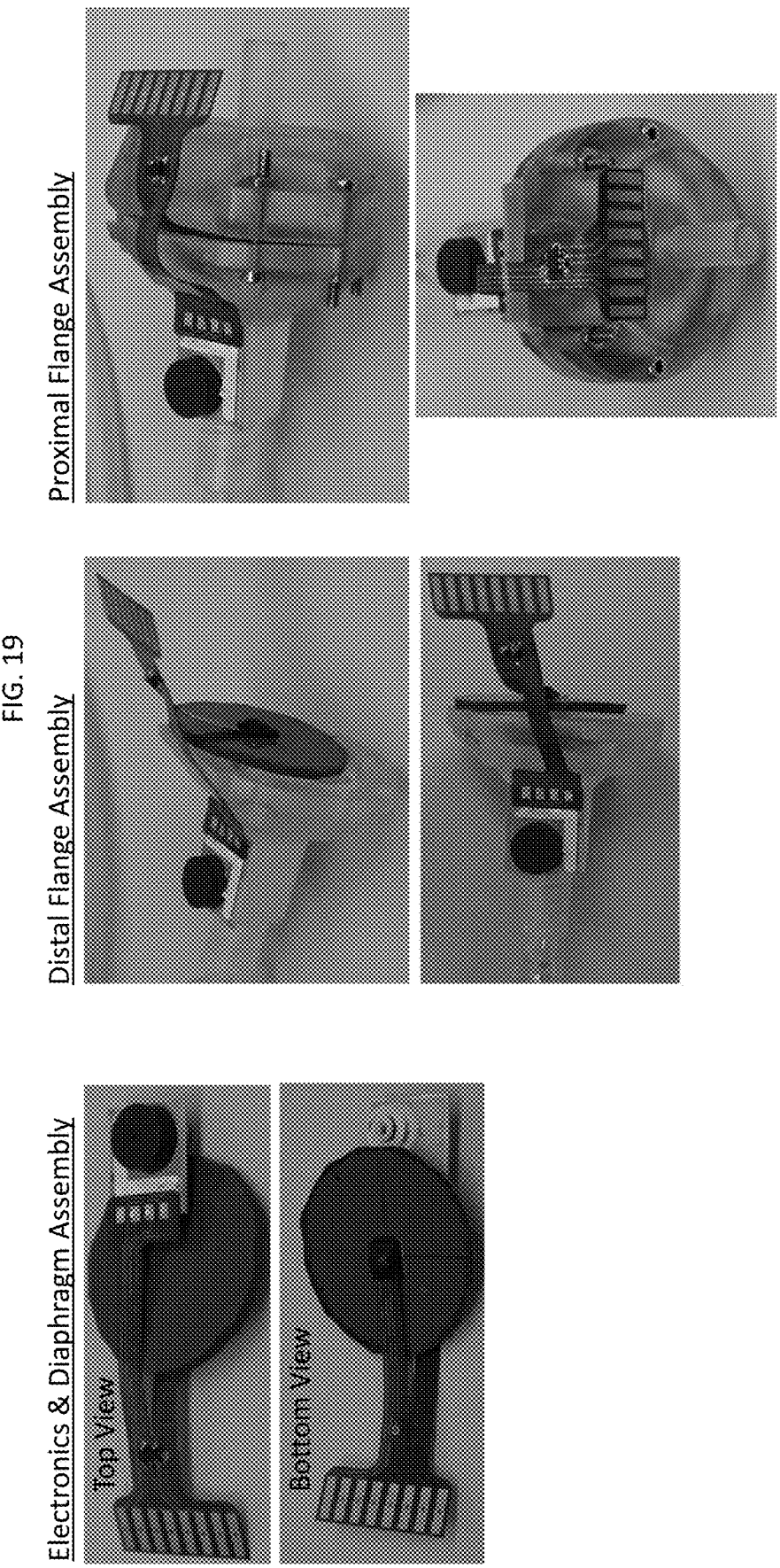
FIG. 19 provides various photographic views of the proximal connector of the balloon catheter assembly of FIG. 18.
Figure 20:
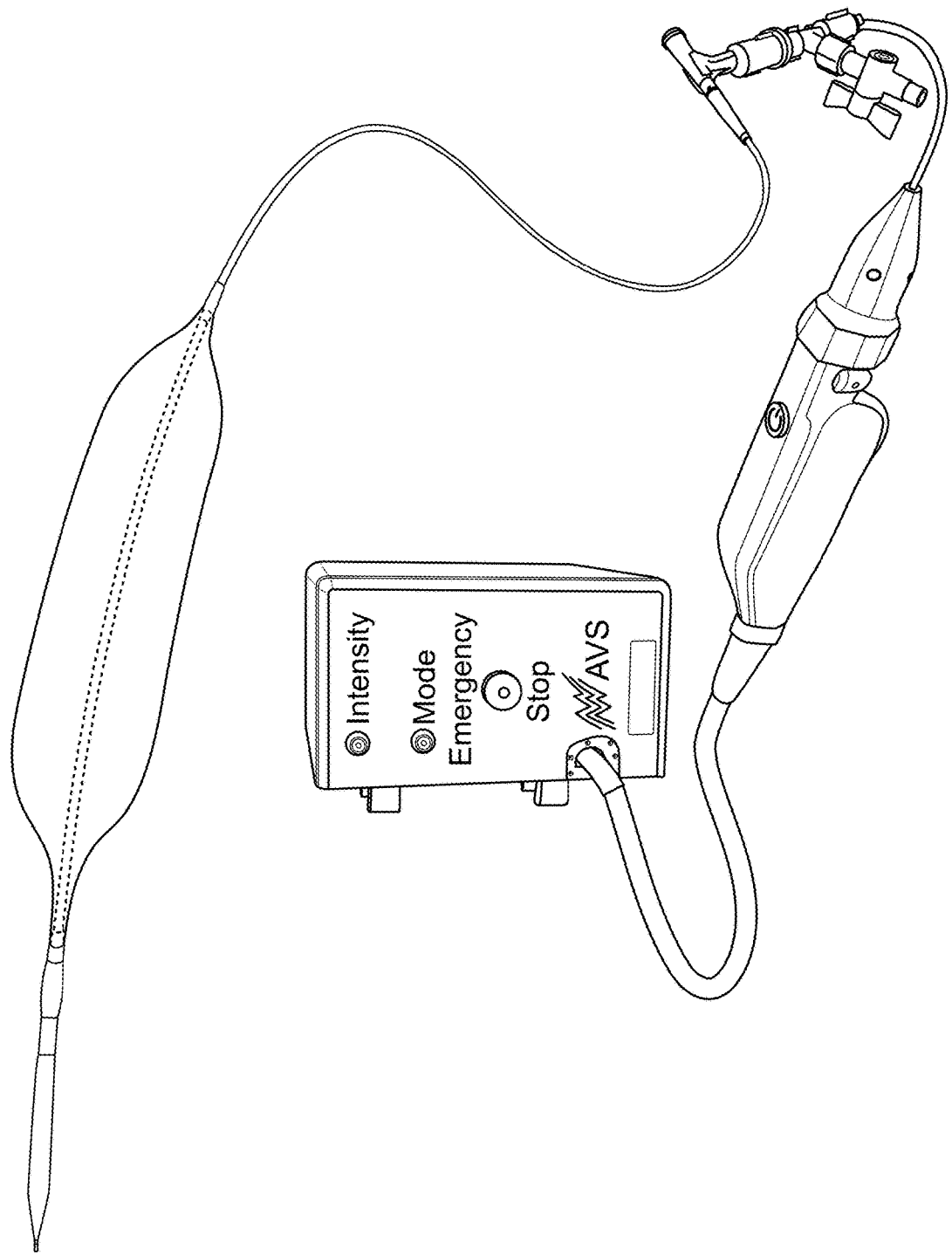
FIG. 20 provides a picture of a balloon catheter system according to an embodiment of the invention.

FIG. 18 provides a picture of a balloon catheter assembly according to an embodiment of the invention. FIG. 19 shows the assembly process for the proximal connector of the balloon catheter assembly shown in FIG. 18. The first step of the assembly process is to fix the electronic flexible printed circuit board assembly to the diaphragm and pressure sensor. For example, epoxy and solder, respectively, may be used. The pressure sensor and diaphragm may be fixed to the distal flange. Using an appropriate fixation technique (e.g., fasteners, welding, etc.), the proximal flange may be fixed to the distal flange. The electronic connector may be fixed to the front face of the proximal flange with epoxy, for example, so as to provide a reliable connection to the hand-held actuator. FIG. 6 represents testing performed on the described embodiment and physical assembly. The pressure is shown to increase while the force at the distal balloon increases as well. The force produced during oscillation matches the force produced during static inflation, indicating minimal attenuation by the system during pulsation. FIG. 20 provides a picture of a balloon catheter system according to an embodiment of the invention, such as a balloon catheter system comprising an embodiment of a balloon catheter assembly shown in FIG. 18.

Embodiments of the invention provide a number of advantages, which advantages include, but are not limited to:

with the pre-filled balloon catheter and composite balloon embodiments, the operator does not have to fill the balloon catheter with a contrast/saline mixture, which is an improvement since the amount of fluid that may be introduced by the clinician at the time of treatment may be variable, there may be errors in volume insertion, debubbling, deflating, etc.;

if the balloon is not pre-filled, the diaphragm tracking mechanism provides a method of measuring the appropriate volume inserted into the system;

with the pre-filled balloon catheter and composite balloon embodiments, the volume-pressure relationship in the balloon can be pre-measured and can be used to make decisions during treatment;

embodiments allow for angioplasty pressurizations to be performed with minimal physician interactions, thereby limiting physician exposure to dangerous X-rays from fluoroscopy the balloon may have an internal memory, which informs the rest of the system of the potential treatment characteristics.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A pulsatile balloon catheter system, the system comprising:
   (a) a pulse generator; and
   (b) a balloon catheter assembly operably connected to the pulse generator, the balloon catheter assembly comprising:
   (i) a proximal connector operably connecting the balloon catheter assembly to the pulse generator, wherein the proximal connector comprises:
      a proximal chamber and a distal chamber separated by a membrane,
      a pressure sensor operably coupled to the distal chamber, and
      a membrane positional sensor that directly measures changes in spatial position of the membrane;
   (ii) a distal balloon; and
   (iii) a catheter component comprising a fluidic passage operably positioned between the proximal connector and the distal balloon;
   wherein the system is configured to assess vessel compliance based on changes in pressure detected by the pressure sensor and changes in volume based on changes in position of the membrane detected by the membrane positional sensor.

2. The pulsatile balloon catheter system according to claim 1, wherein the membrane positional sensor comprises a Hall Sensor affixed to the membrane and a permanent magnet attached to the proximal connector, wherein the permanent magnet is configured to remain in a fixed position relative to movement of the membrane, and
   wherein the membrane positional sensor further comprises an electrical lead operably connected to the Hall sensor affixed to the membrane and configured to output a voltage signal indicative of membrane position.

3. The pulsatile balloon catheter system according to claim 2, wherein the membrane positional sensor is configured such that the permanent magnet modulates voltage of the Hall Sensor upon membrane movement.

4. The pulsatile balloon catheter system according to claim 1, further configured to assess vessel compliance in real time during treatment.

5. The pulsatile balloon catheter system according to claim 1, further configured to assess vessel compliance before and after treatment.

6. The pulsatile balloon catheter system according to claim 1, wherein the system is further configured to assess treatment efficacy based on changes in vessel compliance.

7. The pulsatile balloon catheter system according to claim 1, further configured to detect system states.

8. The pulsatile balloon catheter system according to claim 7, further comprising an electronic circuit configured to detect system states.

9. The pulsatile balloon catheter system according to claim 8, wherein the electronic circuit is configured to compare a measured system characteristic to a target threshold.

10. The pulsatile balloon catheter system according to claim 9, wherein the measured system characteristic comprises pressure.

11. The pulsatile balloon catheter system according to claim 10, wherein the measured pressure is catheter pressure.

12. The pulsatile balloon catheter system according to claim 11, wherein the measured catheter pressure is a maximal amplitude of pulsatile catheter pressure.

13. The pulsatile balloon catheter system according to claim 9, wherein the measured system characteristic comprises volume.

14. The pulsatile balloon catheter system according to claim 13, wherein the measured volume is distal balloon volume.

15. The pulsatile balloon catheter system according to claim 14, wherein the measured distal balloon volume is a maximal distal balloon volume.

16. The pulsatile balloon catheter system according to claim 9, wherein the electronic circuit comprises:
   a comparator circuit, configured to compare the measured system characteristic against the target threshold; and
   a flip-flop, configured to store the result of the comparator circuit, wherein
   the flip-flop is clocked based on a pressure control signal, and
   the stored data value of the flip-flop reflects a system state.

17. The pulsatile balloon catheter system according to claim 16, wherein the circuit is configured to write a result of the comparator circuit to the flip-flop so that the result corresponds to a comparison of expected maximal amplitude catheter pressure or expected maximal distal balloon volume.

18. The pulsatile balloon catheter system according to claim 16, wherein the pressure control signal is based on a catheter pressure control signal.

19. The pulsatile balloon catheter system according to claim 18, wherein the catheter pressure control signal is a solenoid trigger signal.

20. The pulsatile balloon catheter system according to claim 19, wherein the circuit is configured to write the result of the comparator circuit to the flip-flop upon the trailing edge of the solenoid trigger signal.

21. The pulsatile balloon catheter system according to claim 7, wherein the detected system state is one or more of a pressure fault, a system leak, or a balloon burst.

22. The pulsatile balloon catheter system according to claim 1, wherein the membrane positional sensor is operably connected to an electrical assembly comprising circuitry and/or memory.

23. A pulsatile balloon catheter system, the system comprising:
   (a) a pulse generator; and
   (b) a balloon catheter assembly operably connected to the pulse generator, the balloon catheter assembly comprising:
   (i) a proximal connector operably connecting the balloon catheter assembly to the pulse generator, wherein the proximal connector comprises:
      a proximal chamber and a distal chamber separated by a membrane, and
      a membrane positional sensor that directly measures changes in spatial position of the membrane;
   (ii) a distal balloon; and
   (iii) a catheter component comprising a fluidic passage operably positioned between the proximal connector and the distal balloon.

24. The pulsatile balloon catheter system according to claim 23, wherein the membrane positional sensor is operably connected to an electrical assembly comprising circuitry and/or memory.

25. The pulsatile balloon catheter system according to claim 23, wherein the membrane positional sensor comprises a Hall Sensor affixed to the membrane and a permanent magnet attached to the proximal connector, wherein the permanent magnet is configured to remain in a fixed position relative to movement of the membrane, and wherein the membrane positional sensor further comprises an electrical lead operably connected to the Hall sensor affixed to the membrane and configured to output a voltage signal indicative of membrane position.

26. The pulsatile balloon catheter system according to claim 25, wherein the membrane positional sensor is configured such that the permanent magnet modulates voltage of the Hall Sensor upon membrane movement.

* * * * *